(12) United States Patent
Doi et al.

(10) Patent No.: US 7,901,874 B2
(45) Date of Patent: Mar. 8, 2011

(54) METHODS FOR IDENTIFYING AGENTS FOR PREVENTING OR TREATING PROLIFERATIVE DISEASES, AND FOR INHIBITING EXTRACELLULAR MATRIX OR α1 TYPE IV COLLAGEN

(75) Inventors: Toshio Doi, Kyoto (JP); Hideharu Abe, Tokushima (JP)

(73) Assignees: Hubit Genomix, Inc., Tokyo (JP); Chugai Seiyaku Kabushiki Kaisha, Tokyo (JP)

( * ) Notice: Subject to any disclaimer, the term of this patent is extended or adjusted under 35 U.S.C. 154(b) by 761 days.

(21) Appl. No.: 10/571,511

(22) PCT Filed: Sep. 9, 2004

(86) PCT No.: PCT/JP2004/013124
§ 371 (c)(1),
(2), (4) Date: Jan. 8, 2007

(87) PCT Pub. No.: WO2005/026344
PCT Pub. Date: Mar. 24, 2005

(65) Prior Publication Data
US 2008/0025967 A1 Jan. 31, 2008

(30) Foreign Application Priority Data
Sep. 11, 2003 (JP) .................................. 2003-319538

(51) Int. Cl.
G01N 33/48 (2006.01)
G01N 33/50 (2006.01)
G01N 33/53 (2006.01)
G01N 33/68 (2006.01)

(52) U.S. Cl. ................. 435/4; 435/6; 435/7.1; 435/7.21; 435/7.8

(58) Field of Classification Search ........................ None
See application file for complete search history.

(56) References Cited

U.S. PATENT DOCUMENTS 5,908,925 A * 6/1999 Cohen et al. ............... 536/23.53
6,013,522 A 1/2000 Monia et al.

FOREIGN PATENT DOCUMENTS

WO WO 01/79555 A2 10/2001
WO WO 03/042211 A1 5/2003

OTHER PUBLICATIONS

Deininger et al., 1995, Acta Neuropathol 90:76-79.*
Chen et al, "STAT1 and STAT3 mediate thrombin-induced expression of TIMP-1 in human glomerular mesangial cells," Kidney International, vol. 61, No. 4, pp. 1377-1382, XP-002450930 (2002).
Huang et al, "Role of Janus kinase (JAK)/signal transducters and activators of transcription (STAT) cascade in advanced glycation end-product-induced cellular mitogenesis in NRK-49F cells," Biochemistry Journal, Portland Press, London, GB, vol. 342, No. 1, pp. 231-238, XP-002242680 (1999).
Huang et al, "Role of Receptor for Advanced Glycation End-Product (RAGE) and the JAK/STAT-Signaling Pathway in AGE-Induced Collagen Production in NRK-49F Cells," Journal of Cellular Biochemistry, Wiley-Liss Inc, US, vol. 81, No. 1, pp. 102-113, XP003006569 (2001).
Isono et al, "Smad pathway is activated in the diabetic mouse kidney and Smad3 mediates TGF-β-induced fibronectin in mesangial cells," Biochemical and Biophysical Research Communications, vol. 296, No. 5, pp. 1356-1365, XP-002450931 (2002).
Johnson et al, "Inhibition of Mesangial Cell Proliferation and matrix Expansion in Glomerulonephritis in the Rat by Antibody to Platelet-derived Growth Factor," Journal of Experimental Medicine, vol. 175, pp. 1413-1416, XP-002058747 (1999).
Nakashima et al, "Synergistic Signaling in Fetal Brain by STAT3-Smad1 Complex Bridged by p300," Science, vol. 284, pp. 479-482, XP-002451726 (1999).
Supplementary Partial European Search Report dated Oct. 4, 2007, for European Patent Application No. EP 04787788, filed Mar. 27, 2006.
Horiguchi et al., "Activation of Signal Transducer and Activator of Transcription 3 in Renal Cell Carcinoma: A study of Incidence and Its Association with Pathological Features and Clinical Outcome",The Journal of Urology, vol. 168: 762-765 (2002).
Wang et al., "Inhibition of the JAK/STAT Signaling Pathway Prevents the High Glucose-Induced Increase in TGF-β and Fibronectin Synthesis in Mesangial Cells", Diabetes vol. 51: 3505-3509 (2002).
International Search Report for application No. PCT/JP2004/013124, mailed Nov. 30, 2004.
Horiguchi, A. et al., Activation of signal transducer and activator of transcription 3 in renal cell carcinoma: a study of incidence and its association with pathological features and clinical outcome:, J. Urol., (Aug. 2002), vol. 168, No. 2, pp. 762 to 765.
Wang, X. et al., "Inhibition of the Jak/STAT signaling pathway prevents the high glucose-induced increase in tgf-beta and fibronectin synthesis in mesangial cells", Diabetes, (Dec. 2002), vol. 51, No. 12, pp. 3505 to 3509.

(Continued)

Primary Examiner — Elizabeth C. Kemmerer
(74) Attorney, Agent, or Firm — Birch, Stewart, Kolasch & Birch, LLP

(57) ABSTRACT

A method of detecting proliferative diseases causing sclerosis, comprising measuring the expression of at least one substance selected from the group consisting of STAT3, phosphorylated STAT3, Smad1, phosphorylated Smad1, activin receptor-like kinase 1, activin receptor-like kinase 3 and bone morphogenetic proteins in a biological sample. A kit therefor. A prophylactic and/or therapeutic agent for proliferative diseases causing sclerosis, comprising as an active ingredient a substance having an inhibitory effect on the expression of at least one substance selected from the group consisting of STAT3, phosphorylated STAT3, Smad1 and phosphorylated Smad1. A method of identifying substances effective in preventing and/or treating proliferative diseases causing sclerosis, comprising judging whether or not a test substance inhibits the expression of at least one substance selected from the group consisting of STAT3, phosphorylated STAT3, Smad1 and phosphorylated Smad1. A kit therefor.

10 Claims, 19 Drawing Sheets
(6 of 19 Drawing Sheet(s) Filed in Color)

OTHER PUBLICATIONS

Huang, J.S. et al., "Role of the Janus kinase (JAK)/signal transducers and activators of transcription (STAT) cascade in advanced glycation end-product-induced cellular mitogenes is in NRK-49F cells", Biochem.J., (Aug. 1999), vol. 15, No. 342 (Pt. 1), pp. 231 to 238.

Wang, S.N. et al., "Loss of tubular bone morphogenetic protein-7 in diabetic nephropathy",J.Am.Soc.Nephrol., (Nov. 2001), vol. 12, No. 11, pp. 2392 to 2399.

Yang, C.W. et al., "Advanced glycation end products up-regulate gene expression found in diabetic glomerular disease", Proc. Natl. Acad.Sci.USA, (1994), vol. 91, No. 20, pp. 9436 to 9440.

Paul Oh, S. et al., "Activin receptor-like kinase 1 modulates transforming growth factor-$\beta$ 1 signaling in the regulation of angiogenesis", Proc. Natl. Acad. Sci. USA, (2000), vol. 97, No. 6, pp. 2626 to 2631.

Gupta, I.R. et al., "BMP-2/ALK3 and HGF signal in parallel to regulate renal collecting duct morphogensis", J.Cell Sci., (Jan. 2000), vol. 113, Pt.2, pp. 269 to 278.

Abe, H. et al., "Type IV collagen is transcriptionally regulated by Smad1 under advanced glycation end product (AGE) stimulation", J. Biol. Chem., (Apr. 2004), vol. 279, No. 14, pp. 14201 to 14206.

Written Opinion of the International Searching Authority for PCT/JP2004/013124 mailed Jun. 29, 2006.

Oh, S. Paul, Activin receptor-like kinase 1 modulates transforming growth factor-$\beta$1 signaling in the regulation of angiogensis, PNAS, Mar. 14, 2000, 1626-2631, vol. 97, No. 6.

Gupta et al., BMP-2/ALK3 and HGF signal in parallel to regulate renal collecting duct morphogenesis, J. Cell Sci. (Jan. 2000), vol. 113, Pt 2, pp. 269-278.

\* cited by examiner

Fig. 5

Array analysis (AGEs stimulation on mMC)

| | AGE/BSA | Ratio AGE/BSA(color swap) |
|---|---|---|
| BMP4 | 21.25 | 2.32 |
| BMP1 | 2.06 | 2.07 |
| SMAD1 | 1.27 | 1.22 |
| RAGE | 1.15 | 5.6 |
| TGFbRII | 0.49 | 12.1 |
| TGFbRI | 1.15 | 1.1 |
| ALK3 | 1.18 | 1.3 |
| BMPRII | 2.06 | 4.74 |

Western blot (human urine Smad1)

Lanes 1-5: diabetic nephropathy
Lane 6: mitochondrial disease in which diabetes is complicated with sclerosing, renal proliferative disease
Lanes 7-8: diabetes + nephritis (without sclerosis)
Lanes 9-1: normal

SEQUENCE LISTING

```
<160> NUMBER OF SEQ ID NOS: 30

<210> SEQ ID NO 1
<211> LENGTH: 1990
<212> TYPE: DNA
<213> ORGANISM: Homo sapiens
<220> FEATURE:
<221> NAME/KEY: CDS
<222> LOCATION: (433)..(1830)

<400> SEQUENCE: 1
gaattccggg ggtattggca gctgaggagt ggaggctggg cagctccgac tccctgacgc      60
cagcgcgacc agatcaatcc aggctccagg agaaagcagg cgggcgggcg gagaaaggag     120
aggccgagcg gctcaacccg ggccgaggct cggggagcgg agagtggcgc accgcccggc     180
cgtccggacc cgggccgcga gacccccgctc gcccggccac tcgtgctccc gcacggacgg     240
gcgcgccgcc aacccggtgc tgactgggtt acttttttaa acactaggaa tggtaatttc     300
tactcttctg gacttcaaac taagaagtta aagagacttc tctgtaaata aacaaatctc     360
ttctgctgtc cttttgcatt tggagacagc tttatttcac catatccaag gagtataact     420
agtgctgtca tt atg aat gtg aca agt tta ttt tcc ttt aca agt cca gct    471
```

```
            Met Asn Val Thr Ser Leu Phe Ser Phe Thr Ser Pro Ala
             1               5                  10 gtg aag aga ctt ctt ggg tgg aaa cag ggc gat gaa gaa aaa tgg     519
Val Lys Arg Leu Leu Gly Trp Lys Gln Gly Asp Glu Glu Lys Trp
     15              20                  25 gca gag aaa gct gtt gat gct ttg gtg aaa aaa ctg aag aaa aag aaa 567
Ala Glu Lys Ala Val Asp Ala Leu Val Lys Lys Leu Lys Lys Lys
 30              35                  40                  45 ggt gcc atg gag gaa ctg gaa aag gcc ttg agc tgc cca ggg caa ccg 615
Gly Ala Met Glu Glu Leu Glu Lys Ala Leu Ser Cys Pro Gly Gln Pro
             50                  55                  60 agt aac tgt gtc acc att ccc cgc tct ctg gat ggc agg ctg caa gtc 663
Ser Asn Cys Val Thr Ile Pro Arg Ser Leu Asp Gly Arg Leu Gln Val
             65                  70                  75 tcc cac cgg aag gga ctg cct cat gtc att tac tgc cgt gtg tgg cgc 711
Ser His Arg Lys Gly Leu Pro His Val Ile Tyr Cys Arg Val Trp Arg
             80                  85                  90 tgg ccc gat ctt cag agc cac cat gaa cta aaa cca ctg gaa tgc tgt 759
Trp Pro Asp Leu Gln Ser His His Glu Leu Lys Pro Leu Glu Cys Cys
         95                 100                 105 gag ttt cct ttt ggt tcc aag cag aag gag gtc tgc atc aat ccc tac 807
Glu Phe Pro Phe Gly Ser Lys Gln Lys Glu Val Cys Ile Asn Pro Tyr
110                 115                 120                 125 cac tat aag aga gta gaa agc cct gta ctt cct cct gtg ctg gtt cca 855
His Tyr Lys Arg Val Glu Ser Pro Val Leu Pro Pro Val Leu Val Pro
                130                 135                 140 aga cac agc gaa tat aat cct cag cac agc ctc tta gct cag ttc cgt 903
Arg His Ser Glu Tyr Asn Pro Gln His Ser Leu Leu Ala Gln Phe Arg
                145                 150                 155 aac tta gga caa aat gag cct cac atg cca ctc aac gcc act ttt cca 951
Asn Leu Gly Gln Asn Glu Pro His Met Pro Leu Asn Ala Thr Phe Pro
            160                 165                 170 gat tct ttc cag caa ccc aac agc cac ccg ttt cct cac tct ccc aat 999
Asp Ser Phe Gln Gln Pro Asn Ser His Pro Phe Pro His Ser Pro Asn
    175                 180                 185 agc agt tac cca aac tct cct ggg agc agc agc agc acc tac cct cac 1047
Ser Ser Tyr Pro Asn Ser Pro Gly Ser Ser Ser Ser Thr Tyr Pro His
190                 195                 200                 205 tct ccc acc agc tca gac cca gga agc cct ttc cag atg cca gct gat 1095
Ser Pro Thr Ser Ser Asp Pro Gly Ser Pro Phe Gln Met Pro Ala Asp
                210                 215                 220 acg ccc cca cct gct tac ctg cct cct gaa gac ccc atg acc cag gat 1143
Thr Pro Pro Pro Ala Tyr Leu Pro Pro Glu Asp Pro Met Thr Gln Asp
            225                 230                 235 ggc tct cag ccg atg gac aca aac atg atg gcg cct ccc ctg ccc tca 1191
Gly Ser Gln Pro Met Asp Thr Asn Met Met Ala Pro Pro Leu Pro Ser
        240                 245                 250 gaa atc aac aga gga gat gtt cag gcg gtt gct tat gag gaa cca aaa 1239
Glu Ile Asn Arg Gly Asp Val Gln Ala Val Ala Tyr Glu Glu Pro Lys
    255                 260                 265 cac tgg tgc tct att gtc tac tat gag ctc aac aat cgt gtg ggt gaa 1287
His Trp Cys Ser Ile Val Tyr Tyr Glu Leu Asn Asn Arg Val Gly Glu
270                 275                 280                 285 gcg ttc cat gcc tcc tcc aca agt gtg ttg gtg gat ggt ttc act gat 1335
Ala Phe His Ala Ser Ser Thr Ser Val Leu Val Asp Gly Phe Thr Asp
                290                 295                 300 cct tcc aac aat aag aac cgt ttc tgc ctt ggg ctg ctc tcc aat gtt 1383
Pro Ser Asn Asn Lys Asn Arg Phe Cys Leu Gly Leu Leu Ser Asn Val
            305                 310                 315 aac cgg aat tcc act att gaa aac acc agg cgg cat att gga aaa gga 1431
```

|  |  |  |  |  |  |  |  |  |  |  |  |  |  |  |
|---|---|---|---|---|---|---|---|---|---|---|---|---|---|---|
|  | Asn | Arg | Asn | Ser | Thr | Ile | Glu | Asn | Thr | Arg | Arg | His | Ile | Gly | Lys | Gly |
|  |  | 320 |  |  |  | 325 |  |  |  |  | 330 |  |  |  |  |

| gtt | cat | ctt | tat | tat | gtt | gga | ggg | gag | gtg | tat | gcc | gaa | tgc | ctt | agt | 1479 |
| Val | His | Leu | Tyr | Tyr | Val | Gly | Gly | Glu | Val | Tyr | Ala | Glu | Cys | Leu | Ser |  |
| 335 |  |  |  |  | 340 |  |  |  |  | 345 |  |  |  |  |  |  |

| gac | agt | agc | atc | ttt | gtg | caa | agt | cgg | aac | tgc | aac | tac | cat | cat | gga | 1527 |
| Asp | Ser | Ser | Ile | Phe | Val | Gln | Ser | Arg | Asn | Cys | Asn | Tyr | His | His | Gly |  |
| 350 |  |  |  |  | 355 |  |  |  |  | 360 |  |  |  |  | 365 |  |

| ttt | cat | cct | act | act | gtt | tgc | aag | atc | cct | agt | ggg | tgt | agt | ctg | aaa | 1575 |
| Phe | His | Pro | Thr | Thr | Val | Cys | Lys | Ile | Pro | Ser | Gly | Cys | Ser | Leu | Lys |  |
|  |  |  |  | 370 |  |  |  |  | 375 |  |  |  |  | 380 |  |  |

| att | ttt | aac | aac | caa | gaa | ttt | gct | cag | tta | ttg | gca | cag | tct | gtg | aac | 1623 |
| Ile | Phe | Asn | Asn | Gln | Glu | Phe | Ala | Gln | Leu | Leu | Ala | Gln | Ser | Val | Asn |  |
|  |  |  |  | 385 |  |  |  |  | 390 |  |  |  |  | 395 |  |  |

| cat | gga | ttt | gag | aca | gtc | tat | gag | ctt | aca | aaa | atg | tgt | act | ata | cgt | 1671 |
| His | Gly | Phe | Glu | Thr | Val | Tyr | Glu | Leu | Thr | Lys | Met | Cys | Thr | Ile | Arg |  |
|  |  |  | 400 |  |  |  |  | 405 |  |  |  |  | 410 |  |  |  |

| atg | agc | ttt | gtg | aag | ggc | tgg | gga | gca | gaa | tac | cac | cgc | cag | gat | gtt | 1719 |
| Met | Ser | Phe | Val | Lys | Gly | Trp | Gly | Ala | Glu | Tyr | His | Arg | Gln | Asp | Val |  |
|  | 415 |  |  |  |  | 420 |  |  |  |  | 425 |  |  |  |  |  |

| act | agc | acc | ccc | tgc | tgg | att | gag | ata | cat | ctg | cac | ggc | ccc | ctc | cag | 1767 |
| Thr | Ser | Thr | Pro | Cys | Trp | Ile | Glu | Ile | His | Leu | His | Gly | Pro | Leu | Gln |  |
| 430 |  |  |  |  | 435 |  |  |  |  | 440 |  |  |  |  | 445 |  |

| tgg | ctg | gat | aaa | gtt | ctt | act | caa | atg | ggt | tca | cct | cat | aat | cct | att | 1815 |
| Trp | Leu | Asp | Lys | Val | Leu | Thr | Gln | Met | Gly | Ser | Pro | His | Asn | Pro | Ile |  |
|  |  |  |  | 450 |  |  |  |  | 455 |  |  |  |  | 460 |  |  |

| tca | tct | gta | tct | taa | atggcccag | catctgcctc | tggaaaacta | ttgagccttg | 1870 |
| Ser | Ser | Val | Ser |  |  |  |  |  |  |
|  |  |  | 465 |  |  |  |  |  |  |

| catgtacttg | aaggatggat | gagtcagaca | cgattgagaa | ctgacaaagg | agccttgata | 1930 |

| atacttgacc | tctgtgacca | actgttggat | tcagaaattt | aaacaaaaaa | aaaaaaaaaa | 1990 |

<210> SEQ ID NO 2
<211> LENGTH: 1970
<212> TYPE: DNA
<213> ORGANISM: Homo sapiens
<220> FEATURE:
<221> NAME/KEY: CDS
<222> LOCATION: (283)..(1794)

<400> SEQUENCE: 2

| aggaaacggt | ttattaggag | ggagtggtgg | agctgggcca | ggcaggaaga | cgctggaata | 60 |

| agaaacattt | ttgctccagc | ccccatccca | gtcccgggag | ctgccgcgc | cagctgcgcc | 120 |

| gagcgagccc | ctccccggct | ccagcccggt | ccggggccgc | gccggacccc | agcccgccgt | 180 |

| ccagcgctgg | cggtgcaact | gcggccgcgc | ggtggagggg | aggtggcccc | ggtccgccga | 240 |

| aggctagcgc | cccgccaccc | gcagagcggg | cccagaggga | cc atg acc ttg ggc | 294 |
|  |  |  |  | Met Thr Leu Gly |  |
|  |  |  |  | 1 |  |

| tcc | ccc | agg | aaa | ggc | ctt | ctg | atg | ctg | ctg | atg | gcc | ttg | gtg | acc | cag | 342 |
| Ser | Pro | Arg | Lys | Gly | Leu | Leu | Met | Leu | Leu | Met | Ala | Leu | Val | Thr | Gln |  |
| 5 |  |  |  | 10 |  |  |  |  | 15 |  |  |  |  | 20 |  |  |

| gga | gac | cct | gtg | aag | ccg | tct | cgg | ggc | ccg | ctg | gtg | acc | tgc | acg | tgt | 390 |
| Gly | Asp | Pro | Val | Lys | Pro | Ser | Arg | Gly | Pro | Leu | Val | Thr | Cys | Thr | Cys |  |
|  |  |  | 25 |  |  |  |  | 30 |  |  |  |  | 35 |  |  |  |

| gag | agc | cca | cat | tgc | aag | ggg | cct | acc | tgc | cgg | ggg | gcc | tgg | tgc | aca | 438 |
| Glu | Ser | Pro | His | Cys | Lys | Gly | Pro | Thr | Cys | Arg | Gly | Ala | Trp | Cys | Thr |  |
|  |  |  | 40 |  |  |  |  | 45 |  |  |  |  | 50 |  |  |  |

| gta | gtg | ctg | gtg | cgg | gag | gag | ggg | agg | cac | ccc | cag | gaa | cat | cgg | ggc | 486 |
| Val | Val | Leu | Val | Arg | Glu | Glu | Gly | Arg | His | Pro | Gln | Glu | His | Arg | Gly |  |

-continued

```
            55                  60                  65
tgc ggg aac ttg cac agg gag ctc tgc agg ggg cgc ccc acc gag ttc    534
Cys Gly Asn Leu His Arg Glu Leu Cys Arg Gly Arg Pro Thr Glu Phe
         70                  75                  80 gtc aac cac tac tgc tgc gac agc cac ctc tgc aac cac aac gtg tcc    582
Val Asn His Tyr Cys Cys Asp Ser His Leu Cys Asn His Asn Val Ser
 85                  90                  95                 100 ctg gtg ctg gag gcc acc caa cct cct tcg gag cag ccg gga aca gat    630
Leu Val Leu Glu Ala Thr Gln Pro Pro Ser Glu Gln Pro Gly Thr Asp
                    105                 110                 115 ggc cag ctg gcc ctg atc ctg ggc ccc gtg ctg gcc ttg ctg gcc ctg    678
Gly Gln Leu Ala Leu Ile Leu Gly Pro Val Leu Ala Leu Leu Ala Leu
                120                 125                 130 gtg gcc ctg ggt gtc ctg ggc ctg tgg cat gtc cga cgg agg cag gag    726
Val Ala Leu Gly Val Leu Gly Leu Trp His Val Arg Arg Arg Gln Glu
            135                 140                 145 aag cag cgt ggc ctg cac agc gag ctg gga gag tcc agt ctc atc ctg    774
Lys Gln Arg Gly Leu His Ser Glu Leu Gly Glu Ser Ser Leu Ile Leu
        150                 155                 160 aaa gca tct gag cag ggc gac acg atg ttg ggg gac ctc ctg gac agt    822
Lys Ala Ser Glu Gln Gly Asp Thr Met Leu Gly Asp Leu Leu Asp Ser
165                 170                 175                 180 gac tgc acc aca ggg agt ggc tca ggg ctc ccc ttc ctg gtg cag agg    870
Asp Cys Thr Thr Gly Ser Gly Ser Gly Leu Pro Phe Leu Val Gln Arg
                    185                 190                 195 aca gtg gca cgg cag gtt gcc ttg gtg gag tgt gtg gga aaa ggc cgc    918
Thr Val Ala Arg Gln Val Ala Leu Val Glu Cys Val Gly Lys Gly Arg
                200                 205                 210 tat ggc gaa gtg tgg cgg ggc ttg tgg cac ggt gag agt gtg gcc gtc    966
Tyr Gly Glu Val Trp Arg Gly Leu Trp His Gly Glu Ser Val Ala Val
            215                 220                 225 aag atc ttc tcc tcg agg gat gaa cag tcc tgg ttc cgg gag act gag   1014
Lys Ile Phe Ser Ser Arg Asp Glu Gln Ser Trp Phe Arg Glu Thr Glu
        230                 235                 240 atc tat aac aca gta ttg ctc aga cac gac aac atc cta ggc ttc atc   1062
Ile Tyr Asn Thr Val Leu Leu Arg His Asp Asn Ile Leu Gly Phe Ile
245                 250                 255                 260 gcc tca gac atg acc tcc cgc aac tcg agc acg cag ctg tgg ctc atc   1110
Ala Ser Asp Met Thr Ser Arg Asn Ser Ser Thr Gln Leu Trp Leu Ile
                    265                 270                 275 acg cac tac cac gag cac ggc tcc ctc tac gac ttt ctg cag aga cag   1158
Thr His Tyr His Glu His Gly Ser Leu Tyr Asp Phe Leu Gln Arg Gln
                280                 285                 290 acg ctg gag ccc cat ctg gct ctg agg cta gct gtg tcc gcg gca tgc   1206
Thr Leu Glu Pro His Leu Ala Leu Arg Leu Ala Val Ser Ala Ala Cys
            295                 300                 305 ggc ctg gcg cac ctg cac gtg gag atc ttc ggt aca cag ggc aaa cca   1254
Gly Leu Ala His Leu His Val Glu Ile Phe Gly Thr Gln Gly Lys Pro
        310                 315                 320 gcc att gcc cac cgc gac ttc aag agc cgc aat gtg ctg gtc aag agc   1302
Ala Ile Ala His Arg Asp Phe Lys Ser Arg Asn Val Leu Val Lys Ser
325                 330                 335                 340 aac ctg cag tgt tgc atc gcc gac ctg ggc ctg gct gtg atg cac tca   1350
Asn Leu Gln Cys Cys Ile Ala Asp Leu Gly Leu Ala Val Met His Ser
                    345                 350                 355 cag ggc agc gat tac ctg gac atc ggc aac aac ccg aga gtg ggc acc   1398
Gln Gly Ser Asp Tyr Leu Asp Ile Gly Asn Asn Pro Arg Val Gly Thr
                360                 365                 370 aag cgg tac atg gca ccc gag gtg ctg gac gag cag atc cgc acg gac   1446
Lys Arg Tyr Met Ala Pro Glu Val Leu Asp Glu Gln Ile Arg Thr Asp
```

```
                375                 380                 385
tgc ttt gag tcc tac aag tgg act gac atc tgg gcc ttt ggc ctg gtg      1494
Cys Phe Glu Ser Tyr Lys Trp Thr Asp Ile Trp Ala Phe Gly Leu Val
    390                 395                 400 ctg tgg gag att gcc cgc cgg acc atc gtg aat ggc atc gtg gag gac      1542
Leu Trp Glu Ile Ala Arg Arg Thr Ile Val Asn Gly Ile Val Glu Asp
405                 410                 415                 420 tat aga cca ccc ttc tat gat gtg gtg ccc aat gac ccc agc ttt gag      1590
Tyr Arg Pro Pro Phe Tyr Asp Val Val Pro Asn Asp Pro Ser Phe Glu
                425                 430                 435 gac atg aag aag gtg gtg tgt gtg gat cag cag acc ccc acc atc cct      1638
Asp Met Lys Lys Val Val Cys Val Asp Gln Gln Thr Pro Thr Ile Pro
            440                 445                 450 aac cgg ctg gct gca gac ccg gtc ctc tca ggc cta gct cag atg atg      1686
Asn Arg Leu Ala Ala Asp Pro Val Leu Ser Gly Leu Ala Gln Met Met
        455                 460                 465 cgg gag tgc tgg tac cca aac ccc tct gcc cga ctc acc gcg ctg cgg      1734
Arg Glu Cys Trp Tyr Pro Asn Pro Ser Ala Arg Leu Thr Ala Leu Arg
    470                 475                 480 atc aag aag aca cta caa aaa att agc aac agt cca gag aag cct aaa      1782
Ile Lys Lys Thr Leu Gln Lys Ile Ser Asn Ser Pro Glu Lys Pro Lys
485                 490                 495                 500 gtg att caa tag cccaggagca cctgattcct ttctgcctgc aggggggctgg         1834
Val Ile Gln gggggtgggg ggcagtggat ggtgccctat ctgggtagag gtagtgtgag tgtggtgtgt    1894
gctggggatg ggcagctgcg cctgcctgct cggcccccag cccacccagc caaaaataca    1954
gctgggctga aacctg                                                    1970

<210> SEQ ID NO 3
<211> LENGTH: 1547
<212> TYPE: DNA
<213> ORGANISM: Homo sapiens
<220> FEATURE:
<221> NAME/KEY: CDS
<222> LOCATION: (324)..(1514)

<400> SEQUENCE: 3
ggggacttct tgaacttgca gggagaataa cttgcgcacc ccactttgcg ccggtgcctt      60
tgccccagcg gagcctgctt cgccatctcc gagccccacc gccctccac tcctcggcct     120 tgcccgacac tgagacgctg ttcccagcgt gaaaagagag actgcgcggc cggcacccgg    180
gagaaggagg aggcaaagaa aaggaacgga cattcggtcc ttgcgccagg tcctttgacc    240
agagtttttc catgtggacg ctctttcaat ggacgtgtcc ccgcgtgctt cttagacgga    300
ctgcggtctc ctaaaggtcg acc atg gtg gcc ggg acc cgc tgt ctt cta gcg    353
                            Met Val Ala Gly Thr Arg Cys Leu Leu Ala
                             1               5                  10 ttg ctg ctt ccc cag gtc ctc ctg ggc ggc gcg gct ggc ctc gtt ccg       401
Leu Leu Leu Pro Gln Val Leu Leu Gly Gly Ala Ala Gly Leu Val Pro
                15                  20                  25 gag ctg ggc cgc agg aag ttc gcg gcg gcg tcg tcg ggc cgc ccc tca       449
Glu Leu Gly Arg Arg Lys Phe Ala Ala Ala Ser Ser Gly Arg Pro Ser
            30                  35                  40 tcc cag ccc tct gac gag gtc ctg agc gag ttc gag ttg cgg ctg ctc       497
Ser Gln Pro Ser Asp Glu Val Leu Ser Glu Phe Glu Leu Arg Leu Leu
        45                  50                  55 agc atg ttc ggc ctg aaa cag aga ccc acc ccc agc agg gac gcc gtg       545
Ser Met Phe Gly Leu Lys Gln Arg Pro Thr Pro Ser Arg Asp Ala Val
    60                  65                  70
```

```
gtg ccc ccc tac atg cta gac ctg tat cgc agg cac tca ggt cag ccg     593
Val Pro Pro Tyr Met Leu Asp Leu Tyr Arg Arg His Ser Gly Gln Pro
 75              80              85              90 ggc tca ccc gcc cca gac cac cgg ttg gag agg gca gcc agc cga gcc     641
Gly Ser Pro Ala Pro Asp His Arg Leu Glu Arg Ala Ala Ser Arg Ala
                 95             100             105 aac act gtg cgc agc ttc cac cat gaa gaa tct ttg gaa gaa cta cca     689
Asn Thr Val Arg Ser Phe His His Glu Glu Ser Leu Glu Glu Leu Pro
            110             115             120 gaa acg agt ggg aaa aca acc cgg aga ttc ttc ttt aat tta agt tct     737
Glu Thr Ser Gly Lys Thr Thr Arg Arg Phe Phe Phe Asn Leu Ser Ser
        125             130             135 atc ccc acg gag gag ttt atc acc tca gca gag ctt cag gtt ttc cga     785
Ile Pro Thr Glu Glu Phe Ile Thr Ser Ala Glu Leu Gln Val Phe Arg
140             145             150 gaa cag atg caa gat gct tta gga aac aat agc agt ttc cat cac cga     833
Glu Gln Met Gln Asp Ala Leu Gly Asn Asn Ser Ser Phe His His Arg
155             160             165             170 att aat att tat gaa atc ata aaa cct gca aca gcc aac tcg aaa ttc     881
Ile Asn Ile Tyr Glu Ile Ile Lys Pro Ala Thr Ala Asn Ser Lys Phe
                175             180             185 ccc gtg acc aga ctt ttg gac acc agg ttg gtg aat cag aat gca agc     929
Pro Val Thr Arg Leu Leu Asp Thr Arg Leu Val Asn Gln Asn Ala Ser
            190             195             200 agg tgg gaa agt ttt gat gtc acc ccc gct gtg atg cgg tgg act gca     977
Arg Trp Glu Ser Phe Asp Val Thr Pro Ala Val Met Arg Trp Thr Ala
        205             210             215 cag gga cac gcc aac cat gga ttc gtg gtg gaa gtg gcc cac ttg gag    1025
Gln Gly His Ala Asn His Gly Phe Val Val Glu Val Ala His Leu Glu
220             225             230 gag aaa caa ggt gtc tcc aag aga cat gtt agg ata agc agg tct ttg    1073
Glu Lys Gln Gly Val Ser Lys Arg His Val Arg Ile Ser Arg Ser Leu
235             240             245             250 cac caa gat gaa cac agc tgg tca cag ata agg cca ttg cta gta act    1121
His Gln Asp Glu His Ser Trp Ser Gln Ile Arg Pro Leu Leu Val Thr
                255             260             265 ttt ggc cat gat gga aaa ggg cat cct ctc cac aaa aga gaa aaa cgt    1169
Phe Gly His Asp Gly Lys Gly His Pro Leu His Lys Arg Glu Lys Arg
            270             275             280 caa gcc aaa cac aaa cag cgg aaa cgc ctt aag tcc agc tgt aag aga    1217
Gln Ala Lys His Lys Gln Arg Lys Arg Leu Lys Ser Ser Cys Lys Arg
        285             290             295 cac cct ttg tac gtg gac ttc agt gac gtg ggg tgg aat gac tgg att    1265
His Pro Leu Tyr Val Asp Phe Ser Asp Val Gly Trp Asn Asp Trp Ile
300             305             310 gtg gct ccc ccg ggg tat cac gcc ttt tac tgc cac gga gaa tgc cct    1313
Val Ala Pro Pro Gly Tyr His Ala Phe Tyr Cys His Gly Glu Cys Pro
315             320             325             330 ttt cct ctg gct gat cat ctg aac tcc act aat cat gcc att gtt cag    1361
Phe Pro Leu Ala Asp His Leu Asn Ser Thr Asn His Ala Ile Val Gln
                335             340             345 acg ttg gtc aac tct gtt aac tct aag att cct aag gca tgc tgt gtc    1409
Thr Leu Val Asn Ser Val Asn Ser Lys Ile Pro Lys Ala Cys Cys Val
            350             355             360 ccg aca gaa ctc agt gct atc tcg atg ctg tac ctt gac gag aat gaa    1457
Pro Thr Glu Leu Ser Ala Ile Ser Met Leu Tyr Leu Asp Glu Asn Glu
        365             370             375 aag gtt gta tta aag aac tat cag gac atg gtt gtg gag ggt tgt ggg    1505
Lys Val Val Leu Lys Asn Tyr Gln Asp Met Val Val Glu Gly Cys Gly
380             385             390
```

```
tgt cgc tag tacagcaaaa ttaaatacat aaatatatat ata         1547
Cys Arg
395

<210> SEQ ID NO 4
<211> LENGTH: 1999
<212> TYPE: DNA
<213> ORGANISM: Homo sapiens
<220> FEATURE:
<221> NAME/KEY: CDS
<222> LOCATION: (478)..(1704)

<400> SEQUENCE: 4
gagggagggg ccgccgggga agaggaggag gaaggaaaga aagaaagcga gggagggaaa     60
gaggaggaag gaagatgcga gaaggcagag gaggagggag ggaggggaagg agcgcggagc   120 ccggcccgga agctaggtga gtgtggcatc cgagctgagg gacgcgagcc tgagacgccg   180
ctgctgctcc ggctgagtat ctagcttgtc tccccgatgg gattcccgtc caagctatct   240
cgagcctgca gcgccacagt ccccggccct cgcccaggtt cactgcaacc gttcagaggt   300
ccccaggagc tgctgctggc gagcccgcta ctgcagggac ctatggagcc attccgtagt   360
gccatcccga gcaacgcact gctgcagctt ccctgagcct ttccagcaag tttgttcaag   420
attggctgtc aagaatcatg gactgttatt atatgccttg ttttctgtca agacacc      477 atg att cct ggt aac cga atg ctg atg gtc gtt tta tta tgc caa gtc    525
Met Ile Pro Gly Asn Arg Met Leu Met Val Val Leu Leu Cys Gln Val
1               5                   10                  15 ctg cta gga ggc gcg agc cat gct agt ttg ata cct gag acg ggg aag    573
Leu Leu Gly Gly Ala Ser His Ala Ser Leu Ile Pro Glu Thr Gly Lys
            20                  25                  30 aaa aaa gtc gcc gag att cag ggc cac gcg gga gga cgc cgc tca ggg    621
Lys Lys Val Ala Glu Ile Gln Gly His Ala Gly Gly Arg Arg Ser Gly
35                  40                  45 cag agc cat gag ctc ctg cgg gac ttc gag gcg aca ctt ctg cag atg    669
Gln Ser His Glu Leu Leu Arg Asp Phe Glu Ala Thr Leu Leu Gln Met
    50                  55                  60 ttt ggg ctg cgc cgc cgc ccg cag cct agc aag agt gcc gtc att ccg    717
Phe Gly Leu Arg Arg Arg Pro Gln Pro Ser Lys Ser Ala Val Ile Pro
65                  70                  75                  80 gac tac atg cgg gat ctt tac cgg ctt cag tct ggg gag gag gag gaa    765
Asp Tyr Met Arg Asp Leu Tyr Arg Leu Gln Ser Gly Glu Glu Glu Glu
                85                  90                  95 gag cag atc cac agc act ggt ctt gag tat cct gag cgc ccg gcc agc    813
Glu Gln Ile His Ser Thr Gly Leu Glu Tyr Pro Glu Arg Pro Ala Ser
            100                 105                 110 cgg gcc aac acc gtg agg agc ttc cac cac gaa gaa cat ctg gag aac    861
Arg Ala Asn Thr Val Arg Ser Phe His His Glu Glu His Leu Glu Asn
        115                 120                 125 atc cca ggg acc agt gaa aac tct gct ttt cgt ttc ctc ttt aac ctc    909
Ile Pro Gly Thr Ser Glu Asn Ser Ala Phe Arg Phe Leu Phe Asn Leu
    130                 135                 140 agc agc atc cct gag aac gag gcg atc tcc tct gca gag ctt cgg ctc    957
Ser Ser Ile Pro Glu Asn Glu Ala Ile Ser Ser Ala Glu Leu Arg Leu
145                 150                 155                 160 ttc cgg gag cag gtg gac cag ggc cct gat tgg gaa agg ggc ttc cac   1005
Phe Arg Glu Gln Val Asp Gln Gly Pro Asp Trp Glu Arg Gly Phe His
                165                 170                 175 cgt ata aac att tat gag gtt atg aag ccc cca gca gaa gtg gtg cct   1053
Arg Ile Asn Ile Tyr Glu Val Met Lys Pro Pro Ala Glu Val Val Pro
            180                 185                 190 ggg cac ctc atc aca cga cta ctg gac acg aga ctg gtc cac cac aat   1101
```

```
                Gly His Leu Ile Thr Arg Leu Leu Asp Thr Arg Leu Val His His Asn
                    195                 200                 205 gtg aca cgg tgg gaa act ttt gat gtg agc cct gcg gtc ctt cgc tgg      1149
Val Thr Arg Trp Glu Thr Phe Asp Val Ser Pro Ala Val Leu Arg Trp
210                 215                 220 acc cgg gag aag cag cca aac tat ggg cta gcc att gag gtg act cac      1197
Thr Arg Glu Lys Gln Pro Asn Tyr Gly Leu Ala Ile Glu Val Thr His
225                 230                 235                 240 ctc cat cag act cgg acc cac cag ggc cag cat gtc agg att agc cga      1245
Leu His Gln Thr Arg Thr His Gln Gly Gln His Val Arg Ile Ser Arg
                245                 250                 255 tcg tta cct caa ggg agt ggg aat tgg gcc cag ctc cgg ccc ctc ctg      1293
Ser Leu Pro Gln Gly Ser Gly Asn Trp Ala Gln Leu Arg Pro Leu Leu
            260                 265                 270 gtc acc ttt ggc cat gat ggc cgg ggc cat gcc ttg acc cga cgc cgg      1341
Val Thr Phe Gly His Asp Gly Arg Gly His Ala Leu Thr Arg Arg Arg
        275                 280                 285 agg gcc aag cgt agc cct aag cat cac tca cag cgg gcc agg aag aag      1389
Arg Ala Lys Arg Ser Pro Lys His His Ser Gln Arg Ala Arg Lys Lys
    290                 295                 300 aat aag aac tgc cgg cgc cac tcg ctc tat gtg gac ttc agc gat gtg      1437
Asn Lys Asn Cys Arg Arg His Ser Leu Tyr Val Asp Phe Ser Asp Val
305                 310                 315                 320 ggc tgg aat gac tgg att gtg gcc cca cca ggc tac cag gcc ttc tac      1485
Gly Trp Asn Asp Trp Ile Val Ala Pro Pro Gly Tyr Gln Ala Phe Tyr
                325                 330                 335 tgc cat ggg gac tgc ccc ttt cca ctg gct gac cac ctc aac tca acc      1533
Cys His Gly Asp Cys Pro Phe Pro Leu Ala Asp His Leu Asn Ser Thr
            340                 345                 350 aac cat gcc att gtg cag acc ctg gtc aat tct gtc aat tcc agt atc      1581
Asn His Ala Ile Val Gln Thr Leu Val Asn Ser Val Asn Ser Ser Ile
        355                 360                 365 ccc aaa gcc tgt tgt gtg ccc act gaa ctg agt gcc atc tcc atg ctg      1629
Pro Lys Ala Cys Cys Val Pro Thr Glu Leu Ser Ala Ile Ser Met Leu
    370                 375                 380 tac ctg gat gag tat gat aag gtg gta ctg aaa aat tat cag gag atg      1677
Tyr Leu Asp Glu Tyr Asp Lys Val Val Leu Lys Asn Tyr Gln Glu Met
385                 390                 395                 400 gta gta gag gga tgt ggg tgc cgc tga gatcaggcag tccttgagga            1724
Val Val Glu Gly Cys Gly Cys Arg
                405 tagacagata tacacaccac acacacacac cacatacacc acacacacac gttcccatcc    1784 actcacccac acactacaca gactgcttcc ttatagctgg acttttattt aaaaaaaaaa    1844 aaaaaaaaat ggaaaaaatc cctaaacatt caccttgacc ttatttatga ctttacgtgc    1904 aaatgttttg accatattga tcatatattt tgacaaaata tatttataac tacgtattaa    1964 aagaaaaaaa taaatgagt cattatttta aaggt                               1999

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
actaccacca cggctttcac                                                  20

<210> SEQ ID NO 6
```

```
-continued

<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aataggattg tggggtgagc                                                 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccgtcaagat cttctcctcg                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcatgtctga ggcgatgaag                                                 20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cccagcgtga aaagagagac                                                 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gagaccgcag tccgtctaag                                                 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgagcctttc cagcaagttt                                                 20

<210> SEQ ID NO 12
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 12
cttccccgtc tcaggtatca                                               20

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
caagctggtc acattcatag cggct                                         25

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ttcctcccct tggaggagcg ccgcccg                                       27

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggagctcccc aatttgttg                                                19

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cagcctccgc ctcttacc                                                 18

<210> SEQ ID NO 17
<211> LENGTH: 262
<212> TYPE: DNA
<213> ORGANISM: Mus musculus

<400> SEQUENCE: 17
cccaccaccg tctgcaagat ccccagcggg tgcagcttga aaatcttcaa caaccaagag    60
tttgctcagc tactggcgca gtctgtgaac cacgggttcg agaccgtgta tgaactcacc   120
aaaatgtgca ctattcggat gagcttcgtg aagggttggg gagccgaata ccaccggcag   180
gatgttacca gcaccccctg ctggattgag atccatctgc atggccctct ccagtggctg   240
gataaggttc tgacccagat gg                                           262
```

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
catgctcgtc acattcaaag ccgct                                          25

<210> SEQ ID NO 19
<211> LENGTH: 4978
<212> TYPE: DNA
<213> ORGANISM: Homo sapiens
<220> FEATURE:
<221> NAME/KEY: CDS
<222> LOCATION: (241)..(2553)

<400> SEQUENCE: 19
ggtttccgga gctgcggcgg cgcagactgg gaggggagc cggggttcc gacgtcgcag        60 ccgagggaac aagccccaac cggatcctgg acaggcaccc cggcttggcg ctgtctctcc     120
ccctcggctc ggagaggccc ttcggcctga gggagcctcg ccgcccgtcc ccggcacacg     180
cgcagccccg gcctctcggc tctgccggga gaaacagttg ggaccccctga ttttagcagg    240 atg gcc caa tgg aat cag cta cag cag ctt gac aca cgg tac ctg gag      288
Met Ala Gln Trp Asn Gln Leu Gln Gln Leu Asp Thr Arg Tyr Leu Glu
 1               5                   10                  15 cag ctc cat cag ctc tac agt gac agc ttc cca atg gag ctg cgg cag      336
Gln Leu His Gln Leu Tyr Ser Asp Ser Phe Pro Met Glu Leu Arg Gln
             20                  25                  30 ttt ctg gcc cct tgg att gag agt caa gat tgg gca tat gcg gcc agc      384
Phe Leu Ala Pro Trp Ile Glu Ser Gln Asp Trp Ala Tyr Ala Ala Ser
         35                  40                  45 aaa gaa tca cat gcc act ttg gtg ttt cat aat ctc ctg gga gag att      432
Lys Glu Ser His Ala Thr Leu Val Phe His Asn Leu Leu Gly Glu Ile
     50                  55                  60 gac cag cag tat agc cgc ttc ctg caa gag tcg aat gtt ctc tat cag      480
Asp Gln Gln Tyr Ser Arg Phe Leu Gln Glu Ser Asn Val Leu Tyr Gln
 65                  70                  75                  80 cac aat cta cga aga atc aag cag ttt ctt cag agc agg tat ctt gag      528
His Asn Leu Arg Arg Ile Lys Gln Phe Leu Gln Ser Arg Tyr Leu Glu
                 85                  90                  95 aag cca atg gag att gcc cgg att gtg gcc cgg tgc ctg tgg gaa gaa      576
Lys Pro Met Glu Ile Ala Arg Ile Val Ala Arg Cys Leu Trp Glu Glu
            100                 105                 110 tca cgc ctt cta cag act gca gcc act gcg gcc cag caa ggg ggc cag      624
Ser Arg Leu Leu Gln Thr Ala Ala Thr Ala Ala Gln Gln Gly Gly Gln
        115                 120                 125 gcc aac cac ccc aca gca gcc gtg gtg acg gag aag cag cag atg ctg      672
Ala Asn His Pro Thr Ala Ala Val Val Thr Glu Lys Gln Gln Met Leu
    130                 135                 140 gag cag cac ctt cag gat gtc cgg aag aga gtg cag gat cta gaa cag      720
Glu Gln His Leu Gln Asp Val Arg Lys Arg Val Gln Asp Leu Glu Gln
145                 150                 155                 160 aaa atg aaa gtg gta gag aat ctc cag gat gac ttt gat ttc aac tat      768
Lys Met Lys Val Val Glu Asn Leu Gln Asp Asp Phe Asp Phe Asn Tyr
                165                 170                 175 aaa acc ctc aag agt caa gga gac atg caa gat ctg aat gga aac aac      816
Lys Thr Leu Lys Ser Gln Gly Asp Met Gln Asp Leu Asn Gly Asn Asn
            180                 185                 190 cag tca gtg acc agg cag aag atg cag cag ctg gaa cag atg ctc act      864

```
              Gln Ser Val Thr Arg Gln Lys Met Gln Gln Leu Glu Gln Met Leu Thr
                      195                 200                 205 gcg ctg gac cag atg cgg aga agc atc gtg agt gag ctg gcg ggg ctt          912
Ala Leu Asp Gln Met Arg Arg Ser Ile Val Ser Glu Leu Ala Gly Leu
210                 215                 220 ttg tca gcg atg gag tac gtg cag aaa act ctc acg gac gag gag ctg          960
Leu Ser Ala Met Glu Tyr Val Gln Lys Thr Leu Thr Asp Glu Glu Leu
225                 230                 235                 240 gct gac tgg aag agg cgg caa cag att gcc tgc att gga ggc ccg ccc         1008
Ala Asp Trp Lys Arg Arg Gln Gln Ile Ala Cys Ile Gly Gly Pro Pro
                245                 250                 255 aac atc tgc cta gat cgg cta gaa aac tgg ata acg tca tta gca gaa         1056
Asn Ile Cys Leu Asp Arg Leu Glu Asn Trp Ile Thr Ser Leu Ala Glu
            260                 265                 270 tct caa ctt cag acc cgt caa caa att aag aaa ctg gag gag ttg cag         1104
Ser Gln Leu Gln Thr Arg Gln Gln Ile Lys Lys Leu Glu Glu Leu Gln
        275                 280                 285 caa aaa gtt tcc tac aaa ggg gac ccc att gta cag cac cgg ccg atg         1152
Gln Lys Val Ser Tyr Lys Gly Asp Pro Ile Val Gln His Arg Pro Met
    290                 295                 300 ctg gag gag aga atc gtg gag ctg ttt aga aac tta atg aaa agt gcc         1200
Leu Glu Glu Arg Ile Val Glu Leu Phe Arg Asn Leu Met Lys Ser Ala
305                 310                 315                 320 ttt gtg gtg gag cgg cag ccc tgc atg ccc atg cat cct gac cgg ccc         1248
Phe Val Val Glu Arg Gln Pro Cys Met Pro Met His Pro Asp Arg Pro
                325                 330                 335 ctc gtc atc aag acc ggc gtc cag ttc act act aaa gtc agg ttg ctg         1296
Leu Val Ile Lys Thr Gly Val Gln Phe Thr Thr Lys Val Arg Leu Leu
            340                 345                 350 gtc aaa ttc cct gag ttg aat tat cag ctt aaa att aaa gtg tgc att         1344
Val Lys Phe Pro Glu Leu Asn Tyr Gln Leu Lys Ile Lys Val Cys Ile
        355                 360                 365 gac aaa gac tct ggg gac gtt gca gct ctc aga gga tcc cgg aaa ttt         1392
Asp Lys Asp Ser Gly Asp Val Ala Ala Leu Arg Gly Ser Arg Lys Phe
    370                 375                 380 aac att ctg ggc aca aac aca aaa gtg atg aac atg gaa gaa tcc aac         1440
Asn Ile Leu Gly Thr Asn Thr Lys Val Met Asn Met Glu Glu Ser Asn
385                 390                 395                 400 aac ggc agc ctc tct gca gaa ttc aaa cac ttg acc ctg agg gag cag         1488
Asn Gly Ser Leu Ser Ala Glu Phe Lys His Leu Thr Leu Arg Glu Gln
                405                 410                 415 aga tgt ggg aat ggg ggc cga gcc aat tgt gat gct tcc ctg att gtg         1536
Arg Cys Gly Asn Gly Gly Arg Ala Asn Cys Asp Ala Ser Leu Ile Val
            420                 425                 430 act gag gag ctg cac ctg atc acc ttt gag acc gag gtg tat cac caa         1584
Thr Glu Glu Leu His Leu Ile Thr Phe Glu Thr Glu Val Tyr His Gln
        435                 440                 445 ggc ctc aag att gac cta gag acc cac tcc ttg cca gtt gtg gtg atc         1632
Gly Leu Lys Ile Asp Leu Glu Thr His Ser Leu Pro Val Val Val Ile
    450                 455                 460 tcc aac atc tgt cag atg cca aat gcc tgg gcg tcc atc ctg tgg tac         1680
Ser Asn Ile Cys Gln Met Pro Asn Ala Trp Ala Ser Ile Leu Trp Tyr
465                 470                 475                 480 aac atg ctg acc aac aat ccc aag aat gta aac ttt ttt acc aag ccc         1728
Asn Met Leu Thr Asn Asn Pro Lys Asn Val Asn Phe Phe Thr Lys Pro
                485                 490                 495 cca att gga acc tgg gat caa gtg gcc gag gtc ctg agc tgg cag ttc         1776
Pro Ile Gly Thr Trp Asp Gln Val Ala Glu Val Leu Ser Trp Gln Phe
            500                 505                 510 tcc tcc acc acc aag cga gga ctg agc atc gag cag ctg act aca ctg         1824
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Ser | Ser | Thr | Thr | Lys | Arg | Gly | Leu | Ser | Ile | Glu | Gln | Leu | Thr | Thr | Leu |      |
|     |     | 515 |     |     |     |     | 520 |     |     |     |     | 525 |     |     |     |      |
| gca | gag | aaa | ctc | ttg | gga | cct | ggt | gtg | aat | tat | tca | ggg | tgt | cag | atc | 1872 |
| Ala | Glu | Lys | Leu | Leu | Gly | Pro | Gly | Val | Asn | Tyr | Ser | Gly | Cys | Gln | Ile |      |
|     | 530 |     |     |     |     | 535 |     |     |     |     | 540 |     |     |     |     |      |
| aca | tgg | gct | aaa | ttt | tgc | aaa | gaa | aac | atg | gct | ggc | aag | ggc | ttc | tcc | 1920 |
| Thr | Trp | Ala | Lys | Phe | Cys | Lys | Glu | Asn | Met | Ala | Gly | Lys | Gly | Phe | Ser |      |
| 545 |     |     |     | 550 |     |     |     |     | 555 |     |     |     |     | 560 |     |      |
| ttc | tgg | gtc | tgg | ctg | gac | aat | atc | att | gac | ctt | gtg | aaa | aag | tac | atc | 1968 |
| Phe | Trp | Val | Trp | Leu | Asp | Asn | Ile | Ile | Asp | Leu | Val | Lys | Lys | Tyr | Ile |      |
|     |     |     | 565 |     |     |     |     | 570 |     |     |     |     | 575 |     |     |      |
| ctg | gcc | ctt | tgg | aac | gaa | ggg | tac | atc | atg | ggc | ttt | atc | agt | aag | gag | 2016 |
| Leu | Ala | Leu | Trp | Asn | Glu | Gly | Tyr | Ile | Met | Gly | Phe | Ile | Ser | Lys | Glu |      |
|     |     | 580 |     |     |     |     | 585 |     |     |     |     | 590 |     |     |     |      |
| cgg | gag | cgg | gcc | atc | ttg | agc | act | aag | cct | cca | ggc | acc | ttc | ctg | cta | 2064 |
| Arg | Glu | Arg | Ala | Ile | Leu | Ser | Thr | Lys | Pro | Pro | Gly | Thr | Phe | Leu | Leu |      |
| 595 |     |     |     |     | 600 |     |     |     |     | 605 |     |     |     |     |     |      |
| aga | ttc | agt | gaa | agc | agc | aaa | gaa | gga | ggc | gtc | act | ttc | act | tgg | gtg | 2112 |
| Arg | Phe | Ser | Glu | Ser | Ser | Lys | Glu | Gly | Gly | Val | Thr | Phe | Thr | Trp | Val |      |
|     | 610 |     |     |     |     | 615 |     |     |     |     | 620 |     |     |     |     |      |
| gag | aag | gac | atc | agc | ggt | aag | acc | cag | atc | cag | tcc | gtg | gaa | cca | tac | 2160 |
| Glu | Lys | Asp | Ile | Ser | Gly | Lys | Thr | Gln | Ile | Gln | Ser | Val | Glu | Pro | Tyr |      |
| 625 |     |     |     | 630 |     |     |     |     | 635 |     |     |     |     | 640 |     |      |
| aca | aag | cag | cag | ctg | aac | aac | atg | tca | ttt | gct | gaa | atc | atc | atg | ggc | 2208 |
| Thr | Lys | Gln | Gln | Leu | Asn | Asn | Met | Ser | Phe | Ala | Glu | Ile | Ile | Met | Gly |      |
|     |     |     | 645 |     |     |     |     | 650 |     |     |     |     | 655 |     |     |      |
| tat | aag | atc | atg | gat | gct | acc | aat | atc | ctg | gtg | tct | cca | ctg | gtc | tat | 2256 |
| Tyr | Lys | Ile | Met | Asp | Ala | Thr | Asn | Ile | Leu | Val | Ser | Pro | Leu | Val | Tyr |      |
|     |     | 660 |     |     |     |     | 665 |     |     |     |     | 670 |     |     |     |      |
| ctc | tat | cct | gac | att | ccc | aag | gag | gag | gca | ttc | gga | aag | tat | tgt | cgg | 2304 |
| Leu | Tyr | Pro | Asp | Ile | Pro | Lys | Glu | Glu | Ala | Phe | Gly | Lys | Tyr | Cys | Arg |      |
|     |     | 675 |     |     |     |     | 680 |     |     |     |     | 685 |     |     |     |      |
| cca | gag | agc | cag | gag | cat | cct | gaa | gct | gac | cca | ggt | agc | gct | gcc | cca | 2352 |
| Pro | Glu | Ser | Gln | Glu | His | Pro | Glu | Ala | Asp | Pro | Gly | Ser | Ala | Ala | Pro |      |
|     | 690 |     |     |     |     | 695 |     |     |     |     | 700 |     |     |     |     |      |
| tac | ctg | aag | acc | aag | ttt | atc | tgt | gtg | aca | cca | acg | acc | tgc | agc | aat | 2400 |
| Tyr | Leu | Lys | Thr | Lys | Phe | Ile | Cys | Val | Thr | Pro | Thr | Thr | Cys | Ser | Asn |      |
| 705 |     |     |     | 710 |     |     |     |     | 715 |     |     |     |     | 720 |     |      |
| acc | att | gac | ctg | ccg | atg | tcc | ccc | cgc | act | tta | gat | tca | ttg | atg | cag | 2448 |
| Thr | Ile | Asp | Leu | Pro | Met | Ser | Pro | Arg | Thr | Leu | Asp | Ser | Leu | Met | Gln |      |
|     |     |     | 725 |     |     |     |     | 730 |     |     |     |     | 735 |     |     |      |
| ttt | gga | aat | aat | ggt | gaa | ggt | gct | gaa | ccc | tca | gca | gga | ggg | cag | ttt | 2496 |
| Phe | Gly | Asn | Asn | Gly | Glu | Gly | Ala | Glu | Pro | Ser | Ala | Gly | Gly | Gln | Phe |      |
|     |     | 740 |     |     |     |     | 745 |     |     |     |     | 750 |     |     |     |      |
| gag | tcc | ctc | acc | ttt | gac | atg | gag | ttg | acc | tcg | gag | tgc | gct | acc | tcc | 2544 |
| Glu | Ser | Leu | Thr | Phe | Asp | Met | Glu | Leu | Thr | Ser | Glu | Cys | Ala | Thr | Ser |      |
|     |     | 755 |     |     |     |     | 760 |     |     |     |     | 765 |     |     |     |      |
| ccc | atg | tga | ggagctgaga | acggaagctg | cagaaagata | cgactgaggc |     |     |     |     |     |     |     |     |     | 2593 |
| Pro | Met |     |            |            |            |            |     |     |     |     |     |     |     |     |     |      |
|     | 770 |     |            |            |            |            |     |     |     |     |     |     |     |     |     |      |

| | |
| --- | --- |
| gcctacctgc attctgccac ccctcacaca gccaaacccc agatcatctg aaactactaa | 2653 |
| ctttgtggtt ccagattttt tttaatctcc tacttctgct atctttgagc aatctgggca | 2713 |
| cttttaaaaa tagagaaatg agtgaatgtg ggtgatctgc ttttatctaa atgcaaataa | 2773 |
| ggatgtgttc tctgagaccc atgatcaggg gatgtggcgg ggggtggcta gagggagaaa | 2833 |
| aaggaaatgt cttgtgttgt tttgttcccc tgccctcctt tctcagcagc ttttgttat | 2893 |
| tgttgttgtt gttcttagac aagtgcctcc tggtgcctgc ggcatccttc tgcctgtttc | 2953 |
| tgtaagcaaa tgccacaggc cacctatagc tacatactcc tggcattgca cttttaacc | 3013 |

```
ttgctgacat ccaaatagaa gataggacta tctaagccct aggtttcttt ttaaattaag    3073
aaataataac aattaaaggg caaaaaacac tgtatcagca tagcctttct gtatttaaga    3133
aacttaagca gccgggcatg gtggctcacg cctgtaatcc cagcactttg ggaggccgag    3193
gcggatcata aggtcaggag atcaagacca tcctggctaa cacggtgaaa ccccgtctct    3253
actaaaagta caaaaaatta gctgggtgtg gtggtgggcg cctgtagtcc cagctactcg    3313
ggaggctgag gcaggagaat cgcttgaacc tgagaggcgg aggttgcagt gagccaaaat    3373
tgcaccactg cacactgcac tccatcctgg gcgacagtct gagactctgt ctcaaaaaaa    3433
aaaaaaaaaa aagaaaactt cagttaacag cctccttggt gctttaagca ttcagcttcc    3493
ttcaggctgg taatttatat aatccctgaa acgggcttca ggtcaaaccc ttaagacatc    3553
tgaagctgca acctggcctt tggtgttgaa ataggaaggt ttaaggagaa tctaagcatt    3613
ttagactttt ttttataaat agacttattt tcctttgtaa tgtattggcc ttttagtgag    3673
taaggctggg cagagggtgc ttacaacctt gactcccttt ctccctggac ttgatctgct    3733
gtttcagagg ctaggttgtt tctgtgggtg ccttatcagg gctgggatac ttctgattct    3793
ggcttccttc ctgccccacc ctcccgaccc cagtccccct gatcctgcta gaggcatgtc    3853
tccttgcgtg tctaaaggtc cctcatcctg tttgttttag gaatcctggt ctcaggacct    3913 catgaagaa gagggggaga gagttacagg ttggacatga tgcacactat ggggcccag     3973 cgacgtgtct ggttgagctc agggaatatg gttcttagcc agtttcttgg tgatatccag    4033
tggcacttgt aatggcgtct tcattcagtt catgcagggc aaaggcttac tgataaactt    4093
gagtctgccc tcgtatgagg gtgtatacct ggcctccctc tgaggctggt gactcctccc    4153
tgctggggcc ccacaggtga ggcagaacag ctagagggcc tccccgcctg cccgccttgg    4213
ctggctagct cgcctctcct gtgcgtatgg gaacacctag cacgtgctgg atgggctgcc    4273
tctgactcag aggcatggcc ggatttggca actcaaaacc accttgcctc agctgatcag    4333
agtttctgtg gaattctgtt tgttaaatca aattagctgg tctctgaatt aaggggagaa    4393
cgaccttctc taagatgaac agggttcgcc ccagtcctcc tgcctggaga cagttgatgt    4453
gtcatgcaga gctcttactt ctccagcaac actcttcagt acataataag cttaactgat    4513
aaacagaata tttagaaagg tgagacttgg gcttaccatt gggtttaaat catagggacc    4573
tagggcgagg gttcagggct tctctggagc agatattgtc aagttcatgg ccttaggtag    4633
catgtatctg gtcttaactc tgattgtagc aaaagttctg agaggagctg agccctgttg    4693
tggcccatta aagaacaggg tcctcaggcc ctgcccgctt cctgtccact gcccctccc    4753 catcccagc ccagccgagg gaatcccgtg ggttgcttac ctacctataa ggtggtttat    4813
aagctgctgt cctggccact gcattcaaat tccaatgtgt acttcatagt gtaaaaattt    4873
atattattgt gaggtttttt gtcttttttt tttttttttt tttttggtat attgctgtat    4933
ctactttaac ttccagaaat aaacgttata taggaaccgt aaaaa              4978

<210> SEQ ID NO 20
<211> LENGTH: 3631
<212> TYPE: DNA
<213> ORGANISM: Homo sapiens
<220> FEATURE:
<221> NAME/KEY: CDS
<222> LOCATION: (549)..(2147)

<400> SEQUENCE: 20
gcggccgctg cagagattgg aatccgcctg ccgggcttgg cgaaggagaa gggaggaggc        60
```

-continued

```
aggagcgagg agggaggagg gccaagggcg ggcaggaagg cttaggctcg gcgcgtccgt    120
ccgcgcgcgg cgaagatcgc acggcccgat cgaggggcga ccgggtcggg gccgctgcac    180
gccaagggcg aaggccgatt cgggcccccac ttcgccccgg cggctcgccg cgcccacccg   240
ctccgcgccg agggctggag gatgcgttcc ctggggtccg gacttatgaa aatatgcatc    300
agtttaatac tgtcttggaa ttcatgagat ggaagcatag gtcaaagctg tttggagaaa    360
atcagaagta cagtttttatc tagccacatc ttggaggagt cgtaagaaag cagtgggagt    420
tgaagtcatt gtcaagtgct tgcgatcttt tacaagaaaa tctcactgaa tgatagtcat    480
ttaaattggt gaagtagcaa gaccaattat taaaggtgac agtacacagg aaacattaca    540
```

```
attgaaca atg cct cag cta tac att tac atc aga tta ttg gga gcc tat   590
        Met Pro Gln Leu Tyr Ile Tyr Ile Arg Leu Leu Gly Ala Tyr
          1               5                  10 ttg ttc atc att tct cgt gtt caa gga cag aat ctg gat agt atg ctt   638
Leu Phe Ile Ile Ser Arg Val Gln Gly Gln Asn Leu Asp Ser Met Leu
 15                  20                  25                  30 cat ggc act ggg atg aaa tca gac tcc gac cag aaa aag tca gaa aat   686
His Gly Thr Gly Met Lys Ser Asp Ser Asp Gln Lys Lys Ser Glu Asn
              35                  40                  45 gga gta acc tta gca cca gag gat acc ttg cct ttt tta aag tgc tat   734
Gly Val Thr Leu Ala Pro Glu Asp Thr Leu Pro Phe Leu Lys Cys Tyr
 50                  55                  60 tgc tca ggg cac tgt cca gat gat gct att aat aac aca tgc ata act   782
Cys Ser Gly His Cys Pro Asp Asp Ala Ile Asn Asn Thr Cys Ile Thr
              65                  70                  75 aat gga cat tgc ttt gcc atc ata gaa gaa gat gac cag gga gaa acc   830
Asn Gly His Cys Phe Ala Ile Ile Glu Glu Asp Asp Gln Gly Glu Thr
 80                  85                  90 aca tta gct tca ggg tgt atg aaa tat gaa gga tct gat ttt cag tgc   878
Thr Leu Ala Ser Gly Cys Met Lys Tyr Glu Gly Ser Asp Phe Gln Cys
 95                  100                 105                 110 aaa gat tct cca aaa gcc cag cta cgc cgg aca ata gaa tgt tgt cgg   926
Lys Asp Ser Pro Lys Ala Gln Leu Arg Arg Thr Ile Glu Cys Cys Arg
              115                 120                 125 acc aat tta tgt aac cag tat ttg caa ccc aca ctg ccc cct gtt gtc   974
Thr Asn Leu Cys Asn Gln Tyr Leu Gln Pro Thr Leu Pro Pro Val Val
              130                 135                 140 ata ggt ccg ttt ttt gat ggc agc att cga tgg ctg gtt ttg ctc att  1022
Ile Gly Pro Phe Phe Asp Gly Ser Ile Arg Trp Leu Val Leu Leu Ile
              145                 150                 155 tct atg gct gtc tgc ata att gct atg atc atc ttc tcc agc tgc ttt  1070
Ser Met Ala Val Cys Ile Ile Ala Met Ile Ile Phe Ser Ser Cys Phe
 160                 165                 170 tgt tac aaa cat tat tgc aag agc atc tca agc aga cgt cgt tac aat  1118
Cys Tyr Lys His Tyr Cys Lys Ser Ile Ser Ser Arg Arg Arg Tyr Asn
175                  180                 185                 190 cgt gat ttg gaa cag gat gaa gca ttt att cca gtt gga gaa tca cta  1166
Arg Asp Leu Glu Gln Asp Glu Ala Phe Ile Pro Val Gly Glu Ser Leu
              195                 200                 205 aaa gac ctt att gac cag tca caa agt tct ggt agt ggg tct gga cta  1214
Lys Asp Leu Ile Asp Gln Ser Gln Ser Ser Gly Ser Gly Ser Gly Leu
              210                 215                 220 cct tta ttg gtt cag cga act att gcc aaa cag att cag atg gtc cgg  1262
Pro Leu Leu Val Gln Arg Thr Ile Ala Lys Gln Ile Gln Met Val Arg
              225                 230                 235 caa gtt ggt aaa ggc cga tat gga gaa gta tgg atg ggc aaa tgg cgt  1310
Gln Val Gly Lys Gly Arg Tyr Gly Glu Val Trp Met Gly Lys Trp Arg
              240                 245                 250
```

-continued

| | | |
|---|---|---|
| ggc gaa aaa gtg gcg gtg aaa gta ttc ttt acc act gaa gaa gcc agc<br>Gly Glu Lys Val Ala Val Lys Val Phe Phe Thr Thr Glu Glu Ala Ser<br>255                           260                     265                    270 | 1358 |
| tgg ttt cga gaa aca gaa atc tac caa act gtg cta atg cgc cat gaa<br>Trp Phe Arg Glu Thr Glu Ile Tyr Gln Thr Val Leu Met Arg His Glu<br>                  275                     280                     285 | 1406 |
| aac ata ctt ggt ttc ata gcg gca gac att aaa ggt aca ggt tcc tgg<br>Asn Ile Leu Gly Phe Ile Ala Ala Asp Ile Lys Gly Thr Gly Ser Trp<br>        290                     295                     300 | 1454 |
| act cag ctc tat ttg att act gat tac cat gaa aat gga tct ctc tat<br>Thr Gln Leu Tyr Leu Ile Thr Asp Tyr His Glu Asn Gly Ser Leu Tyr<br>305                           310                     315 | 1502 |
| gac ttc ctg aaa tgt gct aca ctg gac acc aga gcc ctg ctt aaa ttg<br>Asp Phe Leu Lys Cys Ala Thr Leu Asp Thr Arg Ala Leu Leu Lys Leu<br>320                         325                     330 | 1550 |
| gct tat tca gct gcc tgt ggt ctg tgc cac ctg cac aca gaa att tat<br>Ala Tyr Ser Ala Ala Cys Gly Leu Cys His Leu His Thr Glu Ile Tyr<br>335                         340                     345                     350 | 1598 |
| ggc acc caa gga aag ccc gca att gct cat cga gac cta aag agc aaa<br>Gly Thr Gln Gly Lys Pro Ala Ile Ala His Arg Asp Leu Lys Ser Lys<br>                  355                     360                     365 | 1646 |
| aac atc ctc atc aag aaa aat ggg agt tgc tgc att gct gac ctg ggc<br>Asn Ile Leu Ile Lys Lys Asn Gly Ser Cys Cys Ile Ala Asp Leu Gly<br>        370                     375                     380 | 1694 |
| ctt gct gtt aaa ttc aac agt gac aca aat gaa gtt gat gtg ccc ttg<br>Leu Ala Val Lys Phe Asn Ser Asp Thr Asn Glu Val Asp Val Pro Leu<br>385                         390                     395 | 1742 |
| aat acc agg gtg ggc acc aaa cgc tac atg gct ccc gaa gtg ctg gac<br>Asn Thr Arg Val Gly Thr Lys Arg Tyr Met Ala Pro Glu Val Leu Asp<br>400                         405                     410 | 1790 |
| gaa agc ctg aac aaa aac cac ttc cag ccc tac atc atg gct gac atc<br>Glu Ser Leu Asn Lys Asn His Phe Gln Pro Tyr Ile Met Ala Asp Ile<br>415                         420                     425                     430 | 1838 |
| tac agc ttc ggc cta atc att tgg gag atg gct cgt cgt tgt atc aca<br>Tyr Ser Phe Gly Leu Ile Ile Trp Glu Met Ala Arg Arg Cys Ile Thr<br>                  435                     440                     445 | 1886 |
| gga ggg atc gtg gaa gaa tac caa ttg cca tat tac aac atg gta ccg<br>Gly Gly Ile Val Glu Glu Tyr Gln Leu Pro Tyr Tyr Asn Met Val Pro<br>        450                     455                     460 | 1934 |
| agt gat ccg tca tac gaa gat atg cgt gag gtt gtg tgt gtc aaa cgt<br>Ser Asp Pro Ser Tyr Glu Asp Met Arg Glu Val Val Cys Val Lys Arg<br>465                         470                     475 | 1982 |
| ttg cgg cca att gtg tct aat cgg tgg aac agt gat gaa tgt cta cga<br>Leu Arg Pro Ile Val Ser Asn Arg Trp Asn Ser Asp Glu Cys Leu Arg<br>480                         485                     490 | 2030 |
| gca gtt ttg aag cta atg tca gaa tgc tgg gcc cac aat cca gcc tcc<br>Ala Val Leu Lys Leu Met Ser Glu Cys Trp Ala His Asn Pro Ala Ser<br>495                         500                     505                     510 | 2078 |
| aga ctc aca gca ttg aga att aag aag acg ctt gcc aag atg gtt gaa<br>Arg Leu Thr Ala Leu Arg Ile Lys Lys Thr Leu Ala Lys Met Val Glu<br>                  515                     520                     525 | 2126 |
| tcc caa gat gta aaa atc tga tggttaaacc atcggaggag aaactctaga<br>Ser Gln Asp Val Lys Ile<br>                  530 | 2177 |
| ctgcaagaac tgttttttacc catggcatgg gtggaattag agtggaataa ggatgttaac | 2237 |
| ttggttctca gactctttct tcactacgtg ttcacaggct gctaatatta aacctttcag | 2297 |
| tactcttatt aggatacaag ctgggaactt ctaaacactt cattctttat atatggacag | 2357 |
| ctttatttta aatgtggttt ttgatgcctt ttttaagtg ggttttatg aactgcatca | 2417 |

```
agacttcaat cctgattagt gtctccagtc aagctctggg tactgaattg cctgttcata    2477
aaacggtgct ttctgtgaaa gccttaagaa gataaatgag cgcagcagag atggagaaat    2537
agactttgcc ttttacctga gacattcagt tcgtttgtat tctacctttg taaaacagcc    2597
tatagatgat gatgtgtttg ggatactgct tattttatga tagtttgtcc tgtgtcctta    2657
gtgatgtgtg tgtgtctcca tgcacatgca cgccgggatt cctctgctgc catttgaatt    2717
agaagaaaat aatttatatg catgcacagg aagatattgg tggccggtgg ttttgtgctt    2777
taaaaatgca atatctgacc aagattcgcc aatctcatac aagccattta ctttgcaagt    2837
gagatagctt ccccaccagc tttatttttt aacatgaaag ctgatgccaa ggccaaaaga    2897
agtttaaagc atctgtaaat ttggactgtt ttccttcaac caccatttt tttgtggtta     2957 ttatttttgt cacggaaagc atcctctcca aagttggagc ttctattgcc atgaaccatg    3017
cttacaaaga aagcacttct tattgaagtg aattcctgca tttgatagca atgtaagtgc    3077
ctataaccat gttctatatt ctttattctc agtaactttt aaaagggaag ttatttatat    3137
tttgtgtata atgtgcttta tttgcaaatc acccactcct ttacaaccat actttatata    3197
tgtacataca ttcatactgt agaaaccagc tcatgtgtac ctcatatccc atccttaaga    3257
gaagaaatgt tataaagtag aactaaatat aaattttcag aattaatgca ttcaaagtaa    3317
tatatcaaat ccaggacttt gttaacttca ggtaaaaact tcattagggt aatatcatct    3377
caattttttc aaatgaaagg attctctaat tagaaattta tatgtcagag ctgttataaa    3437
tttatcaact gtcaaatatg ttctggacag ctaaatcatt tgagattttt ggttttttga    3497
tttctattcc ctaacttgtg aagacaatga aaaatcaggc agaaatattt agtatctagt    3557
cagtatctgt agctacactg tataactgtt cttcaataaa atggttcata ttttatagaa    3617
aaaaaaaaaa aaaa                                                      3631
```

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agatgctcac tgcgctgga                                                 19

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tccaatgcag gcaatctgtt                                                20

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tggcactggg atgaaatca                                                 19

-continued

```
<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tggttacata aattggtccg a                                              21

<210> SEQ ID NO 25
<211> LENGTH: 465
<212> TYPE: PRT
<213> ORGANISM: Homo sapiens

<400> SEQUENCE: 25
```

Met Asn Val Thr Ser Leu Phe Ser Phe Thr Ser Pro Ala Val Lys Arg
  1               5                  10                  15

Leu Leu Gly Trp Lys Gln Gly Asp Glu Glu Lys Trp Ala Glu Lys
             20                  25                  30

Ala Val Asp Ala Leu Val Lys Lys Leu Lys Lys Lys Gly Ala Met
         35                  40                  45

Glu Glu Leu Glu Lys Ala Leu Ser Cys Pro Gly Gln Pro Ser Asn Cys
 50                  55                  60

Val Thr Ile Pro Arg Ser Leu Asp Gly Arg Leu Gln Val Ser His Arg
 65                  70                  75                  80

Lys Gly Leu Pro His Val Ile Tyr Cys Arg Val Trp Arg Trp Pro Asp
                 85                  90                  95

Leu Gln Ser His His Glu Leu Lys Pro Leu Glu Cys Cys Glu Phe Pro
            100                 105                 110

Phe Gly Ser Lys Gln Lys Glu Val Cys Ile Asn Pro Tyr His Tyr Lys
            115                 120                 125

Arg Val Glu Ser Pro Val Leu Pro Pro Val Leu Val Pro Arg His Ser
        130                 135                 140

Glu Tyr Asn Pro Gln His Ser Leu Leu Ala Gln Phe Arg Asn Leu Gly
145                 150                 155                 160

Gln Asn Glu Pro His Met Pro Leu Asn Ala Thr Phe Pro Asp Ser Phe
                165                 170                 175

Gln Gln Pro Asn Ser His Pro Phe Pro His Ser Pro Asn Ser Ser Tyr
            180                 185                 190

Pro Asn Ser Pro Gly Ser Ser Ser Thr Tyr Pro His Ser Pro Thr
        195                 200                 205

Ser Ser Asp Pro Gly Ser Pro Phe Gln Met Pro Ala Asp Thr Pro Pro
    210                 215                 220

Pro Ala Tyr Leu Pro Pro Glu Asp Pro Met Thr Gln Asp Gly Ser Gln
225                 230                 235                 240

Pro Met Asp Thr Asn Met Met Ala Pro Pro Leu Pro Ser Glu Ile Asn
                245                 250                 255

Arg Gly Asp Val Gln Ala Val Ala Tyr Glu Glu Pro Lys His Trp Cys
            260                 265                 270

Ser Ile Val Tyr Tyr Glu Leu Asn Asn Arg Val Gly Glu Ala Phe His
        275                 280                 285

Ala Ser Ser Thr Ser Val Leu Val Asp Gly Phe Thr Asp Pro Ser Asn
    290                 295                 300

Asn Lys Asn Arg Phe Cys Leu Gly Leu Leu Ser Asn Val Asn Arg Asn

```
                305                 310                 315                 320
Ser Thr Ile Glu Asn Thr Arg Arg His Ile Gly Lys Gly Val His Leu
                325                 330                 335

Tyr Tyr Val Gly Gly Glu Val Tyr Ala Glu Cys Leu Ser Asp Ser Ser
                340                 345                 350

Ile Phe Val Gln Ser Arg Asn Cys Asn Tyr His His Gly Phe His Pro
                355                 360                 365

Thr Thr Val Cys Lys Ile Pro Ser Gly Cys Ser Leu Lys Ile Phe Asn
            370                 375                 380

Asn Gln Glu Phe Ala Gln Leu Leu Ala Gln Ser Val Asn His Gly Phe
385                 390                 395                 400

Glu Thr Val Tyr Glu Leu Thr Lys Met Cys Thr Ile Arg Met Ser Phe
                405                 410                 415

Val Lys Gly Trp Gly Ala Glu Tyr His Arg Gln Asp Val Thr Ser Thr
                420                 425                 430

Pro Cys Trp Ile Glu Ile His Leu His Gly Pro Leu Gln Trp Leu Asp
            435                 440                 445

Lys Val Leu Thr Gln Met Gly Ser Pro His Asn Pro Ile Ser Ser Val
    450                 455                 460

Ser
465

<210> SEQ ID NO 26
<211> LENGTH: 503
<212> TYPE: PRT
<213> ORGANISM: Homo sapiens

<400> SEQUENCE: 26

Met Thr Leu Gly Ser Pro Arg Lys Gly Leu Leu Met Leu Leu Met Ala
1               5                   10                  15

Leu Val Thr Gln Gly Asp Pro Val Lys Pro Ser Arg Gly Pro Leu Val
                20                  25                  30

Thr Cys Thr Cys Glu Ser Pro His Cys Lys Gly Pro Thr Cys Arg Gly
            35                  40                  45

Ala Trp Cys Thr Val Val Leu Val Arg Glu Glu Gly Arg His Pro Gln
    50                  55                  60

Glu His Arg Gly Cys Gly Asn Leu His Arg Glu Leu Cys Arg Gly Arg
65                  70                  75                  80

Pro Thr Glu Phe Val Asn His Tyr Cys Cys Asp Ser His Leu Cys Asn
                85                  90                  95

His Asn Val Ser Leu Val Leu Glu Ala Thr Gln Pro Pro Ser Glu Gln
                100                 105                 110

Pro Gly Thr Asp Gly Gln Leu Ala Leu Ile Leu Gly Pro Val Leu Ala
            115                 120                 125

Leu Leu Ala Leu Val Ala Leu Gly Val Leu Gly Leu Trp His Val Arg
    130                 135                 140

Arg Arg Gln Glu Lys Gln Arg Gly Leu His Ser Glu Leu Gly Glu Ser
145                 150                 155                 160

Ser Leu Ile Leu Lys Ala Ser Glu Gln Gly Asp Thr Met Leu Gly Asp
                165                 170                 175

Leu Leu Asp Ser Asp Cys Thr Thr Gly Ser Gly Ser Gly Leu Pro Phe
                180                 185                 190

Leu Val Gln Arg Thr Val Ala Arg Gln Val Ala Leu Val Glu Cys Val
            195                 200                 205

Gly Lys Gly Arg Tyr Gly Glu Val Trp Arg Gly Leu Trp His Gly Glu
```

```
                210                 215                 220
Ser Val Ala Val Lys Ile Phe Ser Ser Arg Asp Glu Gln Ser Trp Phe
225                 230                 235                 240

Arg Glu Thr Glu Ile Tyr Asn Thr Val Leu Leu Arg His Asp Asn Ile
                245                 250                 255

Leu Gly Phe Ile Ala Ser Asp Met Thr Ser Arg Asn Ser Ser Thr Gln
            260                 265                 270

Leu Trp Leu Ile Thr His Tyr His Glu His Gly Ser Leu Tyr Asp Phe
        275                 280                 285

Leu Gln Arg Gln Thr Leu Glu Pro His Leu Ala Leu Arg Leu Ala Val
    290                 295                 300

Ser Ala Ala Cys Gly Leu Ala His Leu His Val Glu Ile Phe Gly Thr
305                 310                 315                 320

Gln Gly Lys Pro Ala Ile Ala His Arg Asp Phe Lys Ser Arg Asn Val
                325                 330                 335

Leu Val Lys Ser Asn Leu Gln Cys Cys Ile Ala Asp Leu Gly Leu Ala
            340                 345                 350

Val Met His Ser Gln Gly Ser Asp Tyr Leu Asp Ile Gly Asn Asn Pro
        355                 360                 365

Arg Val Gly Thr Lys Arg Tyr Met Ala Pro Glu Val Leu Asp Glu Gln
    370                 375                 380

Ile Arg Thr Asp Cys Phe Glu Ser Tyr Lys Trp Thr Asp Ile Trp Ala
385                 390                 395                 400

Phe Gly Leu Val Leu Trp Glu Ile Ala Arg Arg Thr Ile Val Asn Gly
                405                 410                 415

Ile Val Glu Asp Tyr Arg Pro Pro Phe Tyr Asp Val Val Pro Asn Asp
            420                 425                 430

Pro Ser Phe Glu Asp Met Lys Lys Val Val Cys Val Asp Gln Gln Thr
        435                 440                 445

Pro Thr Ile Pro Asn Arg Leu Ala Ala Asp Pro Val Leu Ser Gly Leu
    450                 455                 460

Ala Gln Met Met Arg Glu Cys Trp Tyr Pro Asn Pro Ser Ala Arg Leu
465                 470                 475                 480

Thr Ala Leu Arg Ile Lys Lys Thr Leu Gln Lys Ile Ser Asn Ser Pro
                485                 490                 495

Glu Lys Pro Lys Val Ile Gln
            500

<210> SEQ ID NO 27
<211> LENGTH: 396
<212> TYPE: PRT
<213> ORGANISM: Homo sapiens

<400> SEQUENCE: 27

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
```

```
                    85                  90                  95
His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
            115                 120                 125

Thr Arg Arg Phe Phe Phe Asn Leu Ser Ser Ile Pro Thr Glu Glu Phe
            130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
            195                 200                 205

Val Thr Pro Ala Val Met Arg Trp Thr Ala Gln Gly His Ala Asn His
210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
            275                 280                 285

Arg Lys Arg Leu Lys Ser Ser Cys Lys Arg His Pro Leu Tyr Val Asp
            290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
            355                 360                 365

Ile Ser Met Leu Tyr Leu Asp Glu Asn Glu Lys Val Val Leu Lys Asn
370                 375                 380

Tyr Gln Asp Met Val Val Glu Gly Cys Gly Cys Arg
385                 390                 395

<210> SEQ ID NO 28
<211> LENGTH: 408
<212> TYPE: PRT
<213> ORGANISM: Homo sapiens

<400> SEQUENCE: 28

Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
```

```
                65                  70                  75                  80
Asp Tyr Met Arg Asp Leu Tyr Arg Leu Gln Ser Gly Glu Glu Glu
                        85                  90                  95

Glu Gln Ile His Ser Thr Gly Leu Glu Tyr Pro Glu Arg Pro Ala Ser
                100                 105                 110

Arg Ala Asn Thr Val Arg Ser Phe His His Glu Glu His Leu Glu Asn
            115                 120                 125

Ile Pro Gly Thr Ser Glu Asn Ser Ala Phe Arg Phe Leu Phe Asn Leu
        130                 135                 140

Ser Ser Ile Pro Glu Asn Glu Ala Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn
        195                 200                 205

Val Thr Arg Trp Glu Thr Phe Asp Val Ser Pro Ala Val Leu Arg Trp
210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
        275                 280                 285

Arg Ala Lys Arg Ser Pro Lys His His Ser Gln Arg Ala Arg Lys Lys
    290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
        355                 360                 365

Pro Lys Ala Cys Cys Val Pro Thr Glu Leu Ser Ala Ile Ser Met Leu
    370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405

<210> SEQ ID NO 29
<211> LENGTH: 770
<212> TYPE: PRT
<213> ORGANISM: Homo sapiens

<400> SEQUENCE: 29

Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
                20                  25                  30

Phe Leu Ala Pro Trp Ile Glu Ser Gln Asp Trp Ala Tyr Ala Ala Ser
```

```
                    35                  40                  45
Lys Glu Ser His Ala Thr Leu Val Phe His Asn Leu Gly Glu Ile
            50                  55                  60
Asp Gln Gln Tyr Ser Arg Phe Leu Gln Glu Ser Asn Val Leu Tyr Gln
 65                  70                  75                  80
His Asn Leu Arg Arg Ile Lys Gln Phe Leu Gln Ser Arg Tyr Leu Glu
                85                  90                  95
Lys Pro Met Glu Ile Ala Arg Ile Val Ala Arg Cys Leu Trp Glu Glu
            100                 105                 110
Ser Arg Leu Leu Gln Thr Ala Ala Thr Ala Ala Gln Gln Gly Gly Gln
            115                 120                 125
Ala Asn His Pro Thr Ala Ala Val Val Thr Glu Lys Gln Gln Met Leu
            130                 135                 140
Glu Gln His Leu Gln Asp Val Arg Lys Arg Val Gln Asp Leu Glu Gln
145                 150                 155                 160
Lys Met Lys Val Val Glu Asn Leu Gln Asp Asp Phe Asp Phe Asn Tyr
                165                 170                 175
Lys Thr Leu Lys Ser Gln Gly Asp Met Gln Asp Leu Asn Gly Asn Asn
            180                 185                 190
Gln Ser Val Thr Arg Gln Lys Met Gln Gln Leu Glu Gln Met Leu Thr
            195                 200                 205
Ala Leu Asp Gln Met Arg Arg Ser Ile Val Ser Glu Leu Ala Gly Leu
            210                 215                 220
Leu Ser Ala Met Glu Tyr Val Gln Lys Thr Leu Thr Asp Glu Glu Leu
225                 230                 235                 240
Ala Asp Trp Lys Arg Arg Gln Gln Ile Ala Cys Ile Gly Gly Pro Pro
                245                 250                 255
Asn Ile Cys Leu Asp Arg Leu Glu Asn Trp Ile Thr Ser Leu Ala Glu
            260                 265                 270
Ser Gln Leu Gln Thr Arg Gln Gln Ile Lys Lys Leu Glu Glu Leu Gln
            275                 280                 285
Gln Lys Val Ser Tyr Lys Gly Asp Pro Ile Val Gln His Arg Pro Met
290                 295                 300
Leu Glu Glu Arg Ile Val Glu Leu Phe Arg Asn Leu Met Lys Ser Ala
305                 310                 315                 320
Phe Val Val Glu Arg Gln Pro Cys Met Pro Met His Pro Asp Arg Pro
                325                 330                 335
Leu Val Ile Lys Thr Gly Val Gln Phe Thr Thr Lys Val Arg Leu Leu
            340                 345                 350
Val Lys Phe Pro Glu Leu Asn Tyr Gln Leu Lys Ile Lys Val Cys Ile
            355                 360                 365
Asp Lys Asp Ser Gly Asp Val Ala Ala Leu Arg Gly Ser Arg Lys Phe
            370                 375                 380
Asn Ile Leu Gly Thr Asn Thr Lys Val Met Asn Met Glu Glu Ser Asn
385                 390                 395                 400
Asn Gly Ser Leu Ser Ala Glu Phe Lys His Leu Thr Leu Arg Glu Gln
                405                 410                 415
Arg Cys Gly Asn Gly Gly Arg Ala Asn Cys Asp Ala Ser Leu Ile Val
            420                 425                 430
Thr Glu Glu Leu His Leu Ile Thr Phe Glu Thr Glu Val Tyr His Gln
            435                 440                 445
Gly Leu Lys Ile Asp Leu Glu Thr His Ser Leu Pro Val Val Val Ile
            450                 455                 460
```

```
Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
            515                 520                 525

Ala Glu Lys Leu Leu Gly Pro Gly Val Asn Tyr Ser Gly Cys Gln Ile
530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
            580                 585                 590

Arg Glu Arg Ala Ile Leu Ser Thr Lys Pro Pro Gly Thr Phe Leu Leu
            595                 600                 605

Arg Phe Ser Glu Ser Ser Lys Glu Gly Gly Val Thr Phe Thr Trp Val
610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
            660                 665                 670

Leu Tyr Pro Asp Ile Pro Lys Glu Glu Ala Phe Gly Lys Tyr Cys Arg
            675                 680                 685

Pro Glu Ser Gln Glu His Pro Glu Ala Asp Pro Gly Ser Ala Ala Pro
690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Glu Leu Thr Ser Glu Cys Ala Thr Ser
            755                 760                 765

Pro Met
    770

<210> SEQ ID NO 30
<211> LENGTH: 532
<212> TYPE: PRT
<213> ORGANISM: Homo sapiens

<400> SEQUENCE: 30

Met Pro Gln Leu Tyr Ile Tyr Ile Arg Leu Leu Gly Ala Tyr Leu Phe
1               5                   10                  15

Ile Ile Ser Arg Val Gln Gly Gln Asn Leu Asp Ser Met Leu His Gly
                20                  25                  30

Thr Gly Met Lys Ser Asp Ser Asp Gln Lys Lys Ser Glu Asn Gly Val
            35                  40                  45

Thr Leu Ala Pro Glu Asp Thr Leu Pro Phe Leu Lys Cys Tyr Cys Ser
50                  55                  60
```

```
Gly His Cys Pro Asp Asp Ala Ile Asn Asn Thr Cys Ile Thr Asn Gly
 65                  70                  75                  80

His Cys Phe Ala Ile Ile Glu Glu Asp Asp Gln Gly Glu Thr Thr Leu
                     85                  90                  95

Ala Ser Gly Cys Met Lys Tyr Glu Gly Ser Asp Phe Gln Cys Lys Asp
                100                 105                 110

Ser Pro Lys Ala Gln Leu Arg Arg Thr Ile Glu Cys Arg Thr Asn
                115                 120                 125

Leu Cys Asn Gln Tyr Leu Gln Pro Thr Leu Pro Val Val Ile Gly
            130                 135                 140

Pro Phe Phe Asp Gly Ser Ile Arg Trp Leu Val Leu Leu Ile Ser Met
145                 150                 155                 160

Ala Val Cys Ile Ile Ala Met Ile Ile Phe Ser Ser Cys Phe Cys Tyr
                    165                 170                 175

Lys His Tyr Cys Lys Ser Ile Ser Ser Arg Arg Tyr Asn Arg Asp
                180                 185                 190

Leu Glu Gln Asp Glu Ala Phe Ile Pro Val Gly Glu Ser Leu Lys Asp
            195                 200                 205

Leu Ile Asp Gln Ser Gln Ser Ser Gly Ser Gly Ser Gly Leu Pro Leu
            210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
                245                 250                 255

Lys Val Ala Val Lys Val Phe Phe Thr Thr Glu Glu Ala Ser Trp Phe
                260                 265                 270

Arg Glu Thr Glu Ile Tyr Gln Thr Val Leu Met Arg His Glu Asn Ile
                275                 280                 285

Leu Gly Phe Ile Ala Ala Asp Ile Lys Gly Thr Gly Ser Trp Thr Gln
            290                 295                 300

Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
                325                 330                 335

Ser Ala Ala Cys Gly Leu Cys His Leu His Thr Glu Ile Tyr Gly Thr
                340                 345                 350

Gln Gly Lys Pro Ala Ile Ala His Arg Asp Leu Lys Ser Lys Asn Ile
                355                 360                 365

Leu Ile Lys Lys Asn Gly Ser Cys Cys Ile Ala Asp Leu Gly Leu Ala
            370                 375                 380

Val Lys Phe Asn Ser Asp Thr Asn Glu Val Asp Val Pro Leu Asn Thr
385                 390                 395                 400

Arg Val Gly Thr Lys Arg Tyr Met Ala Pro Glu Val Leu Asp Glu Ser
                405                 410                 415

Leu Asn Lys Asn His Phe Gln Pro Tyr Ile Met Ala Asp Ile Tyr Ser
                420                 425                 430

Phe Gly Leu Ile Ile Trp Glu Met Ala Arg Arg Cys Ile Thr Gly Gly
            435                 440                 445

Ile Val Glu Glu Tyr Gln Leu Pro Tyr Tyr Asn Met Val Pro Ser Asp
450                 455                 460

Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Cys Leu Arg Ala Val
                485                 490                 495
```

```
Leu Lys Leu Met Ser Glu Cys Trp Ala His Asn Pro Ala Ser Arg Leu
            500                 505                 510

Thr Ala Leu Arg Ile Lys Lys Thr Leu Ala Lys Met Val Glu Ser Gln
            515                 520                 525

Asp Val Lys Ile
        530
```

METHODS FOR IDENTIFYING AGENTS FOR PREVENTING OR TREATING PROLIFERATIVE DISEASES, AND FOR INHIBITING EXTRACELLULAR MATRIX OR α1 TYPE IV COLLAGEN

TECHNICAL FIELD

The present invention relates to a method of detecting proliferative diseases causing sclerosis and a kit therefor; a prophylactic and/or therapeutic agent for proliferative diseases causing sclerosis, as well as a method of identifying substances effective in preventing and/or treating proliferative diseases causing sclerosis and a kit therefor.

BACKGROUND ART

α1 type IV collagen (Col4) is a major component of the vascular basement membrane that lies beneath the endothelium and surrounds medial smooth muscle cells, and the overproduction of Col4 plays a crucial role in the process of diabetic angiopathy, arteriosclerosis and aging-related diseases. Prolonged exposure to hyperglycemia is now recognized as a significant causal factor of diabetic complications (non-patent documents 1 and 2). Excessive advanced glycation end-products (AGEs) produced as a result of hyperglycemia are known to induce a variety of cellular events in vascular cells and other cells, possibly through several functional AGEs receptors, thereby modulating the disease processes (non-patent documents 3, 4 and 5). AGEs have been recently accepted as playing an important role, not only in diabetic complications, but also in arteriosclerosis caused by aging (non-patent documents 6 and 7). Moreover, a truncated, soluble form of the receptor for AGEs was reported to inhibit the progress of accelerated diabetic atherosclerosis (non-patent document 8).

Morphologically, the progress of diabetic nephropathy is characterized by progressive thickening of the glomerular basement membrane (GBM) and by expansion of the mesangial extracellular matrix (ECM). Since Col4 is a major component of the thickened GBM and expanded ECM, it is important to clarify how Col4 is regulated at the transcriptional level in the diabetic state. The 130-bp bidirectional promoter of Col4 contains a large stem-loop structure (CIV) which has been shown to interact with several DNA binding proteins (non-patent documents 9). Using a gel mobility shift assay, the present inventors previously reported that an unknown protein binds to the CIV site only when Col4 is induced by the exposure to AGEs (non-patent document 10).

Both mesangial cell proliferation and glomerulosclerosis are major pathological features in progressive glomerular disorders. The fact that mesangial cell proliferation is observed in many glomerular sclerosing diseases suggests that this process is important in progressive glomerular disorders (non-patent document 11 (A1), non-patent document 12 (A2)). Both events are concomitantly observed in most of glomerular diseases, but it is not clear how cell proliferation is involved in the progress of glomerulosclerosis.

Platelet derived growth factor (PDGF) was shown as a critical mitogen for mesangial cells in vitro and in vivo (non-patent document 13 (3A), non-patent document 14 (4A)). Not only in experimental models but also in human glomerular diseases, it has been proved that PDGF plays a key role in the progress of glomerulosclerosis (non-patent document 13 (A3)). PDGF-BB was also reported to be essential for mesangial cell proliferation (non-patent document 15 (A5)), which is followed by development of glomerulosclerosis in a remnant kidney model (non-patent document 16 (A6)). Introduction of neutralizing anti-PDGF antibody markedly ameliorated both mesangial proliferation and glomerulosclerosis in a rat glomerulonephritis model (non-patent document 17 (A7)), but little was known about the mechanism how inhibition of cell proliferation reduces glomerular sclerotic lesions.

Non-patent document 1:
The Diabetes Control and Complications Trial Research Group. N. Engl. J. Med. 329, 977-986 (1993).

Non-patent document 2:
UK Prospective Diabetes Study (UKPDS) Group. Lancet 352, 837-853 (1998)

Non-patent document 3:
H. Vlassara, et al., Proc. Natl. Acad. Sci. USA 91, 11704-11708 (1994).

Non-patent document 4: M. Brownlee, A. Cerami, H. Vlassara, N. Engl. J. Med. 318, 1315-1321 (1988).

Non-patent document 5:
T. Doi, et al., Proc. Natl. Acad. Sci. USA 89, 2873-2877 (1992).

Non-patent document 6:
H. Vlassara, et al., Proc. Natl. Acad. Sci. USA 89, 12043-12047 (1992).

Non-patent document 7:
M. S. Huijberts, et al., J. Clin. Invest. 92, 1407-1411 (1993).

Non-patent document 8:
S. L. Park, et al., Nature Med. 9, 1025-1031 (1998)

Non-patent document 9:
L. A. Bruggeman, P. D. Burbelo, Y Yamada, P. E. Klotman, Oncogene 7, 1497-1502 (1992).

Non-patent document 10:
N. Iehara, H. Takeoka, Y. Yamada, T. Kita, T. Doi, Kidney Int. 50, 1166-1172 (1996).

Non-patent document 11:
Fogo A, Ichikawa I. Evidence for the central role of glomerular growth promoters in the development of sclerosis. Semin Nephrol. 1989 December; 9(4):329-42.

Non-patent document 12:
Striker L J, Doi T, Elliot S, Striker G E. The contribution of glomerular mesangial cells to progressive glomerulosclerosis. Semin Nephrol. 1989 December; 9(4):318-28. Review.

Non-patent document 13:
Floege J, Johnson R J: Multiple roles for platelet-derived growth factor in renal disease. Miner Electrolyte Metab 21: 271-282, 1995

Non-patent document 14:
Doi T, Vlassara H, Kirstein M, Yamada Y. Striker G E, Striker L J: Receptor-specific increase in extracellular matrix production by mesangial cells by advanced glycosylation end products is mediated via platelet-derived growth factor. Proc Natl Acad Sci USA 89: 2873-2877, 1992

Non-patent document 15:
Barnes J L, Hevey K A. Glomerular mesangial cell migration in response to platelet-derived growth factor. Lab Invest. 1990 Mar; 62(3):379-82.

Non-patent document 16:
Floege, J., Burns, M. W., Alpers, C. E., Yoshimura, A., Pritzl, P., Gordon, K., Seifert, R. A., Bowen-Pope, D. F., Couser, W. G., and Johnson, R. J.: Glomerular cell proliferation and PDGF expression precede glomerulosclerosis in the remnant kidney model. Kidney Int. 41: 297-309, 1992

Non-patent document 17:
Johnson, R. J., Raines, E. W., Floege, J, et al: Inhibition of mesangial cell proliferation and matrix expansion in glomerulonephritis in the rat by antibody to platelet-derived growth factor. J Exp Med 175: 1413-1416, 1992

DISCLOSURE OF THE INVENTION

Problem For Solution by the Invention

Diabetic nephropathy is the leading cause of end-stage renal failure. Type IV collagen is a principal component of the vascular basement membrane and the mesangial matrix of renal glomeruli, and plays a crucial role in the process of diabetic anigiopathy. However, what is directly involved in the overproduction of type IV collagen in diabetic state is unknown. It is an object of the present invention to identify the substance that is directly involved in the overproduction of type IV collagen and to demonstrate that the substance plays a critical role as a causative of diabetic nephropathy. It is another object of the present invention to provide a method and a kit for detecting diabetic nephropathy using the substance that is directly involved in the overproduction of type IV collagen. It is still another object of the invention to provide uses of those substances having an inhibitory effect on the expression of the substance that is directly involved in the overproduction of type IV collagen. It is still another object of the invention to provide a method and a kit for identifying substances effective in preventing and/or treating diabetic nephropathy; a method and a kit for identifying substances effective in inhibiting the increase of extracellular matrix; and a method and a kit for identifying substances effective in inhibiting the expression of $\alpha 1$ type IV collagen.

Further, the present invention aims at demonstrating the effect of administration of anti-PDGF β receptor antibody (APB5) (which inhibits activation by PDGF-B chain) on rat glomerulonephritis to thereby demonstrate in vivo and in vitro that the PDGF signal transduction pathway is regulating both glomerular cell proliferation and glomerulosclerosis. The present invention also aims at providing a method and a kit for detecting proliferative diseases causing sclerosis, using those substances involved in glomerular cell proliferation and glomerulosclerosis. Further, the present invention aims at providing uses of substances which have an inhibitory effect on the expression of those substances involved in glomerular cell proliferation and glomerulosclerosis. Still further, the present invention aims at providing a method and a kit for identifying substances effective in preventing and/or treating proliferative diseases causing sclerosis; a method and a kit for identifying substances effective in inhibiting the increase of extracellular matrix; and a method and a kit for identifying substances effective in inhibiting the expression of $\alpha 1$ type IV collagen.

Means to Solve the Problem

The present inventors have identified Smad1 as a substance that is directly involved in the overproduction of type IV collagen and demonstrated that Smad1 plays a critical role as a causative of diabetic nephropathy. The present inventors have also examined the expression of Smad1 and activin receptor-like kinase 1 (ALK1) in renal glomeruli of healthy persons and diabetic nephropathy patients, and found that while the expression of Smad1 and ALK1 in diabetic nephropathy patients is proportional to the severity of sclerosis lesions, the expression of Smad1 and ALK1 is hardly observed in healthy persons. Further, the present inventors have also found that the expression of BMP2 and BMP4 (which regulate the expression of Smad1) increases in the presence of AGEs stimulation.

On the other hand, the fact that mesangial cell proliferation is observed in many glomerul sclerosing diseases suggests that this process is important in progressive glomerular disorders. However, relations between the cell proliferation and glomerulosclerosis are not clear. Recently, the present inventors showed that the overexpression of type TV collagen (Col4), one of major components of glomerulosclerosis, is transcriptionally regulated by Smad1 in diabetic glomerulosclerosis. In this study, the present inventors have demonstrated the effect of administration of anti-PDGF β-receptor antibody (APB5) (which inhibits activation by PDGF-B chain) on rat glomerulonephritis and thereby demonstrated in vivo and in vitro that the PDGF signal transduction pathway is regulating both glomerular cell proliferation and glomerulosclerosis.

An experimental model of mesangial proliferative glomerulonephritis (Thy1 GN) was induced by a single intravenous injection of anti-rat Thy-1.1 monoclonal antibody. In Thy1 GN, mesangial cell proliferation and expression of Col4 peaked at day 6. Immunohistochemical staining was performed to examine the expression of Smad1, phosphorylated Smad1 (pSmad1) and phosphorylated STAT3 (pSTAT3). The peak of glomerular Smad1 expression occurred at day 6, which was consistent with the peak of mesangial proliferation. Glomerular pSmad1 expression was upregulated from day 1 of Thy1 GN, and the peak of glomerular pSmad1 expression occurred at day 4 of the disease. In APB5-treated groups, both mesangial proliferation and glomerulosclerosis were reduced significantly. Smad1, pSmad1 and pSTAT3 expressions were also significantly reduced by administration of APB5 at every point examined. APB5 treatment reduced mesangial cell proliferation in association with reduction in pSmad1, pSTAT3 and Col IV protein expressions in vitro. Introduction of dominant negative STAT3 decreased the expression of Col4 significantly in cultured mesangial cells. These data suggest that activation of STAT3 and Smad1 is involved in the progress from mesangial cell proliferation to glomerulosclerosis.

The present invention has been achieved based on these findings.

The subject matters of the present invention are as described below.

(1) A method of detecting proliferative diseases causing sclerosis, comprising measuring the expression of at least one substance selected from the group consisting of STAT3, phosphorylated STAT3, Smad1, phosphorylated Smad1, activin receptor-like kinase 1, activin receptor-like kinase 3 and bone morphogenetic proteins in a biological sample.

(2) A method of evaluating the degree of progress and/or the efficacy of treatment of proliferative diseases causing sclerosis, comprising measuring the expression of at least one substance selected from the group consisting of STAT3, phosphorylated STAT3, Smad1, phosphorylated Smad1, activin receptor-like kinase 1, activin receptor-like kinase 3 and bone morphogenetic proteins in a biological sample.

(3) A kit for detecting proliferative diseases causing sclerosis, comprising a reagent(s) for measuring the expression of at least one substance selected from the group consisting of STAT3, phosphorylated STAT3, Smad1, phosphorylated Smad1, activin receptor-like kinase 1, activin receptor-like kinase 3 and bone morphogenetic proteins in a biological sample.

(4) A kit for evaluating the degree of progress and/or the efficacy of treatment of proliferative diseases causing sclerosis, comprising a reagent(s) for measuring the expression of at least one substance selected from the group consisting of STAT3, phosphorylated STAT3, Smad1, phosphorylated Smad1, activin receptor-like kinase 1, activin receptor-like kinase 3 and bone morphogenetic proteins in a biological sample.

(5) A method of detecting diabetic nephropathy, comprising measuring the expression of Smad1 and/or a substance having Smad1-activating effect in a biological sample.

(6) A method of evaluating the degree of progress and/or the efficacy of treatment of diabetic nephropathy, comprising measuring the expression of Smad1 and/or a substance having Smad1-activating effect in a biological sample.

(7) A kit for detecting diabetic nephropathy, comprising a reagent(s) for measuring the expression of Smad1 and/or a substance having Smad1-activating effect.

(8) A kit for evaluating the degree of progress and/or the efficacy of treatment of diabetic nephropathy, comprising a reagent(s) for measuring the expression of Smad1 and/or a substance having Smad1-activating effect.

(9) A prophylactic and/or therapeutic agent for proliferative diseases causing sclerosis, comprising as an active ingredient a substance having an inhibitory effect on the expression of at least one substance selected from the group consisting of STAT3, phosphorylated STAT3, Smad1 and phosphorylated Smad1.

(10) A drug inhibiting the increase of extracellular matrix, comprising as an active ingredient a substance having an inhibitory effect on the expression of at least one substance selected from the group consisting of STAT3, phosphorylated STAT3, Smad1 and phosphorylated Smad1.

(11) A drug inhibiting the expression of α1 type IV collagen, comprising as an active ingredient a substance having an inhibitory effect on the expression of at least one substance selected from the group consisting of STAT3, phosphorylated STAT3, Smad1 and phosphorylated Smad1.

(12) A method of identifying substances effective in preventing and/or treating proliferative diseases causing sclerosis, comprising judging whether or not a test substance inhibits the expression of at least one substance selected from the group consisting of STAT3, phosphorylated STAT3, Smad1 and phosphorylated Smad1.

(13) A method of identifying substances effective in inhibiting the increase of extracellular matrix, comprising judging whether or not a test substance inhibits the expression of at least one substance selected from the group consisting of STAT3, phosphorylated STAT3, Smad1 and phosphorylated Smad1.

(14) A method of identifying substances effective in inhibiting the expression of α1 type IV collagen, comprising judging whether or not a test substance inhibits the expression of at least one substance selected from the group consisting of STAT3, phosphorylated STAT3, Smad1 and phosphorylated Smad1.

(15) A kit for identifying substances effective in preventing and/or treating proliferative diseases causing sclerosis, comprising a reagent(s) for measuring the expression of at least one substance selected from the group consisting of STAT3, phosphorylated STAT3, Smad1 and phosphorylated Smad1.

(16) A kit for identifying substances effective in inhibiting the increase of extracellular matrix, comprising a reagent(s) for measuring the expression of at least one substance selected from the group consisting of STAT3, phosphorylated STAT3, Smad1 and phosphorylated Smad1.

(17) A kit for identifying substances effective in inhibiting the expression of α1 type IV collagen, comprising a reagent(s) for measuring the expression of at least one substance selected from the group consisting of STAT3, phosphorylated STAT3, Smad1 and phosphorylated Smad1.

EFFECT OF THE INVENTION

According to the present invention, Smad1 was identified as a substance directly involved in the overproduction of type IV collagen, and it was demonstrated that Smad1 has a critical role as a causative of diabetic nephropathy. With these findings, it has become possible to detect diabetic nephropathy; besides, a prophylactic and/or therapeutic for diabetic nephropathy, a drug inhibiting the increase of extracellular matrix, and a drug inhibiting the expression of α1 type IV collagen have been provided. Further, according to the present invention, there have been provided a method and a kit for identifying substances effective in preventing and/or treating diabetic nephropathy; a method and a kit for identifying substances effective in inhibiting the increase of extracellular matrix; and a method and a kit for identifying substances effective in inhibiting the expression of α1 type IV collagen.

Further, according to the present invention, it has been demonstrated that the activation of STAT3 and Smad1 is in a key pathway regulating the interaction between cell proliferation and glomerulosclerosis which are the two phenomena observed in progressive glomerular disorders. With this finding, it has become possible to detect proliferative diseases causing sclerosis; besides, a prophylactic and/or therapeutic for proliferative diseases causing sclerosis, a drug inhibiting the increase of extracellular matrix, and a drug inhibiting the expression of α1 type IV collagen have been provided. Further, according to the present invention, there have been provided a method and a kit for identifying substances effective in preventing and/or treating proliferative diseases causing sclerosis; a method and a kit for identifying substances effective in inhibiting the increase of extracellular matrix; and a method and a kit for identifying substances effective in inhibiting the expression of α1 type IV collagen.

The present specification encompasses the contents described in the specification and/or the drawings of Japanese Patent Application No. 2003-319538 based on which the present patent application claims priority.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5 shows the results of comparison between mRNA expression levels in mesangial cells cultured in the presence of AGEs and corresponding mRNA expression levels in mesangial cells cultured in the presence of BSA.

BEST MODE FOR CARRYING OUT THE INVENTION

1. Method and Kit for Detecting Diabetic Nephropathy

The present invention provides a method of detecting diabetic nephropathy, comprising measuring the expression of Smad1 and/or a substance having Smad1-activating effect in a biological sample.

The biological sample may be any biological sample as long as Smad1 and/or a substance having Smad1-activating effect is detectable therein. Specific examples of the biological sample which may be used in the invention include renal tissue sections, blood, sera and urine.

Figure 8:
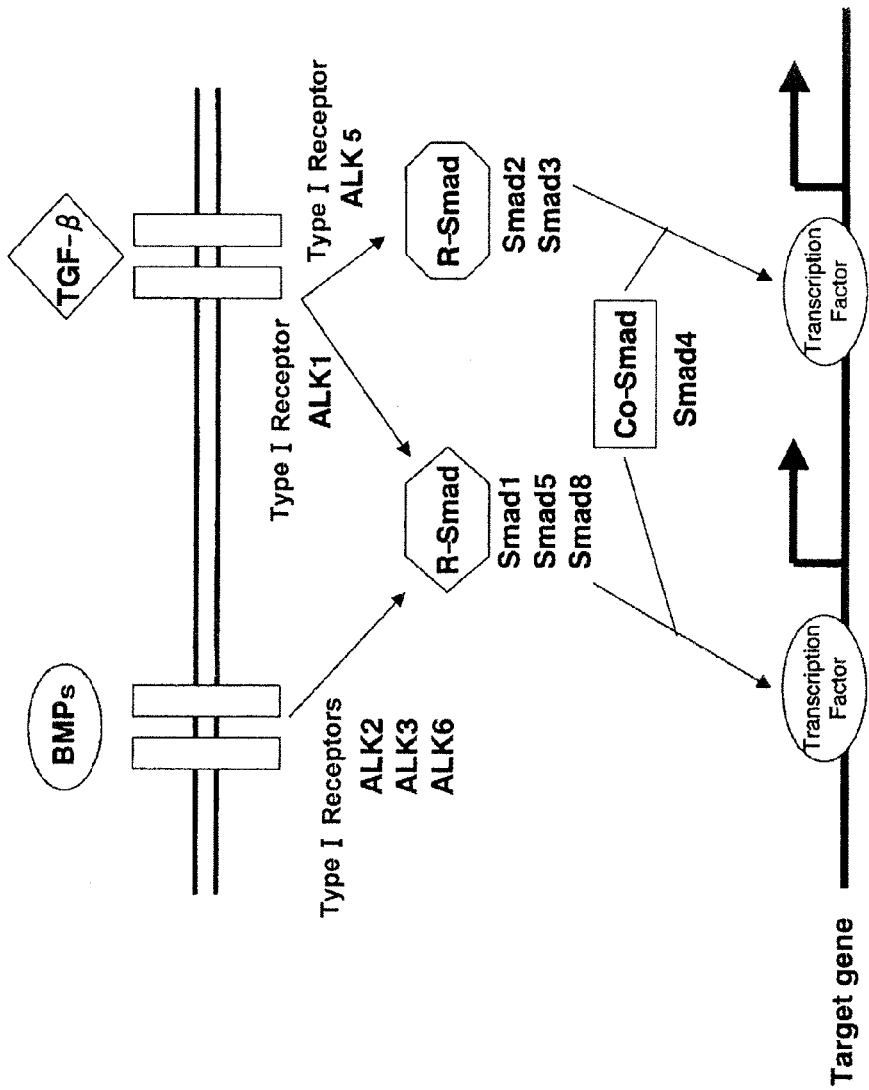
FIG. 8 is a schematic drawing of the signal transduction pathway based on the results of Example 1.

Nine Smad proteins (Smad1 to Smad9) have been identified in mammals, and Smad1 is known as a member of the bone morphogenetic protein (BMP) signal transduction pathway. BMPs regulate the transcription of target genes through activin receptor kinase 2, 3 and 6 (AKL2, ALK3 and ALK6) (Zwijsen A. et al., FEBS Letters 546, 2003, 133-139). In addition to Smad1, Smad5 and Smad8 are also involved in the BMP signaling specifically. Further, Smad2 and Smad3 are said to be involved in the TGF-β/activin signaling specifically. On the other hand, it has been elucidated that Smad1 transduces TGF-β signals through activin receptor-like kinase 1 (ALK1) to thereby regulate the transcription of target genes in endothelial cells and hematopoietic cells (Goumans M J. et al., EMBO J., 2002, Apr 2, 21(7), 1743-53). This means that two major signal transduction pathways (BMP pathway and TGF-β pathway) exist in which transcription of target genes is regulated by activation of Smad1 (FIG. 8). However, sufficient examination has not been made yet as to a pathway of which combination is the most important.

The "substance having Smad1-activating effect" may be any substance as long as it is capable activating Smad1. For example, substances such as activin receptor-like kinase 1 (ALK1) and activin receptor-like kinase 3 (ALK3) which activate Smad1 directly may be given. Alternatively, substances such as bone morphogenetic proteins (BMPs) which activate Smad1 indirectly through activation of activin receptor kinases (ALKs) may be given.

It is clear from the study of the present inventors (Example 2) that PDGF also activates Smad1 though directly or indirectly is not known.

The expression "activates Smad1" means to phosphorylate serine residues of Smad1 and/or to translocate Smad1 into the nucleus.

Activin receptor-like kinase 1 (ALK1) is one of the type I receptors which bind to TGF-β family proteins and is known to activate Smad1 (Chen YG, et al., Smad1 recognition and activation by the ALK1 group of transforming growth factor-β family receptors J. Biol. Chem. Vol. 274, No. 6, 3672-3677, 1999). ALK1 is expressed highly in the placenta, lung and vascular endothelial cells in human, and mutations of ALK1 result in human hereditary hemorrhagic telangiectasia (HHT) type II, also known as Osler-Rendu-Weber syndrome (non-patent document 17).

Activin receptor-like kinase 3 (ALK3), also known as BMPR-IA, is one of the type I receptors which bind to BMP family proteins, and is a serine-threonine receptor. ALK3 bound to BMPs activates Smad1, Smad5 and Smad8 and carries out the transduction of signals into the nucleus.

Bone morphogenetic proteins (BMPs) are a member of TGF-β superfamily and involved in bone morphogenesis as well as development of four limbs and differentiation of the nerve system in the developmental stage. However, several reports that BMPs are involved in the regulation of development of the metanephros have been made recently and attracted attention. The kidney develops from the intermediate mesoderm and is formed through the three stages of pronephros, mesonephros and metanephros. Most of the pronephros and mesonephros undergo retroplasia eventually; the kidney which functions in mammalian adults is the metanephros. Transcripts for BMPs and their receptors have been localized in the developing metanephros. BMP2, BMP4 and BMP7 have direct or indirect roles in regulation of ureteric branching morphogenesis and branch formation in vitro. In vivo, it is reported that renal phenotypes vary between BMP7 null mutation-homozygous mutant mice and BMP4 null mutation-heterozygous mutant mice (Martinez G. et al, Int J Dev Biol. 2002; 46(4):525-33).

TGF-β has diversified effects and plays important roles in proliferation/differentiation of various cells, production of extracellular matrix, apoptosis, immune system, and so forth. TGF-β binds to receptors on cell surfaces to thereby transduce its signals into cells. A series of Smad protein molecules play important roles in the intracellular signal transduction.

To date, a pathway in which TGF-β activates Smad2 and Smad3 through ALK5 under hyperglycemic conditions to thereby bring about the overproduction of extracellular matrix such as α1 type IV collagen has been considered to be involved in the development and progress of diabetic nephropathy (Jin H. et al., Kidney International, 63, 2003, 2010-2019). However, the present study shows for the first time that there exists a pathway which brings about overproduction of extracellular matrix through Smad1 under hyperglycemic conditions.

The expression of Smad1 and/or a substance having Smad1-activating effect may be measured at the nucleic acid level (i.e. mRNA expression) and/or the protein level.

With respect to the measurement at the nucleic acid level, total RNA may be extracted from a biological sample, and then the mRNA of Smad1 and/or a substance having Smad1-activating effect may be measured by RT-PCR using a pair of appropriate primers. These primers may be designed so that a specific region in sequences such as the nucleotide sequence for human-derived Smad1 mRNA available as NM_005900 in NCBI Refseq database (SEQ ID NO: 1); the nucleotide sequence for human-derived activin receptor-like kinase 1 mRNA available as NM_000020 in NCBI Refseq database (SEQ ID NO: 2); the nucleotide sequence for BMP2 mRNA available as ACCESSION NM_001200 VERSION NM_001200.1 in GenBank database (SEQ ID NO: 3); and the nucleotide sequence for. BMP4 mRNA available as ACCESSION NM_001202 VERSION NM_001202.2 in GenBank database (SEQ ID NO: 4) is amplified specifically. Examples of nucleotide sequences for appropriate primer pairs are as described below.

RT-PCR to amplify Smad1 mRNA specifically:

```
Forward primer:
5'-ACTACCACCACGGCTTTCAC-3'       (SEQ ID NO: 5)

Reverse primer:
5'-AATAGGATTGTGGGGTGAGC-3'       (SEQ ID NO: 6)
```

RT-PCR to amplify ALK1 mRNA specifically:

```
Forward primer:
5'-ccgtcaagatcttctcctcg-3'       (SEQ ID NO: 7)

Reveres primer:
5'-tcatgtctgaggcgatgaag-3'       (SEQ ID NO: 8)
```

RT-PCR to amplify BMP2 mRNA specifically:

```
Forward primer:
5'-cccagcgtgaaaagagagac-3'        (SEQ ID NO: 9)

Reverse primer:
5'-gagaccgcagtccgtctaag-3'        (SEQ ID NO: 10)
```

RT-PCR to amplify BMP4 mRNA specifically:

```
Forward primer:
5'-tgagcctttccagcaagttt-3'        (SEQ ID NO: 11)

Reverse primer:
5'-cttccccgtctcaggtatca-3'        (SEQ ID NO: 12)
```

Alternatively, total RNA may be extracted from a biological sample, and then the mRNA of Smad1 and/or a substance having Smad1-activating effect may be measured by Northern hybridization using an appropriate probe. The appropriate probe may be designed based on sequences such as the nucleotide sequence for human-derived Smad1 MRNA available as NM_005900 in NCBI Refseq database (SEQ ID NO: 1); the nucleotide sequence for human-derived activin receptor-like kinase 1 mRNA available as NM_000020 in NCBI Refseq database (SEQ ID NO: 2); the nucleotide sequence for BMP2 MRNA available as ACCESSION NM_001200 VERSION NM_001200.1 in GenBank database (SEQ ID NO: 3); and the nucleotide sequence for BMP4 mRNA available as ACCESSION NM_001202 VERSION NM_001202.2 in GenBank database (SEQ ID NO: 4) so that it specifically hybridizes to a part or the entire region of such sequences. The probe may be labeled with a substance such as $^{32}P$.

With respect to the measurement at the protein level, Smad1 and/or a substance having Smad1-activating effect may be measured by a method such as Western blotting, ELISA or immunohistochemical analysis using, for example, anti-Smad1 antibody and/or antibody to the substance having Smad1-activating effect. The anti-Smad1 antibody and/or antibody to the substance having Smad1-activating effect may be labeled with a fluorescent dye, enzyme, heavy metal, or the like (direct method). Alternatively, instead of labeling these antibodies, antibodies (secondary antibodies) specific to these antibodies (primary antibodies) may be labeled with a fluorescent dye, enzyme, heavy metal, or the like (indirect method). Preferably, these antibodies are immobilized on solid carriers such as test sections or latex particles.

The expression "measuring the expression of Smad1 and/or a substance having Smad1-activating effect" encompasses to detect the presence or absence of the expression of Smad1 and/or a substance having Smad1-activating effect and to quantitate the expression level of Smad1 and/or a substance having Smad1-activating effect.

According to the present invention, it is possible to detect diabetic nephropathy. Briefly, the expression of Smad1 and/or a substance having Smad1-activating effect indicates the onset of diabetic nephropathy. Conventionally, measurement of urinary type IV collagen and urinary albumin has been used in the diagnosis of diabetic nephropathy. The present invention may supersede or supplement such measurement.

Further, according to the present invention, it is possible to evaluate the degree of progress and/or the efficacy of treatment of diabetic nephropathy. Briefly, the expression level of Smad1 and/or a substance having Smad1-activating effect is proportional to the severity of diabetic nephropathy. When the treatment of diabetic nephropathy is effective, the expression level of Smad1 and/or a substance having Smad1-activating effect decreases keeping pace with the recovery of the patient.

Diabetic nephropathy is one of the microangiopathic disorders caused by chronic hyperglycemic conditions. Pathologically, diabetic nephropathy presents thickening of the renal glomerular basement membrane, expansion of the mesangial area and glomerulosclerosis lesions; clinically, diabetic nephropathy presents symptoms such as proteinuria (microalbuminuria), hypertension or edema. Ultimately, diabetic nephropathy patients often develop renal failure. In diabetes, abnormalities such as arteriolosclerosis, denaturing/fibrosing of the tubulointerstitium, etc. are recognized in tissues other than the glomeruli, and these abnormalities make glomerular lesions even worse. Therefore, it is possible to define the pathology in which proteinuria, hypertension and renal function disorders are gradually progressing after a specific period of diabetes, as nephropathy.

Recently, more than 30% of the primary diseases of those patients who newly receive dialysis treatment because of their end-stage renal failure is diabetic nephropathy, and this ratio is still increasing. Further, prognosis of these patients after the introduction of dialysis is not necessarily good, which is a big problem in medical treatment. Therefore, it has become an important problem to elucidate the mechanism of development and progress of diabetic nephropathy and to develop diagnosis and treatment thereof (Japanese Journal of Clinical Medicine vol. 55, 1997 special issue "Diabetes" (1)).

The present invention also provides a kit for detecting diabetic nephropathy, comprising a reagent(s) for measuring the expression of Smad1 and/or a substance having Smad1-activating effect.

Further, the present invention provides a kit for evaluating the degree of progress and/or the efficacy of treatment of diabetic nephropathy, comprising a reagent(s) for measuring the expression of Smad1 and/or a substance having Smad1-activating effect.

Examples of reagents for measuring the expression of Smad1 and/or a substance having Smad1-activating effect include, but are not limited to, a pair of primers capable of amplifying a specific region of the nucleotide sequence of Smad1 mRNA; a pair of primers capable of amplifying a specific region of the nucleotide sequence of the mRNA of a substance having Smad1-activating effect; a probe capable of hybridizing to a part or the entire region of Smad1 mRNA; a probe capable of hybridizing to a part or the entire region of the mRNA of a substance having Smad1-activating effect; an antibody to Smad1; and an antibody to a substance having Smad1-activating effect. These primer pairs and antibodies are as described above.

The kit of the invention may further comprise reverse transcriptase, DNA polymerase, RNase-free water, buffers, control MRNA, control primer pair, dNTP mix, instructions, and so forth (when the kit is intended to measure the expression of Smad1 and/or a substance having Smad1-activating effect at the nuclear acid level using a primer pair).

Alternatively, the kit of the invention may further comprise a transcription buffer, blocking reagent, washing solutions, instructions and so forth (when the kit is intended to measure the expression of Smad1 and/or a substance having Smad1-activating effect by Western blotting).

In another embodiment of the invention, the kit of the invention may further comprise a labeled secondary antibody, substrate (when the secondary antibody is an enzyme and labeled), diluents, reaction terminators, instructions and so forth (when the kit is intended to measure the expression of Smad1 and/or a substance having Smad1-activating effect by ELISA).

In still another embodiment of the invention, the kit of the invention may further comprise a color formers, aqueous hydrogen peroxide, buffers, a dyes for counter-staining, instructions and so forth (when the kit is intended to measure the expression of Smad1 and/or a substance having Smad1-activating effect by immunohistochemical analysis).

2. Method and Kit for Detecting Proliferative Diseases Causing Sclerosis

The present invention provides a method of detecting proliferative diseases causing sclerosis, comprising measuring the expression of at least one substance selected from the group consisting of STAT3, phosphorylated STAT3, Smad1, phosphorylated Smad1, activin receptor-like kinase 1, activin receptor-like kinase 3 and bone morphogenetic proteins in a biological sample.

The term "proliferative diseases causing sclerosis" means diseases where organ sclerosing is observed, and refers to a state where cell proliferation and/or expansion of extracellular matrix is recognized prior to sclerosis or in parallel with sclerosis. Proliferative diseases causing sclerosis include, but are not limited to, renal diseases damaging the glomeruli such as diabetic nephropathy, chronic glomerulonephritis, membranous proliferative glomerulonephritis, focal glomerulosclerosis, light chain disease (L chain deposition disease), lupus nephritis, cryoglobulinemic nephritis, HIV-associated nephritis and purpuric nephritis; hepatic fibrosis; arteriosclerosis; and the like.

Chronic glomerulonephritis is a state of chronic renal disorders, resulting in inflammation and gradual, progressive destruction of the glomeruli. Chronic glomerulonephritis is a syndrome including diseases such as membranous proliferative glomerulonephritis, focal glomerulosclerosis, light chain disease (L chain deposition disease), lupus nephritis, cryoglobulinemic nephritis, HIV-associated nephritis and purpuric nephritis.

Diabetic nephropathy is one of the representative diabetic complications and refers to a state in which renal functions are progressively reduced because of prolonged hyperglycemic conditions caused by diabetes.

Hepatic fibrosis is found in hepatic cirrhosis or chronic hepatitis, and refers to a state in which expansion of the extracellular matrix such as collagen is recognized in places (Disse's spaces) between the hepatic sinusoid wall and the hepatic cords. Hepatic fibrosis is a risk factor for the development of hepatocellular carcinoma, and it is known that progress of fibrosis makes the incidence of hepatocellular carcinoma higher.

Arteriosclerosis, which is a generic term for lesions where the arterial wall becomes thickened or sclerosed, is believed to be chronic inflammatory/proliferative lesions attributable to endothelial cell injuries caused by oxidation stress or the like. When arterial constriction and occlusion occur as a result of progress of arteriosclerosis, rise in blood pressure, myocardial infarction, cerebral infarction, etc. are caused. However, patients have few subjective symptoms prior to organ dysfunction.

The biological sample may be any biological sample as long as at least one substance selected from the group consisting of STAT3, phosphorylated STAT3, Smad1, phosphorylated Smad1, activin receptor-like kinase 1, activin receptor-like kinase 3 and bone morphogenetic proteins is detectable therein. Specific examples of the biological sample which may be used in the invention include renal tissue sections, blood, sera and urine.

STAT3 is one of signal transducer and activator of transcription (STAT) proteins. STAT3 is activated via tyrosine phosphorylation by receptor-associated kinases when various cytokines and growth factors (such as interferon, epithelium growth factor, interleukin 5, interleukin 6, hepatocyte growth factor, leukemia inhibitory factor and bone growth factor 2) have bound to their receptors (phosphorylated STAT).

Phosphorylated Smad1 is a Smad1 which is in an activated state through phosphorylation of its serine residues.

The expression of at least one substance selected from the group consisting of STAT3, phosphorylated STAT3, Smad1, phosphorylated Smad1, activin receptor-like kinase 1, activin receptor-like kinase 3 and bone morphogenetic proteins may be measured at the nucleic acid level (i.e. mRNA expression) and/or the protein level.

With respect to the measurement at the nucleic acid level, total RNA may be extracted from a biological sample, and then the mRNA of at least one substance selected from the group consisting of STAT3, phosphorylated STAT3, Smad1, phosphorylated Smad1, activin receptor-like kinase 1, activin receptor-like kinase 3 and bone morphogenetic proteins may be measured by RT-PCR using a pair of appropriate primers. These primers may be designed so that a specific region in sequences such as the nucleotide sequence for human-derived STAT3 mRNA available as NM_139276 in NCBI Refseq database (SEQ ID NO: 19); the nucleotide sequence for human-derived Smad1 mRNA available as NM_005900 in NCBI Refseq database (SEQ ID NO: 1); the nucleotide sequence for the mRNA of human-derived activin receptor-like kinase 1 available as NM_000020 in NCBI Refseq database (SEQ ID NO: 2); the nucleotide sequence for the mRNA of human-derived activin receptor-like kinase 3 available as NM_004329 in NCBI Refseq database (SEQ ID NO: 20); the nucleotide sequence for BMP2 mRNA available as ACCESSION NM_001200 VERSION NM_001200.1 in GenBank database (SEQ ID NO: 3); and the nucleotide sequence for BMP4 mRNA available as ACCESSION NM_001202 VERSION NM_001202.2 in GenBank database (SEQ ID NO: 4) is amplified specifically. Examples of nucleotide sequences for appropriate primer pairs are as described below.

RT-PCR to amplify STAT3 mRNA specifically:

```
Forward primer:
5'-agatgctcactgcgctgga-3'          (SEQ ID NO: 21)

Reverse primer:
5'-tccaatgcaggcaatctgtt-3'         (SEQ ID NO: 22)
```

RT-PCR to amplify Smad1 mRNA specifically:

```
Forward primer:
5'-ACTACCACCACGGCTTTCAC-3'         (SEQ ID NO: 5)

Reverse primer:
5'-AATAGGATTGTGGGGTGAGC-3'         (SEQ ID NO: 6)
```

RT-PCR to amplify ALK1 mRNA specifically:

```
Forward primer:
5'-ccgtcaagatcttctcctcg-3'         (SEQ ID NO: 7)

Reverse primer:
5'-tcatgtctgaggcgatgaag-3'         (SEQ ID NO: 8)
```

RT-PCR to amplify ALK3 mRNA specifically:

```
Forward primer:
5'-tggcactgggatgaaatca-3'          (SEQ ID NO: 23)

Reverse primer:
5'-tggttacataaattggtccga-3'        (SEQ ID NO: 24)
```

RT-PCR to amplify BMP2 mRNA specifically:

```
Forward primer:
5'-cccagcgtgaaaagagagac-3'         (SEQ ID NO: 9)

Reverse primer:
5'-gagaccgcagtccgtctaag-3'         (SEQ ID NO: 10)
```

RT-PCR to amplify BMP4 mRNA specifically:

```
Forward primer:
5'-tgagcctttccagcaagttt-3'         (SEQ ID NO: 11)

Reverse primer:
5'-cttccccgtctcaggtatca-3'         (SEQ ID NO: 12)
```

Alternatively, total RNA may be extracted from a biological sample, and then the mRNA of at least one substance selected from the group consisting of STAT3, phosphorylated STAT3, Smad1, phosphorylated Smad1, activin receptor-like kinase 1, activin receptor-like kinase 3 and bone morphogenetic proteins may be measured by Northern hybridization using an appropriate probe. The appropriate probe may be designed based on sequences such as the nucleotide sequence for human-derived STAT3 MRNA available as NM_139276 in NCBI Refseq database (SEQ ID NO: 19); the nucleotide sequence for human-derived Smad1 mRNA available as NM_005900 in NCBI Refseq database (SEQ ID NO: 1); the nucleotide sequence for the mRNA of human-derived activin receptor-like kinase 1 available as NM_000020 in NCBI Refseq database (SEQ ID NO: 2); the nucleotide sequence for the mRNA of human-derived activin receptor-like kinase 3 available as NM_004329 in NCBI Refseq database (SEQ ID NO: 20); the nucleotide sequence for BMP2 mRNA available as ACCESSION NM_001200 VERSION NM_001200.1 in GenBank database (SEQ ID NO: 3); and the nucleotide sequence for BMP4 mRNA available as ACCESSION NM_001202 VERSION NM_001202.2 in GenBank database (SEQ ID NO: 4) so that it specifically hybridizes to a part or the entire region of such sequences. The probe may be labeled with a substance such as $^{32}$p.

With respect to the measurement at the protein level, at least one substance selected from the group consisting of STAT3, phosphorylated STAT3, Smad1, phosphorylated Smad1, activin receptor-like kinase 1, activin receptor-like kinase 3 and bone morphogenetic proteins may be measured by a method such as Western blotting, ELISA or immunohistochemical analysis using, for example, antibodies to at least one substance selected from the group consisting of STAT3, phosphorylated STAT3, Smad1, phosphorylated Smad1, activin receptor-like kinase 1, activin receptor-like kinase 3 and bone morphogenetic proteins. These antibodies may be labeled with a fluorescent dye, enzyme, heavy metal, or the like (direct method). Alternatively, instead of labeling these antibodies, antibodies (secondary antibodies) specific to these antibodies (primary antibodies) may be labeled with a fluorescent dye, enzyme, heavy metal, or the like (indirect method). Preferably, these antibodies are immobilized on solid carriers such as test sections or latex particles.

The expression "measuring the expression of at least one substance selected from the group consisting of STAT3, phosphorylated STAT3, Smad1, phosphorylated Smad1, activin receptor-like kinase 1, activin receptor-like kinase 3 and bone morphogenetic proteins" encompasses to detect the presence or absence of the expression of at least one substance selected from the group consisting of STAT3, phosphorylated STAT3, Smad1, phosphorylated Smad1, activin receptor-like kinase 1, activin receptor-like kinase 3 and bone morphogenetic proteins and to quantitate the expression level of at least one substance selected from the group consisting of STAT3, phosphorylated STAT3, Smad1, phosphorylated Smad1, activin receptor-like kinase 1, activin receptor-like kinase 3 and bone morphogenetic proteins.

According to the present invention, it is possible to detect proliferative diseases causing sclerosis. Briefly, the expression of at least one substance selected from the group consisting of STAT3, phosphorylated STAT3, Smad1, phosphorylated Smad1, activin receptor-like kinase 1, activin receptor-like kinase 3 and bone morphogenetic proteins indicates the onset of proliferative diseases causing sclerosis. Conventionally, measurement of urinary type IV collagen and urinary albumin has been used in the diagnosis of renal diseases damaging the glomeruli (such as diabetic nephropathy and chronic glomerulonephritis). The present invention may supersede or supplement such measurement.

Further, according to the present invention, it is possible to evaluate the degree of progress and/or the efficacy of treatment of proliferative diseases causing sclerosis. Briefly, the expression level of at least one substance selected from the group consisting of STAT3, phosphorylated STAT3, Smad1, phosphorylated Smad1, activin receptor-like kinase 1, activin receptor-like kinase 3 and bone morphogenetic proteins is proportional to the severity of proliferative diseases causing sclerosis. When the treatment of proliferative diseases causing sclerosis is effective, the expression level of at least one substance selected from the group consisting of STAT3, phosphorylated STAT3, Smad1, phosphorylated Smad1, activin receptor-like kinase 1, activin receptor-like kinase 3 and bone morphogenetic proteins decreases keeping pace with the recovery of the patient.

The present invention also provides a kit for detecting proliferative diseases causing sclerosis, comprising a reagent(s) for measuring the expression of at least one substance selected from the group consisting of STAT3, phosphorylated STAT3, Smad1, phosphorylated Smad1, activin receptor-like kinase 1, activin receptor-like kinase 3 and bone morphogenetic proteins.

Further, the present invention provides a kit for evaluating the degree of progress and/or the efficacy of treatment of proliferative diseases causing sclerosis, comprising a reagent(s) for measuring the expression of at least one substance selected from the group consisting of STAT3, phosphorylated STAT3, Smad1, phosphorylated Smad1, activin receptor-like kinase 1, activin receptor-like kinase 3 and bone morphogenetic proteins.

Proliferative diseases causing sclerosis are as described above.

Examples of reagents for measuring the expression of at least one substance selected from the group consisting of STAT3, phosphorylated STAT3, Smad1, phosphorylated Smad1, activin receptor-like kinase 1, activin receptor-like kinase 3 and bone morphogenetic proteins include, but are not limited to, a pair of primers capable of amplifying a specific region of the nucleotide sequence of the mRNA of at least one substance selected from the group consisting of STAT3, phosphorylated STAT3, Smad1, phosphorylated Smad1, activin receptor-like kinase 1, activin receptor-like kinase 3 and bone morphogenetic proteins; a probe capable of hybridizing to a part or the entire region of the mRNA of at least one substance selected from the group consisting of STAT3, phosphorylated STAT3, Smad1, phosphorylated Smad1, activin receptor-like kinase 1, activin receptor-like kinase 3 and bone morphogenetic proteins; and an antibody to at least one substance selected from the group consisting of STAT3, phosphorylated STAT3, Smad1, phosphorylated Smad1, activin receptor-like kinase 1, activin receptor-like kinase 3 and bone morphogenetic proteins. These primer pairs and antibodies are as described above.

The kit of the invention may further comprise reverse transcriptase, DNA polymerase, RNase-free water, buffers, control mRNA, control primer pair, dNTP mix, instructions, and so forth (when the kit is intended to measure the expression of at least one substance selected from the group consisting of STAT3, phosphorylated STAT3, Smad1, phosphorylated Smad1, activin receptor-like kinase 1, activin receptor-like kinase 3 and bone morphogenetic proteins at the nuclear acid level using a primer pair).

Alternatively, the kit of the invention may further comprise a transcription buffer, blocking reagent, washing solutions, instructions and so forth (when the kit is intended to measure the expression of at least one substance selected from the group consisting of STAT3, phosphorylated STAT3, Smad1, phosphorylated Smad1, activin receptor-like kinase 1, activin receptor-like kinase 3 and bone morphogenetic proteins by Western blotting).

In another embodiment of the invention, the kit of the invention may further comprise a labeled secondary antibody, substrate (when the secondary antibody is an enzyme and labeled), diluents, reaction terminators, instructions and so forth (when the kit is intended to measure the expression of at least one substance selected from the group consisting of STAT3, phosphorylated STAT3, Smad1, phosphorylated Smad1, activin receptor-like kinase 1, activin receptor-like kinase 3 and bone morphogenetic proteins by ELISA).

In still another embodiment of the invention, the kit of the invention may further comprise a color formers, aqueous hydrogen peroxide, buffers, a dyes for counter-staining, instructions and so forth (when the kit is intended to measure the expression of at least one substance selected from the group consisting of STAT3, phosphorylated STAT3, Smad1, phosphorylated Smad1, activin receptor-like kinase 1, activin receptor-like kinase 3 and bone morphogenetic proteins by immunohistochemical analysis).

3. Drugs and Pharmaceutical Compositions

The present invention provides a prophylactic and/or therapeutic agent for proliferative diseases causing sclerosis, comprising as an active ingredient a substance having an inhibitory effect on the expression of at least one substance selected from the group consisting of STAT3, phosphorylated STAT3, Smad1 and phosphorylated Smad1.

Proliferative diseases causing sclerosis are as described above.

Further, the present invention provides a drug inhibiting the increase of extracellular matrix, comprising as an active ingredient a substance having an inhibitory effect on the expression of at least one substance selected from the group consisting of STAT3, phosphorylated STAT3, Smad1 and phosphorylated Smad1. Extracellular matrix is a stable biostructure surrounding cells within animal tissues which is an assembly of biopolymers synthesized by cells and secreted/accumulated out of the cells. Extracellular matrix also includes those structures that were synthesized/secreted by cultured cells and deposited around the cells. Extracellular matrix is found abundantly in connective tissues. The basement membrane is also a type of extracellular matrix.

Further, the present invention provides a drug inhibiting the expression of $\alpha 1$ type IV collagen, comprising as an active ingredient a substance having an inhibitory effect on the expression of at least one substance selected from the group consisting of STAT3, phosphorylated STAT3, Smad1 and phosphorylated Smad1.

These drugs may be used as pharmaceuticals or as reagents for use in experiments.

Example of the substance having an inhibitory effect on the expression of at least one substance selected from the group consisting of STAT3, phosphorylated STAT3, Smad1 and phosphorylated Smad1 include, but are not limited to, antisense oligonucleotides to Smad1 (one example of such nucleotide sequences is given in SEQ ID NO: 13); SANE (Smad1 Antagonistic Effector) (Raju G P et al., J Biol Chem. 2003 Jan 3;278(1):428-437); anti-PDGF $\beta$ receptor antibody (APB5); and antisense oligonucleotides to STAT3. Any of the proteins may be produced by the recombinant DNA technology in *Escherichia coli,* yeast, insect cells, animal cells or cell-free protein synthesis systems. Antisense oligonucleotides to Smad1 or STAT3 may be synthesized by known methods in commercial DNA synthesizers. APB5, which is anti-mouse PDGFR-$\beta$ antibody, may be prepared as follows. Briefly, a cDNA fragment corresponding to the extracellular domain of mouse PDGFR-$\beta$ was inserted into CD4Rg vector. A fusion protein with human IgG1 (PDGFR-$\beta$/Human IgG1) was expressed in COS-1 cell strain. The fusion protein was purified from the culture supernatant and used for immunizing Wistar rats. Fusion cells were prepared using splenic cells from the rats and myeloma cells, followed by selection of cells producing antibodies to PDGFR-$\beta$. Not only APB5 but also other anti-PDGFR-$\beta$ specific antibodies that can be prepared by known methods may be used in the same manner as APB5 is used.

One substance having an inhibitory effect on the expression of at least one substance selected from the group consisting of STAT3, phosphorylated STAT3, Smad1 and phosphorylated Smad1 may be used. Alternatively, a plurality of such substances may be used in combination.

The substance having an inhibitory effect on the expression of at least one substance selected from the group consisting of STAT3, phosphorylated STAT3, Smad1 and phosphorylated Smad1 may be administered alone or together with pharmacologically acceptable carriers, diluents or excipients in appropriate forms of pharmaceutical compositions, to mammals (e.g. human, rabbit, dog, cat, rat, mouse, etc.) orally or parenterally. Dose levels may vary depending upon the patient to be treated, the target disease, symptoms, administration route, and so on. However, in the administration to adult patients, it is convenient to inject a substance having an inhibitory effect on the expression of at least one substance selected from the group consisting of STAT3, phosphorylated STAT3, Smad1 and phosphorylated Smad1 (e.g., SANE) intravenously at a dose of about 10-100 mg/kg body weight, preferably about 60-40 mg/kg body weight per administration about once or twice a month; preferably, the above dose is administered for two or three consecutive days at the beginning of treatment. In other parenteral administration and oral administration, similar dose levels may be used. If symptoms are particularly heavy, the dose may be increased accordingly.

Compositions for oral administration include solid or liquid preparations such as tablets (including sugar-coated tablets and film-coated tablets), pills, granules, dispersants, capsules (including soft capsules), syrups, emulsions and suspensions. These compositions may be prepared according to conventional methods and may contain carriers, diluents or excipients conventionally used in the field of medicine manufacture. For example, lactose, starch, sucrose, magnesium stearate and the like are used as carriers or excipients for tablets.

Compositions for parenteral administration include, for example, injections and suppositories. Injections include intravenous injections, subcutaneous injections, intradermal injections, muscle injections, instilment injections, etc. Such injections may be prepared by conventional methods, i.e., by dissolving, suspending or emulsifying a substance having an inhibitory effect on the expression of Smad1 in an aseptic, aqueous or oily liquid conventionally used in injections. Examples of aqueous liquids for injection include physiological saline and isotonic solutions containing glucose and other auxiliary agents. They may be used in combination with a suitable auxiliary solubilizer such as alcohol (e.g. ethanol), polyalcohol (e.g. propylene glycol, polyethylene glycol), nonionic surfactant [e.g. Polysorbate 80™, HCO-50 (polyoxyethylene (50 mol) adduct of hydrogenated castor oil)], etc. Examples of oily liquids for injection include sesame oil and soybean oil. They may be used in combination with an auxiliary solubilizer such as benzyl benzoate, benzyl alcohol, etc. Usually, the prepared injections are filled in appropriate ampoules. Suppositories for administration into rectum may be prepared by mixing a substance having an inhibitory effect on the expression of Smad1 with a conventional suppository base.

It is convenient to formulate the above-described pharmaceutical compositions for oral or parenteral administration into unit dosage forms that would give an appropriate dose of the active ingredient. Examples of such unit dosage forms include tablets, pills, capsules, injections (ampoules), and suppositories.

The above-described pharmaceutical compositions may contain other active ingredients as long as they do not produce undesirable interaction when combined with the substance having an inhibitory effect on the expression of at least one substance selected from the group consisting of STAT3, phosphorylated STAT3, Smad1 and phosphorylated Smad1.

When the substance having an inhibitory effect on the expression of at least one substance selected from the group consisting of STAT3, phosphorylated STAT3, Smad1 and phosphorylated Smad1 is an antisense oligonucleotide to Smad1 or STAT3, the antisense oligonucleotide may be introduced into the patient or cells of the patient by known methods of gene transfer. For example, a method in which an antisense oligonucleotide to Smad1 or STAT3 is enclosed in liposomes and then taken into cells ("Lipidic vector systems for gene transfer" (1997) R. J. Lee and L. Huang Crit. Rev. Ther. Drug Carrier Syst 14, 173-206; Nakanishi M. et al., "Protein, Nucleic Acid and Enzyme" Vol. 44, No. 11, 1590-1596(1999)); the calcium phosphate method, electroporation, lipofection, microinjection, a method using a gene gun, and so on may be used. When an antisense oligonucleotide to Smad1 or STAT3 is introduced into cells, a part of the cells at the diseased site may be taken out and then returned to the original tissue after in vitro gene transfer. Alternatively, the antisense oligonucleotide may be introduced directly into the tissue of the diseased site.

Pharmaceutical compositions comprising an antisense oligonucleotide to Smad1 or STAT3 as an active ingredient may comprise, if necessary, pharmaceutically acceptable carriers (e.g. diluents such as physiological saline or buffer). Administration of the pharmaceutical composition may be continued until the efficacy of treatment is recognized or until amelioration of conditions is achieved at appropriate dose, with an appropriate administration method and at appropriate frequency, depending on the severity of the target disease and the responsiveness of the patient body.

4. Method and Kit for Identifying Substances Effective in Preventing and/or Treating Proliferative Diseases Causing Sclerosis; Method and Kit for Identifying Substances Effective in Inhibiting the Increase of Extracellular Matrix; and Method and Kit for Identifying Substances Effective in Inhibiting the Expression of α1 Type IV Collagen The present invention provides a method of identifying substances effective in preventing and/or treating proliferative diseases causing sclerosis, comprising judging whether or not a test substance inhibits the expression of at least one substance selected from the group consisting of STAT3, phosphorylated STAT3, Smad1 and phosphorylated Smad1.

Proliferative diseases causing sclerosis are as described above.

Further, the present invention provides a method and a kit for identifying substances effective in inhibiting the increase of extracellular matrix, comprising judging whether or not a test substance inhibits the expression of at least one substance selected from the group consisting of STAT3, phosphorylated STAT3, Smad1 and phosphorylated Smad1.

Still further, the present invention provides a method and a kit for identifying substances effective in inhibiting the expression of α1 type IV collagen, comprising judging whether or not a test substance inhibits the expression of at least one substance selected from the group consisting of STAT3, phosphorylated STAT3, Smad1 and phosphorylated Smad1.

Hereinbelow, one embodiment of the above-described method will be described.

First, cells capable of expressing at least one substance selected from the group consisting of STAT3, phosphorylated STAT3, Smad1 and phosphorylated Smad1 are prepared. Any cell capable of expressing at least one substance selected from the group consisting of STAT3, phosphorylated STAT3, Smad1 and phosphorylated Smad1 may be used. Specific examples which may be used in the invention include mesangial cells derived from renal glomeruli of animals (e.g. those disclosed in Reference S1 described later) and vascular smooth muscle cells.

Cells capable of expressing at least one substance selected from the group consisting of STAT3, phosphorylated STAT3, Smad1 and phosphorylated Smad1 are cultured in the presence and the absence of a test substance, followed by measurement of the at least one substance selected from the group consisting of STAT3, phosphorylated STAT3, Smad1 and phosphorylated Smad1. Examples of the test substance include, but are not limited to, peptides, proteins, non-peptidic compounds, synthetic compounds, fermentation products, cell extracts, plant extracts and animal tissue extracts. These substances may be either novel substances or known substances. The culturing of the cell capable of expressing at least one substance selected from the group consisting of STAT3, phosphorylated STAT3, Smad1 and phosphorylated Smad1 may be performed under culture conditions suitable for the relevant cell. For example, mesangial cells derived from mouse renal glomeruli (Reference S1 described later) may be cultured as described in Example 1. The method of measuring the expression of STAT3 and Smad1 is as described above.

The expression of phosphorylated STAT3 and phosphorylated Smad1 may be measured by immunostaining using anti-phosphorylated STAT3 antibody (Santa Cruz Biotechnology) and anti-phosphorylated Smad1 antibody (Calbiochem), respectively, as a primary antibody.

The expression level of at least one substance selected from the group consisting of STAT3, phosphorylated STAT3, Smad1 and phosphorylated Smad1 when cells were cultured in the presence of a test substance is compared with the expression level of the at least one substance selected from the group consisting of STAT3, phosphorylated STAT3, Smad1 and phosphorylated Smad1 when cells were cultured in the absence of the test substance. When the former is less than the latter, the test substance is judged effective in preventing and/or treating proliferative diseases causing sclerosis; or the test substance is judged effective in inhibiting the increase of extracellular matrix; or the test substance is judged effective in inhibiting the expression of α1 type IV collagen. On the contrary, when the former is equivalent to the latter, or when the former is more than the latter, the test substance is judged ineffective in preventing and/or treating proliferative diseases causing sclerosis; or the test substance is judged ineffective in inhibiting the increase of extracellular matrix; or the test substance is judged ineffective in inhibiting the expression of α1 type IV collagen.

The present invention also provides a kit for identifying substances effective in preventing and/or treating proliferative diseases causing sclerosis, comprising a reagent(s) for measuring the expression of at least one substance selected from the group consisting of STAT3, phosphorylated STAT3, Smad1 and phosphorylated Smad1.

Further, the present invention provides a kit for identifying substances effective in inhibiting the increase of extracellular matrix, comprising a reagent(s) for measuring the expression of at least one substance selected from the group consisting of STAT3, phosphorylated STAT3, Smad1 and phosphorylated Smad1.

Still further, the present invention provides a kit for identifying substances effective in inhibiting the expression of α1 type IV collagen, comprising a reagent(s) for measuring the expression of at least one substance selected from the group consisting of STAT3, phosphorylated STAT3, Smad1 and phosphorylated Smad1.

Proliferative diseases causing sclerosis are as described above.

Examples of reagents for measuring the expression of STAT3 or Smad1 include, but are not limited to, primer pairs capable of specifically amplifying a specific region of the nucleotide sequence of STAT3 mRNA or Smad1 MRNA, probes capable of specifically hybridizing to a part or the entire region of STAT3 mRNA or Smad1 mRNA, and antibodies to STAT3 or Smad1. These primer pairs and antibodies are as described above.

Examples of reagents for measuring the expression of phosphorylated STAT3 or phosphorylated Smad1 include, but are not limited to, anti-phosphorylated STAT3 antibody (Santa Cruz Biotechnology) and anti-phosphorylated Smad1 antibody (Calbiochem). These antibodies are as described above.

The kit of the invention may further comprise reverse transcriptase, DNA polymerase, RNase-free water, buffers, control mRNA, control primer pair, dNTP mix, instructions, and so forth (when the kit is intended to measure the expression of STAT3 or Smad1 at the nuclear acid level using a primer pair).

Alternatively, the kit of the invention may further comprise a transcription buffer, blocking reagent, washing solutions, instructions and so forth (when the kit is intended to measure the expression of STAT3 or Smad1 by Western blotting).

In another embodiment of the invention, the kit of the invention may further comprise a labeled secondary antibody, substrate (when the secondary antibody is an enzyme and labeled), diluents, reaction terminators, instructions and so forth (when the kit is intended to measure the expression of STAT3, phosphorylated STAT3, Smad1 or phosphorylated Smad1 by ELISA).

In still another embodiment of the invention, the kit of the invention may further comprise color formers, aqueous hydrogen peroxide, buffers, dyes for counter-staining, instructions and so forth (when the kit is intended to measure the expression of STAT3, phosphorylated STAT3, Smad1 or phosphorylated Smad1 by immunohistochemical analysis).

Hereinbelow, the present invention will be described specifically with reference to the following Examples. These Examples are provided only for the purpose of illustrating the present invention and are not intended to limit the scope of the invention.

EXAMPLE 1

Figure 1A:
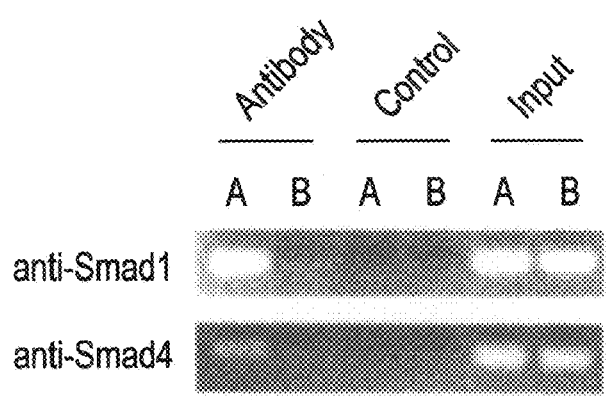
FIG. 1 shows activation of Col4 promoter by Smad1. (A): Chromatin immunoprecipitation was carried out using cultured mesangial cells in the presence of AGEs or BSA (control), using the indicated antibodies. PCR was performed using primers for CIV-1 motif. The results of one experiment out of three independent experiments are shown. (B): Cells were cotransfected with a vector containing CIV-1-lacZ reporter plasmid together with either a wild type Smad1 vector or a mock vector (Mock), and CMV-LUC as an internal control. Cell extracts were analyzed by Western blotting using anti-Smad1 and anti-pSmad1 antibodies. The results of one experiment out of three independent experiments are shown. (C): After 48 hours, cultured cells were lysed, followed by measurement of β-galactosidase and luciferase activities. Values are the averages of triplicate determinations with SD.
Figure 1B:
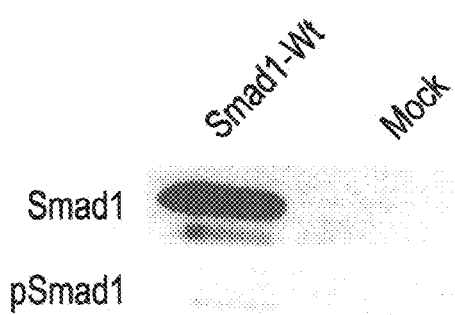
Figure 1C:
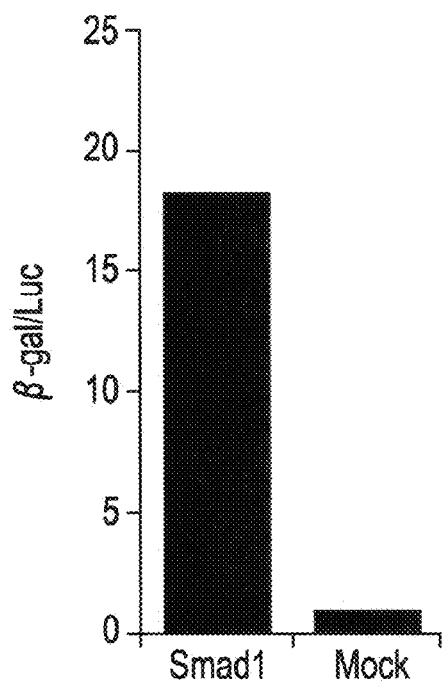

To identify the protein which binds to the CIV site in the promoter region of the mouse Col4 gene, the present inventors constructed a cDNA library from mouse mesangial cells treated with AGEs. Here, the inventors used a yeast one-hybrid system to isolate a clone that encodes a specific transcription factor from the library, and then identified this clone as encoding Smad1. To confirm the binding of Smad1 to the Col4 promoter in vivo, the inventors performed a chromatin immunoprecipitation (CHIP) assay. Precipitated DNA was purified, and the promoter region of the Col4 gene was detected by PCR. Anti-Smad1 antibody precipitated chromatin containing the CIV-1 site from cells stimulated with AGEs (FIG. 1A). In contrast, no precipitation was observed in BSA-exposed cells. The inventors found that Smad4 also binds to the CIV-1 site (FIG. 1A). Next, the inventors examined the transcriptional activity of the Col4 gene by a reporter assay. The inventors constructed a vector by linking the CIV-1 promoter upstream of LacZ, and then cotransfected into COS7 cells with a wild-type Smad1 vector. First, the inventors confirmed the expression of Smad1 by Western blot analysis (FIG. 1B). Phosphorylated Smad1 (pSmad1) was detected in culture supernatant of cells that have been tranfected with the wild-type Smad1 vector. Cotransfection of the wild-type Smad1 resulted in a 18-fold increase in β-galactosidase activity compared with that activity in cells cotransfected with mock vector (Mock) (FIG. 1C). β-galactosidase activity was corrected with luciferase activity, and the P-galactosidase activity in cells cotransfected with the mock vector was taken as the standard. Mock had no effect on the β-galactosidase activity in the cells cotransfected with it. These results suggest that Smad1 is certainly involved in the induction of Col4 gene transcription. Thus, Smad1 transcriptionally regulates the Col4 gene.

Figure 2A:
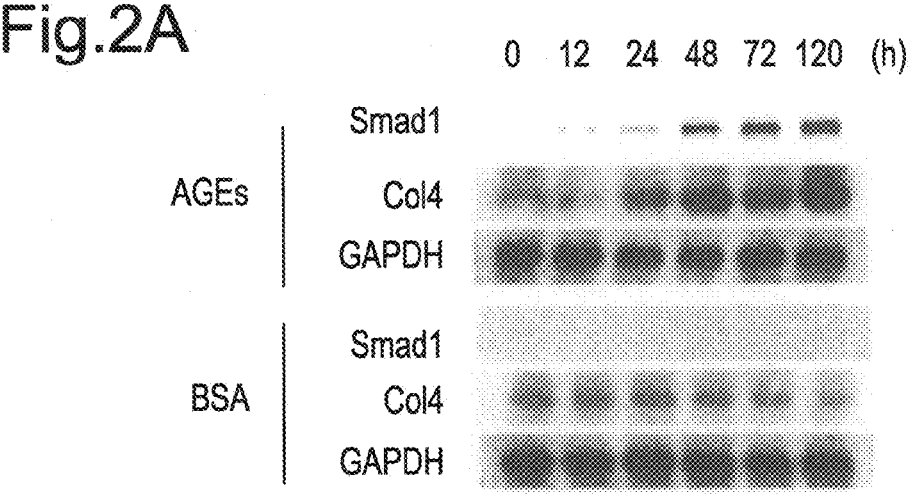
FIG. 2 shows Smad1 expression changing dynamically on exposure to AGEs. (A): RNase protection assay was performed to examine the time course of Smad1 and Col4 MRNA expressions in mesangial cells treated with AGEs or BSA. Continuous exposure to AGEs promotes Smad1 expression continuously in parallel with increase in Col4 expression. The results of one experiment out of three independent experiments are shown. (B): Immunofluorescence photographs of mesangial cells cultured for 72 hr or 120 hr in the presence of AGEs or BSA. Data from one of three independent experiments are shown. (C): Smad1 and pSmad1 were analyzed by Western blotting in cells cultured for 72 hr in the presence of AGEs or BSA. Data from one of three independent experiments are shown.
Figure 2B:
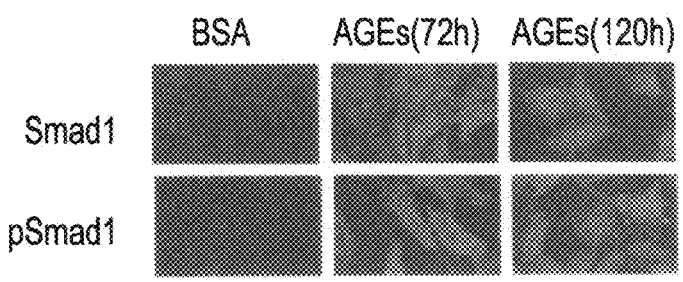
Figure 2C:

To determine whether Smad1 is transcriptionally upregulated by AGEs, the inventors examined the expression of Smad1 in mesangial cells with or without AGEs stimulation. The levels of Smad1 mRNA increased in a time-dependent manner (FIG. 2A). Similarly, the levels of Col4 mRNA increased in parallel with the upregulation of Smad1 transcription. In the presence of BSA, however, no change was detected in the expression of Smad1 mRNA or Col4 mRNA. Smad1 is known to be phosphorylated and translocated into the nucleus where it participates in the transcriptional regulation of target genes (11) (12). Therefore, the inventors next examined the issue of whether the phosphorylation and translocation of Smad1 is affected by AGEs treatment in mesangial cells (FIG. 2B). Consistent with the results on mRNA, Smad1 and pSmad1 were distributed throughout mesangial cells with a preferential cytoplasmic localization after a 72-hr incubation in the presence of AGEs. Furthermore, nuclear accumulation of Smad1 and pSmad1 in response to AGEs was observed in the cells 120 hours after AGEs stimulation, while BSA-treatment led to little expression of Smad1 and pSmad1. Similarly, both Smad1 and pSmad1 were detected in extracts from AGEs-treated cells, but not in extracts from BSA-treated cells (FIG. 2C). These findings indicate that the regulation of Col4 is correlated with the expression of Smad1 under AGEs exposure.

Figure 3A:
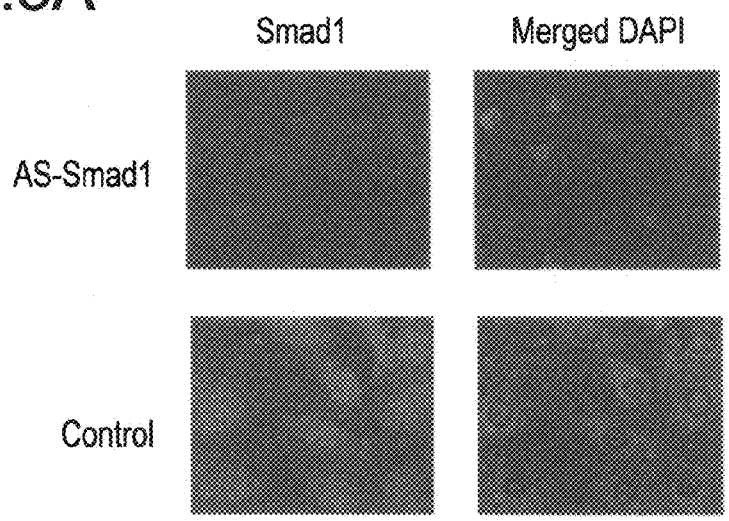
FIG. 3 shows the effect of an antisense oligo specific to Smad1 in mesangial cells. (A): After 72 hr-incubation with AGEs, mesangial cells were incubated for 16 hr in a medium containing an antisense oligo to Smad1 or 4-mismatch oligo (control). The antisense oligo-treated mesangial cells were immunofluorescently stained with anti-Smad1 antibody (green), and further stained with DAPI (blue). Data from one of three representative experiments are shown. (B): The antisense oligo to Smad1 or 4-mismatch oligo (control) was introduced into mesangial cells treated with AGEs. Data from one of three independent experiments are shown. (C): The antisense oligo to Smad1 inhibits the upregulation of Smad1 expression and, at the same time, the upregulation of Col4 expression. Data from one of three independent experiments are shown.
Figure 3B:
Figure 3C:
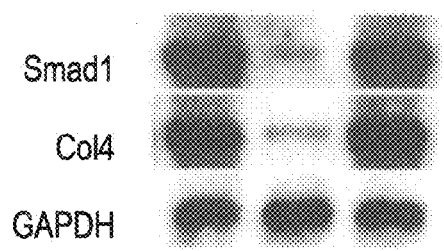
Figure 4:
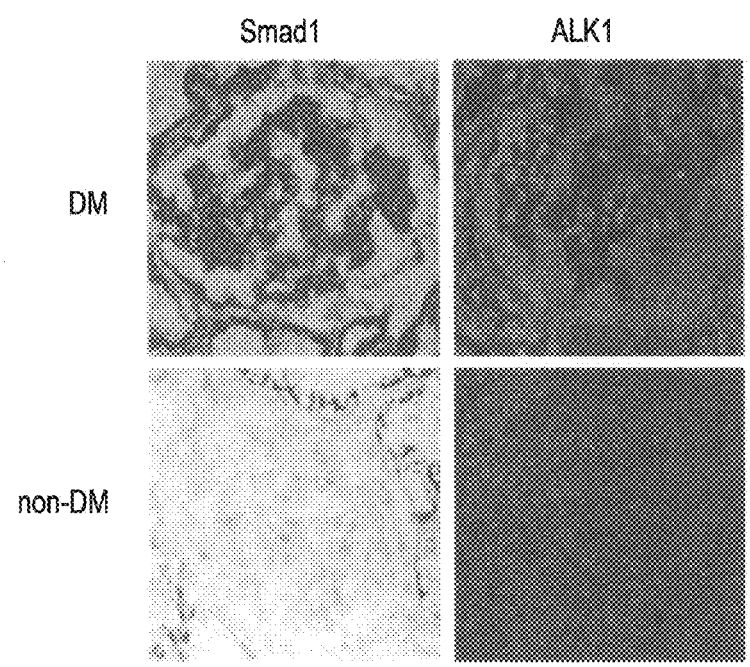
FIG. 4 shows the detection of Smad1 and ALK1 expressions in human patients with diabetic nephropathy. Glomeruli from 5 diabetic patients arid 3 non-diabetic patients were immunohistochemically stained with anti-Smad1 and anti-ALK1 antibodies. Smad1 and ALK1 expressions were markedly detectable in the glomeruli of diabetic patients, but not detected in non-diabetic patients. All sections were counterstained with hematoxylin. Magnification is ×400 for all photographs.

To examine the importance of Smad1 in the signaling pathway mediating AGEs-induced overexpression of Col4, the inventors specifically inhibited this pathway with an antisense gene (AS). The AGEs-mediated induction of Smad1 was completely abolished in the presence of the antisense gene, but not in the presence of a control oligo (4-mismatch) (FIG. 3A and 3B). The overexpression of Col4 was remarkably attenuated by the inhibition of Smad1. Smad1 mismatch oligo (control) had no effect on Col4 expression (FIG. 3C). These data indicate that Smad1 plays a critical role in the regulation of Col4 expression. Development and progress of diabetic nephropathy in diabetic patients is a huge clinical problem associated with morbidity and mortality. It is clear that in the current therapy, optimal glycemic control can postpone the development and progress of diabetic nephropathy but can not prevent this disease (1) (2). The antisense oligo to Smad1 remarkably attenuates the AGEs-mediated overproduction of Col4. These findings suggest that blockade of Smad1 signaling may prevent ECM production in mesangial cells in diabetic nephropathy. This effect was observed under prolonged AGEs stimulation. Therefore, Smad1 may be a novel therapeutic target in diabetic complications and be useful in combination with the current therapy. To further elucidate the mechanism of Smad1 expression after AGEs treatment, the inventors investigated the expression of activin receptor-liked kinase1 (ALK1) in mesangial cells. ALK1 is one of the TGF-β receptor family proteins and phosphorylates Smad1 and Smad5 specifically. ALK1 is highly expressed in vascular endothelial cells (13) (14), and may be essential for vascular maturation and stabilization (15) (16). Mutations of ALK1 results in human hereditary hemorrhagic telangiectasia (HHT) type II, also known as Osler-Rendu-Weber syndrome (17). Recent reports show that ALK1 mediates signals from TGF-β through Smad1 to modulate TGF-β-responsive genes (18) (19). The inventors were able to detect an increase in ALK1 expression in AGEs-treated mesangial cells at both mRNA and protein levels, using an RNase protection assay and Western blot analysis, respectively (data not shown). Finally, the inventors investigated the glomerular expression of Smad1 and ALK1 in human diabetic nephropathy. Indirect fluorescent antibody technique was carried out on renal biopsies (diabetic nephropathy) and on normal kidney tissue. Glomerular immunoreactivities to Smad1 and ALK1 antibodies were proportionate to the severity of sclerotic lesions in glomeruli with diabetic nephropathy: on the other hand, immunoreactive signals were nearly absent in normal glomeruli (FIG. 4). These histological observations suggest that the ALK1/Smad1 signaling pathway is linked to the upregulation of Col4. Since diabetic nephropathy in human is a process that progresses slowly over many years, it is likely that a very detailed evaluation of this phenomenon will be required to elucidate the interaction of Smad1 and ALK1 in this condition.

Targeted gene disruption of Smad1 gene in mice results in embryonic lethality. This suggests that Smad1 plays critical roles in early embryogenesis (20). However, because of the early embryonic lethality, little is known about the role of Smad1 in vivo, particularly in the adult. Smad1 is well known to transduce BMP signals (12) and to be especially important in the development of kidney (21). However, Smad1 expression is not detected in glomeruli in adult mice (22). The inventors demonstrated for the first time that AGEs induce the expression of Smad1 in adult mouse glomeruli. The inventors observed that chronic exposure to AGEs, inducing sustained increase in Smad1 expression, leads to Col4 overproduction and suggested that Smad1 is a critical modulator in diabetic conditions. Since AGEs are significantly involved in diabetic complications, the results obtained by the inventors may give valuable insights into any disease and condition where collagen deposition occurs, such as diabetes or aging. Changes in GBM structure occur very early in diabetic nephropathy, even before microalbuminuria is apparent. Therefore, in diabetic nephropathy, Smad1 may be the earliest indicator of renal dysfunction. Recent reports demonstrated that ALK1 mediates signals from TGF-β via Smad1 (18, 19). Therefore, the inventors investigated the expression of ALK1 in mouse mesangial cells and human kidney tissues. As a result, the inventors demonstrated that ALK1 and Smad1 are expressed in renal glomeruli in response to the progress of diabetic conditions. These results lead to the development of novel therapeutic strategies for the treatment of diabetic complications in various organs by suppressing the pathologically activated production of collagen (1). This confirms that sustained hyperglycemia, reflected by an increase in AGEs, is a prerequisite for the development of long-term diabetic complications (23, 24). Glycation leads ultimately to increased crosslinking of collagen resulting in increased arterial stiffness (25). Moreover, the correlation between AGEs and the development of diabetic complications and arteriosclerosis has been recently emphasized by studies using specific AGEs inhibitors (26, 27). Although Col4 is the principal component of the vascular basement membrane, the cellular and molecular mechanisms involved in the upregulation of Col4 in diabetic conditions or aging are as yet poorly understood. The inventors here elucidate that Smad1 directly regulates Col4 gene expression. Accordingly, the inventors speculate that the ALK1/Smad1 signaling pathway may mediate the development of arteriosclerosis, both in diabetic patients and in the aged, by inducing an overproduction of ECM. Further work is in progress to clarify the role of the ALK1/Smad1 signaling pathway in diabetic or aged animal models.

Further, mRNA expression levels in mesangial cells cultured in the presence of AGEs were compared with corresponding mRNA expression levels in mesangial cells cultured in the presence of BSA (FIG. 5). In the presence of AGEs, transcription of BMPRII and BMP4 was remarkably enhanced. Although no big change was recognized in Smad1 transcription level, big changes in its transcription level are difficult to perceive because Smad1 is a transcription factor. Besides, it is believed that translocation from the cytoplasm to the nucleus and phosphorylation (which are important for the effect of a transcription factor) are not reflected in the experimental results using microarrays.

Figure 6:
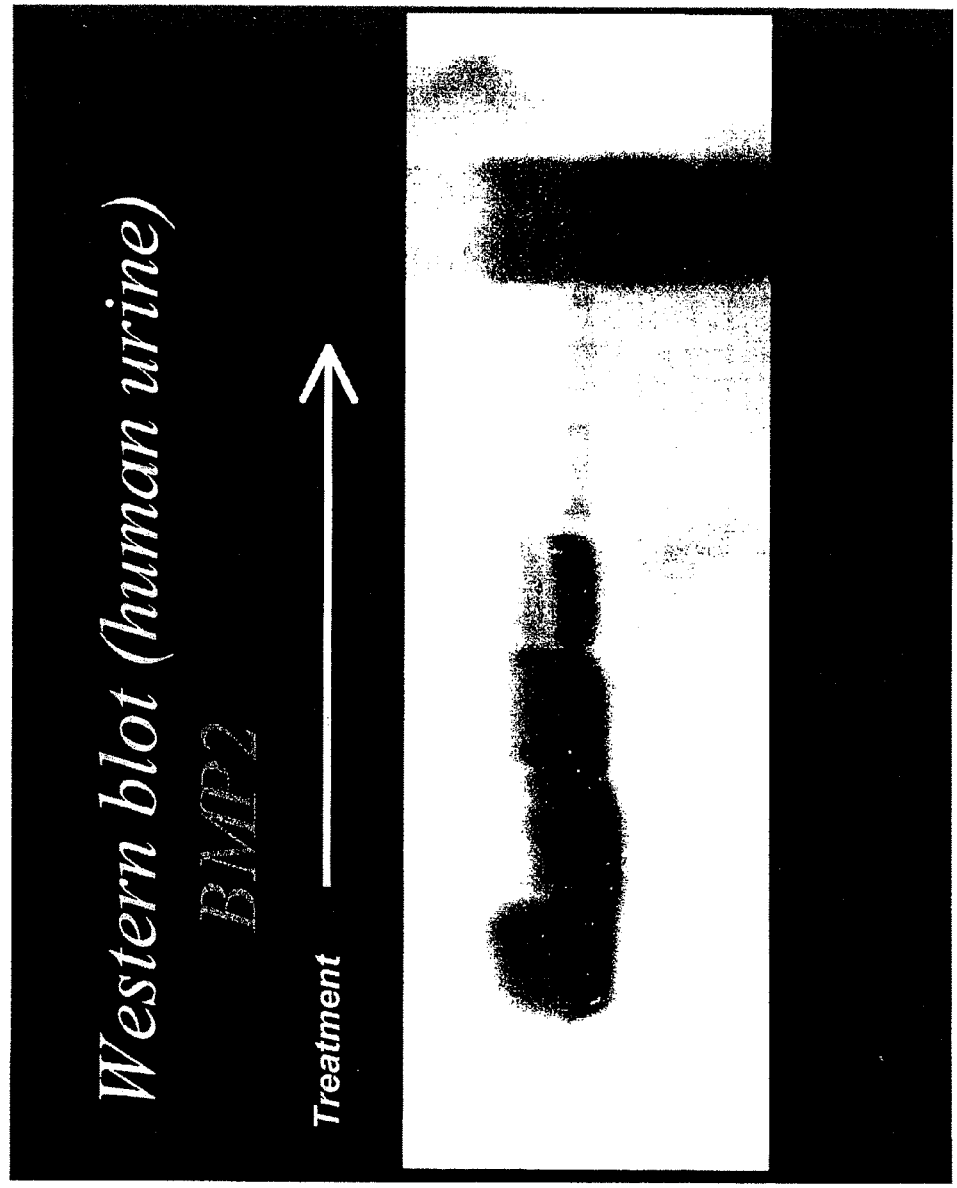
FIG. 6 shows the results of determination by Western blotting of urinary BMP2 levels in diabetic nephropathy patients.

Urinary BMP2 levels in a diabetic nephropathy patient were determined by Western blotting. The results revealed that urinary BMP2 was reduced as the disease was improved by treatment (FIG. 6).

Figure 7:
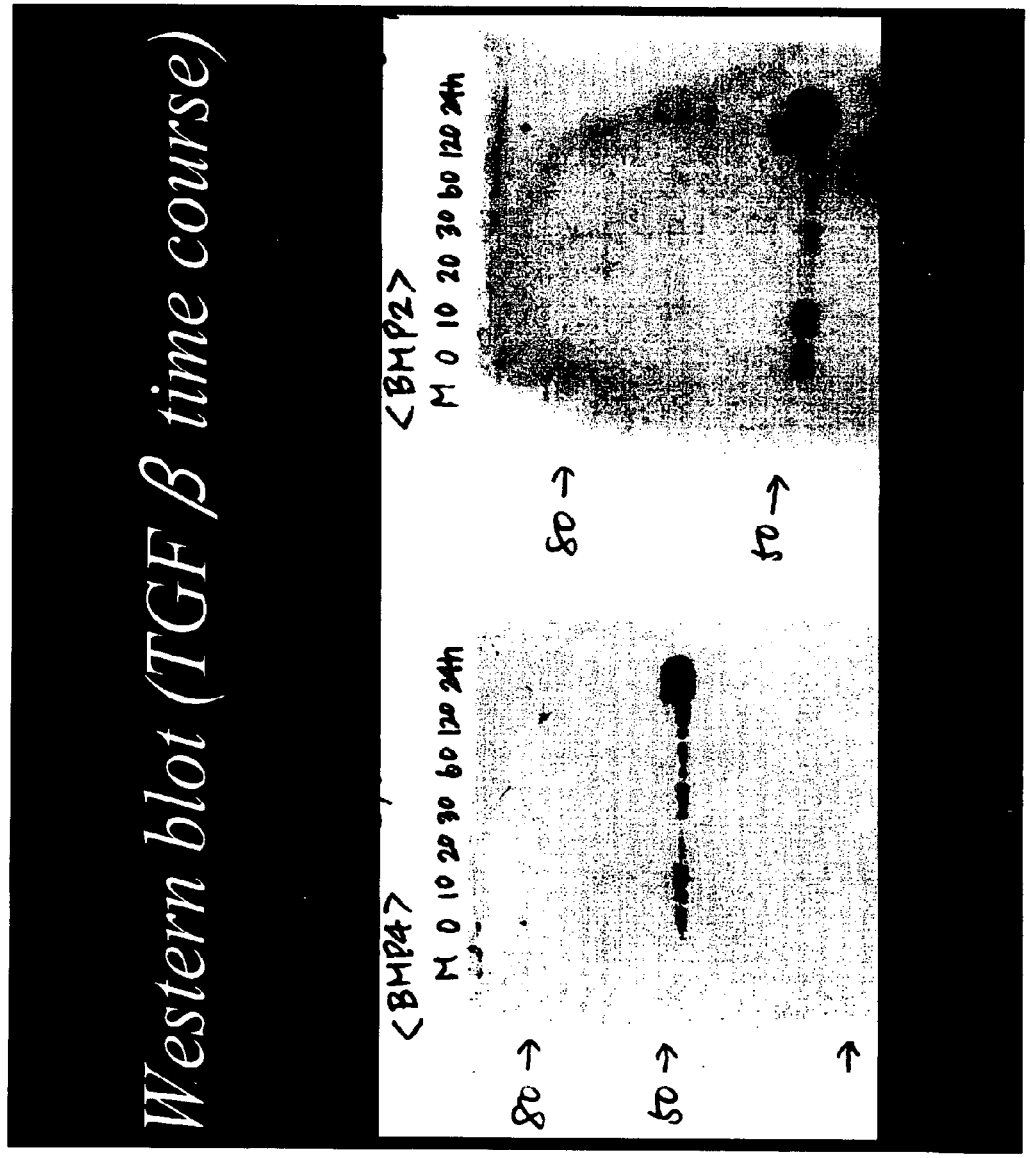
FIG. 7 shows the results of determination by Western blotting of the expression of BMP2 and BMP4 in the presence of chronic stimulation with TGF-β signal.

Chronic stimulation with TGF-β signals promoted expression of BMP2 and BMP4 proteins remarkably (FIG. 7). This suggests that these BMP proteins perform central functions in the TGF-β signaling pathway.

Materials and Methods

Cell Culture

A glomerular mesangial cell strain was established from glomeruli isolated from normal, 4 week-old mice (C57BL/6JxSJL/J), and was identified according to the method previously described (S1). The mesangial cells were cultured in B medium (a 3:1 mixture of minimal essential medium/F12 modified with trace elements) supplemented with 1 mM glutamine, 100 units/ml penicillin, 100 mg/ml streptomycin and 20% fetal calf serum. The cultured cells fulfilled the criteria generally accepted for glomerular mesangial cells (S2). AGEs or BSA exposure was carried out as described previously (S3). cDNA library construction and Yeast One-Hybrid screening The inventors prepared cDNA from mouse mesangial cells exposed to AGEs and inserted it into pGAD vector. Yeast one-hybrid screening was carried out using MATCHMAKER one-hybrid kit (Clontech, Palo Alto, Calif.). Briefly, tandem repeats of the 27 bp sequence (TTC-CTCCCCTTGGAGGAGCGCCGCCCG: CIV-1) (SEQ ID NO: 14) from the mouse Col4 gene were ligated into a yeast integration and reporter vector pHISi (MATCHMAKER One-hybrid: Clontech, Palo Alto, Calif.) or pLacZi (MATCH-MAKER One-hybrid: Clontech, Palo Alto, Calif.) to generate CIV-1-pHISi or CIV-1-pLacZi vector, respectively (S4). Each of these reporter constructs was linearized and integrated into the chromosome of yeast YM4271 (MATCH-MAKER One-hybrid: Clontech, Palo Alto, Calif.). The resulting yeast cells with the integrated CIV-1-pHISi and CIV-1-pLacZi were used for one-hybrid screening with the AGEs stimulated-mouse mesangial cell-derived cDNA library. Positive colonies were selected on SD/-His/-Leu plates with 45 mM 3-amino-1, 2, 4-triazole (3-AT). To exclude false positive clones, the inventors performed β-galactosidase filter lift assay (Clontech). Plasmids were rescued from the remaining yeast colonies and retransformed into *E coli* DH5α.

ChIP Assay

ChIP assays were essentially performed as described previously by Luo et al (S5). The inventors used anti-Smad1 antibody, anti-Smad4 antibody (Santa Cruz Biotechnology, Santa Cruz, Calif.) or normal control IgG at 4° C. overnight. PCR was performed to amplify the region containing the CIV-1 motif. The 5' primer was 5'-GGAGCTC-CCCAATTTGTTG-3' (SEQ ID NO: 15), and the 3' primer was 5'-CAGCCTCCGCCTCTTACC-3' (SEQ ID NO: 16). The resulting PCR product was around 100 bp on agarose gel electrophoresis.

Reporter Assay $1.3 \times 10^5$ COS7 cells in 10% fetal bovine serum-added Dulbecco's modified Eagle's Medium (DMEM) were seeded into six-well plates. Eight hours later, the cells were cotransfected with 750 ng of CIV-1-LacZ reporter construct along with either 750 ng of vector encoding wild type Smad1 or a mock vector. 75 ng of CMV-LUC (Firefly luciferase gene under the control of CMV promoter) was also introduced into the cells as an internal control. Transfection was performed with FuGENE6 transfection reagent (Roche Molecular Biochemicals, Indianapolis, Indiana). Forty-eight hours later, the cells ware harvested in reporter lysis buffer. Then, β-galactosidase and luciferase activities were measured using β-galactosidase Reporter System (BD Biosciences, San Jose, Calif.) and Luciferase Reporter Assay System (Promega, Madison, Wis.). β-galactosidase results were corrected with luciferase activities measured.

RNase Protection Assay

RNase protection assay was performed as described previously (S6). The nucleotide sequence of the probe used in this assay corresponds to positions 1172-1433 of Acc No. U58992, as described below:

```
                                         (SEQ ID NO: 17)
cccaccacc gtctgcaaga tccccagcgg gtgcagcttg aaaatcttca acaaccaaga gtttgctcag ctactggcgc agtctgtgaa ccacgggttc gagaccgtgt atgaactcac caaaatgtgc actattcgga tgagcttcgt gaagggttgg ggagccgaat accaccggca ggatgttacc agcacccct gctggattga gatccatctg catggccctc tccagtggct ggataaggtt ctgacccaga tgg
```

Western Blotting

Mesangial cells were cultured in the presence of AGEs or BSA (as control) for 72 hours. Cells were harvested in sample buffer, resolved by SDS-polyacrylamide gel electrophoresis and transferred to nitro-cellulose membrane and subjected to Western blot using a 1:500 dilution of anti-Smad1 antibody and anti-pSmad1 antibody (Santa Cruz Biotechnology), followed by detection using an enhanced chemiluminescence detection system (Invitrogen, Carlsbad, Calif.).

Immunostaining of Cultured Cells and Cytosections

Cultured cells were fixed in 4% paraformaldehyde. The following antibodies were used: anti-Smad1 antibody, 1:100 (Santa Cruz Biotechnology); anti-pSmad1 antibody, 1:100 (Calbiochem). An appropriate fluoresceine isothiocyanate-conjugated secondary antibody was used for visualization and imaging was done using a laser microscope and a fluorescent microscope (Olympus, Tokyo, Japan).

Smad1 Morpholino Antisense Oligonucleotide

The antisense oligonucleotide used was a 25-nucleotide morpholino oligo (Genetools LLC, Philomath, Oreg.). The sequence is 5'-CAAGCTGGTCACATTCATAGCGGCT-3' (SEQ ID NO: 13). As a control, an oligo with the base composition 5'-CAtGCTcGTCACATTCAaAGCcGCT-3' (SEQ ID NO: 18) was used. In vitro RNA transcription was performed as previously described (S7).

Histology

Histopathological studies were performed on human tissues. This experiment was in accordance with the Declaration of Helsinki, and the inventors obtained approval from the institutional review board. All patients gave their informed written consent. Diabetic nephropathy renal specimens (n=5) were obtained from renal biopsies. Control human tissue sections were obtained from normal renal cortex harvested from kidneys removed for renal malignancy. Tissues for analysis were sampled from the pole opposite the tumor. Cryopreserved kidney tissues were cut into 5 μm thick sections and fixed in acetone for 5 min. Endogenous peroxidase activity was quenched by a 20 min-incubation in the dark with 1% $H_2O_2$ in methanol. To eliminate nonspecific staining, sections were incubated with the appropriate preimmune serum for 20 min at room temperature, followed by immunostaining with primary antibodies: anti-Smad1 (Santa Cruz Biotechnology) and anti-ALK1 (R&D, McKinley Place, Nebr.) antibodies.

Analysis of Expression Levels with Microarrays

Individual mRNA expression levels in mesangial cells cultured in the presence of AGEs and mesangial cells cultured in the presence of BSA were measured using Agilent Technologies Mouse cDNA Microarray Kit.

EXAMPLE 2

Glomerulosclerosis is characterized by quantitative increase in extracellular matrix (ECM). Type IV collagen (Col4) is one of the major components of expanded ECM in glomerular diseases. However, the molecular mechanism of transcriptional regulation of Col4 gene was not clear until the recent report of the present inventors. The inventors showed that Smad1 transcriptionally regulates the overexpression of Col4 in diabetic nephropathy (A8). Smad1 directly transduces signals to downstream target genes, such as osteopontin (A9), inhibition of differentiation (A10), and type I collagen (A11), and is essentially important for the development and progress of kidney diseases (A12). These findings suggest that Smad1 is a transcriptional factor critical for the development and progress of glomerulosclerosis.

Signal transducer and activation (STAT) proteins were shown to be involved in signal transduction of numerous cytokines and growth factors. STAT3 activation is a key regulator for PDGF-induced mitogenesis (A13). Nakashima et α1 reported that transcriptional coactivator p300 physically interacts with STAT3 and Smad1, which were followed by the subsequent activation of the target gene transcription in astrocyte differentiation (A14). The inventors postulated from these findings that PDGF activates the STAT3-Smad1 signaling pathway in mesangial cell proliferation and that this process is essential for mesangial cells to progress into glomerulosclerosis.

In this study, the inventors demonstrated the effect of administration of anti-PDGF β-receptor antibody that inhibits activation by PDGF-B chain in rat glomerulonephritis, and examined the signaling pathway for regulating both glomerular cell proliferation and glomerulosclerosis in vivo and in vitro.

Materials and Methods
Animals

Male Wistar rats (CLEA Japan, Inc. Japan) weighing 180 to 200 g were used for this study. Rats were raised under specific pathogen-free conditions. All of the animal experiments were performed in accordance with institutional guidelines, and the Review Board of Tokushima University granted ethical permission to this study.

Induction of Thy1 Glomerulonephritis

Experimental mesangial proliferative glomerulonephritis (Thy1 GN) was induced by a single intravenous injection of anti-rat Thy-1.1 monoclonal antibody (1 mg/kg) (Cedarlane Laboratories, Ontario, Canada) as described elsewhere (A15). These rats were sacrificed at days 1, 2, 4, 6, and 12 (n=6 per group) after the administration of anti-Thy-1.1 antibody. Six age-matched rats were injected with vehicle alone and sacrificed as controls.

Protocol of Treatment with Anti-PDGF β-R antibody in Thy1 GN

A rat monoclonal anti-PDGF β-receptor antibody (APB5) and its antagonistic effects on the PDGF β-R signal transduction pathway in vivo and in vitro were described previously (A16, A17). The rats were injected intraperitoneally everyday with 400 µg of APB5 (kindly provided by Prof. Shinichi Nishikawa of RIKEN) or irrelevant isotype-matched control rat IgG (kindly provided by Prof. Shinichi Nishikawa of RIKEN) after the administration of anti-Thy1.1 antibody from day 0, and were sacrificed at days 1, 2, 4, 6, and 12 (n=6 per group).

Histological Examination
Light Microscopy

After removal of the kidney, tissue blocks for light microscopy study were fixed in methyl Carnoy's solution (methanol: glacial acetic acid=3:1), and embedded in paraffin. Sections (2 µm) were stained with hematoxylin and eosin (HE), periodic acid-Schiff's reagent (PAS) and periodic acid-methenamine silver (PAM).

Immunohistochemistry Kidney sections were processed for immunohistochemistry according to standard procedures. For studying proliferating cell nuclear antigen (PCNA), Col4 and Smad1, methyl Carnoy's solution-fixed and paraffin-embedded tissue blocks were used. Kidney sections were rehydrated and treated with 0.3% hydrogen peroxide in methanol for 30 minutes to deactivate endogenous peroxidase. To eliminate nonspecific staining, sections were incubated with the appropriate preimmune serum for 20 minutes at room temperature, and then incubated with Avidin D blocking solution and Biotin blocking solution (Vector, Burlingham, Calif., USA) for 15 minutes each. Sections were incubated with anti-PCNA antibody (1:200 dilution), anti-Col4 antibody (1:200 dilution), and anti-Smad1 antibody (1:100 dilution) (Santa Cruz Biotechnology, CA, USA) for 60 minutes at room temperature, and then incubated with appropriate biotinylated secondary antibodies followed by incubation with avidin-biotin peroxidase complex (Vectastain ABC System, Vector). Peroxidase conjugates were subsequently localized using diaminobenzidine tetrahydrochloride (DAB). For studying phosphorylated Smad1 (pSmad1) and phosphorylated (pSTAT3), tissues were snap-frozen in cold acetate in OCT compound (Miles Inc., Ind., USA), and were cut into 4 µm-thick sections and fixed in acetone for 5 minutes, and treated with 0.3% hydrogen peroxide in methanol for 30 minutes to deactivate endogenous peroxidase. Sections were treated in the same manner as sections for PCNA examination were treated, with the following primary antibodies: anti-pSmad1 antibody (1:100 dilution) (Calbiochem, CA, USA) and anti-pSTAT3 antibody (1:100 dilution) (Santa Cruz Biotechnology). To evaluate the nuclear number, sections were counterstained with hematoxylin solution.

Quantitation of Light Microscopy

Glomerular morphometry was performed on PAM-stained tissues. The glomerular surface area and the PAM-positive area to glomerular area (%) were measured using an image analyzer with a microscope (IPAP; Image Processor for Analytical Pathology; Sumitomo Chemical Co., Osaka, Japan) as described (A18-A20). For each animal, 50 glomeruli were analyzed.

Quantitation of Immunohistochemistry

PCNA: For quantitation of proliferating cells (PCNA positive cells), a blinded observer evaluated 50 glomeruli per specimen and mean values per glomerulus were calculated. pSmad1: To quantitate the expression of pSmad1, pSmad1 positive cells per glomerular cell were counted, and mean percentages of pSmad1 positive cells were calculated. Col4, Smad1 and pSTAT3: The area stained brown on an immunoperoxidase-stained section was selected for its color range, and the percentage of this area to total glomerular mesangial area was quantitated by using IPAP. In each animal, 50 glomeruli were evaluated.

Cell Culture Experiment

A glomerular mesangial cell strain was established from glomeruli isolated from normal, 4 week-old mice (C57BL/6JxSJL/J) according to the method previously described (A21). The mesangial cells were cultured in B medium (a 3:1 mixture of minimal essential medium/F12 modified with trace elements) supplemented with 1 mM glutamine, 100 units/ml penicillin, 100 mg/ml streptomycin, and 20% fetal calf serum (FCS). The cultured cells fulfilled the criteria generally accepted for glomerular mesangial cells (A22). The cultured mesangial cells in B medium/20% FCS were plated onto 100 mm dishes. After 24 hours of incubation, the cells were starved for two days in B medium/0.1% BSA, and cultured in B medium/2% FCS with 5 ng/ml PDGF-B (Calbiochem), then incubated with 100 ng/ml of APB5 or rat IgG (control) for 24 hours.

Cell Proliferation Test by BrdU ELISA

The proliferation of mesangial cells was also determined using a colorimetric immunoassay for the quantification of cell proliferation, based on the measurement of BrdU incorporation during DNA synthesis (Amersham Pharmacia Biotech Inc., NJ, USA). The BrdU ELISA was performed according to the manufacturer's instructions. Briefly, mesangial cells were plated at low density in 96-well flat-bottomed microtiter plates containing B medium/10% FCS and allowed to adhere overnight. The subconfluent cells were then starved for two days in B medium/0.1% BSA. 100 ng/ml of APB5 was then added to cells in B medium/2% FCS with 5 ng/ml of PDGF-B and 10 mM BrdU. After six hours of culture, plates were centrifuged and cells denatured with fixative solution then incubated for 30 min with 1:100 diluted anti-BrdU mAbs labeled with peroxidase. After removing the labeled antibody, substrate solution was added for 15 min and the reaction stopped by adding 1 M sulfuric acid. The absorbance was measured within 5 min at 450 nm with a reference wavelength at 690 nm using an ELISA plate reader (Model 550, Bio-Rad Laboratories, CA, USA). The blank corresponded to 100 p of culture medium without BrdU.

Western Blot Analysis

Cultured mesangial cells were starved for 24 hours in B medium/0.1% BSA. The cells were stimulated by 5 ng/ml of PDGF-BB with 100 ng/ml of APB5 or control IgG for 120 min. Cells were suspended in lysis buffer, resolved by SDS-polyacrylamide gel electrophoresis and transferred to nitrocellulose membrane and subjected to Western blot using a 1:1000 dilution of anti-pSTAT3 antibody, 1:1000 dilution of anti-pSmad1 antibody and 1:2000 dilution of anti-Col4 antibody, followed by detection using an enhanced chemiluminescence detection system (Amersham Pharmacia).

Cell Transfection

Plasmid construct expression vectors of wild type STAT3 and dominant negative STAT3 were kindly provided by Jackie Bromberg (The Rockefeller Univ.) (A23). Mesangial cells (60 mm dish) were transfected with an expression vector encoding wild type STAT3 (8 mg) or dominant negative STAT3 (8 mg) by using Lipofectamine2000 (Invitrogen Life Technologies) according to the manufacturer's instructions. After 6 hr of transfection, medium was changed to growth medium (60% DMEM, 20% F12, 20% fetal calf serum). After 48 hr, cells were suspended in lysis buffer, and Western blot analysis was performed as previously described.

Statistical Analysis

All values were expressed as the mean±SE and analyzed by Mann-Whitney nonparametric analysis, or one-way analysis of variance with a modified t-test. P values<0.05 were considered significant.

Statistical analyses of cell proliferation test and expression of Smad1 mRNA in cultured mesangial cells were performed by t-test. Quantitation of immunohistochemistry and expression of Smad1 mRNA in glomeruli were analyzed by one-way ANOVA followed by the post hoc test. P values <0.05 were considered significant. Data are expressed as means±SD.

Experimental Results

Morphological Changes in Thy1 GN

Figure 9:
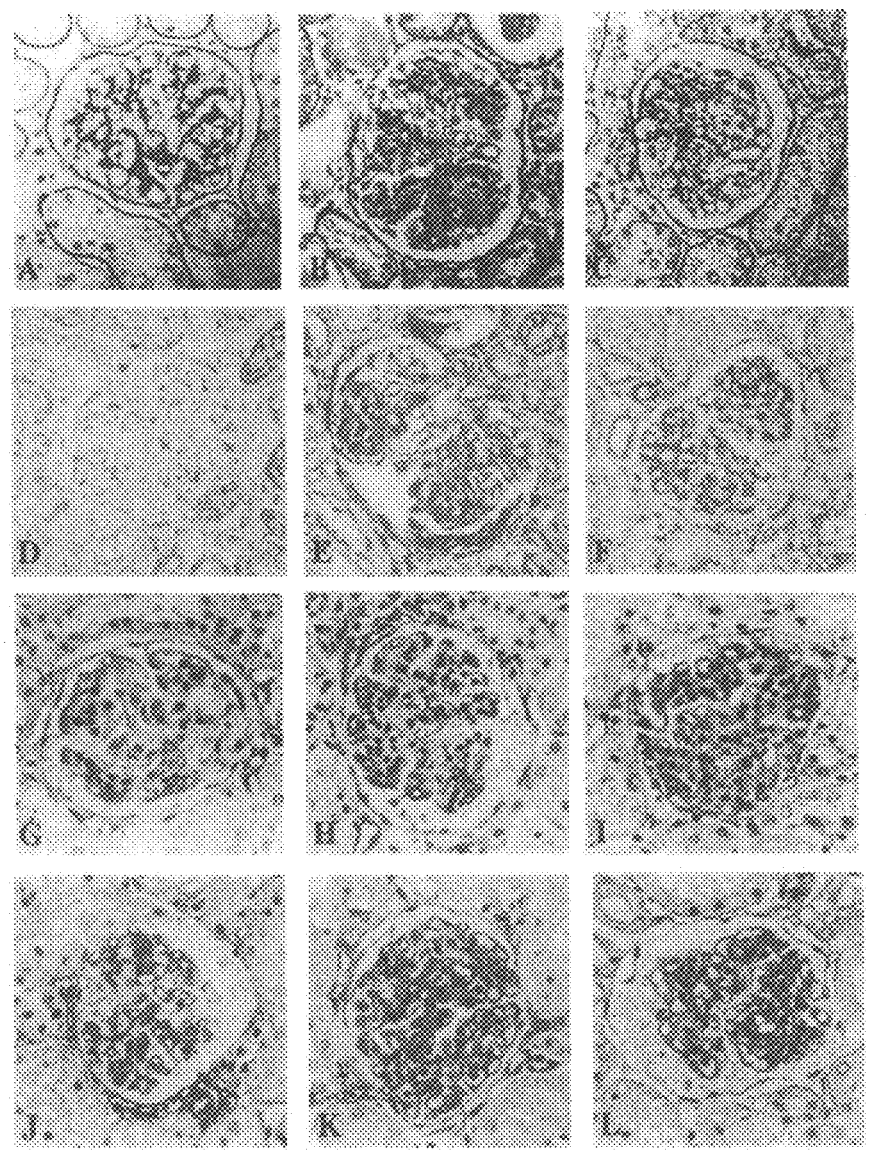
FIG. 9 is microscopic images showing diffuse increase of the mesangial matrix and expansion of the mesangial area in Thy1 GN rats. Overexpression of Col4 was observed in the expanded mesangial area by immunohistochemical staining with anti-Col4 antibody. APB5 reduced both mesangial proliferation and Col4 expression. Thy1 GN glomeruli were significantly positive in PDGF-B chain and PDGF β receptor. APB5 also reduced these overexpressions. A-C: PAM; D-F: Col4; G-H: PDGF-B chain; J-K: PDGF β receptor; A, D, G and J: normal control rats; B, E, H and J: disease control rats at day 6; C, F, I and L: APB5-treated rats at day 6.

In Thy1 GN, proliferation of mesangial cell begins at day 2, peaked at day 6, and subsides at day 12 after the injection. FIG. 9 shows a representative light microscopic picture at day 6 in each group. Thy1 GN group showed increase of the mesangium, which was peaked at day 6 (FIG. 9B). Proliferation of glomerular cells was assessed by Immunostaining of PCNA. PCNA positive cells were markedly increased in Thy1 GN group, and peaked at day 6 (FIG. 9E).

Col4 is one of the main components of ECM in glomerulosclerosis. Col4 was weakly visible along the glomerular basement membrane and almost negative in the glomeruli in the normal control group (FIG. 9G). On the other hand, Thy1 GN group showed strong Col4 positive in the expanded mesangial area (FIG. 9H).

Figure 10:
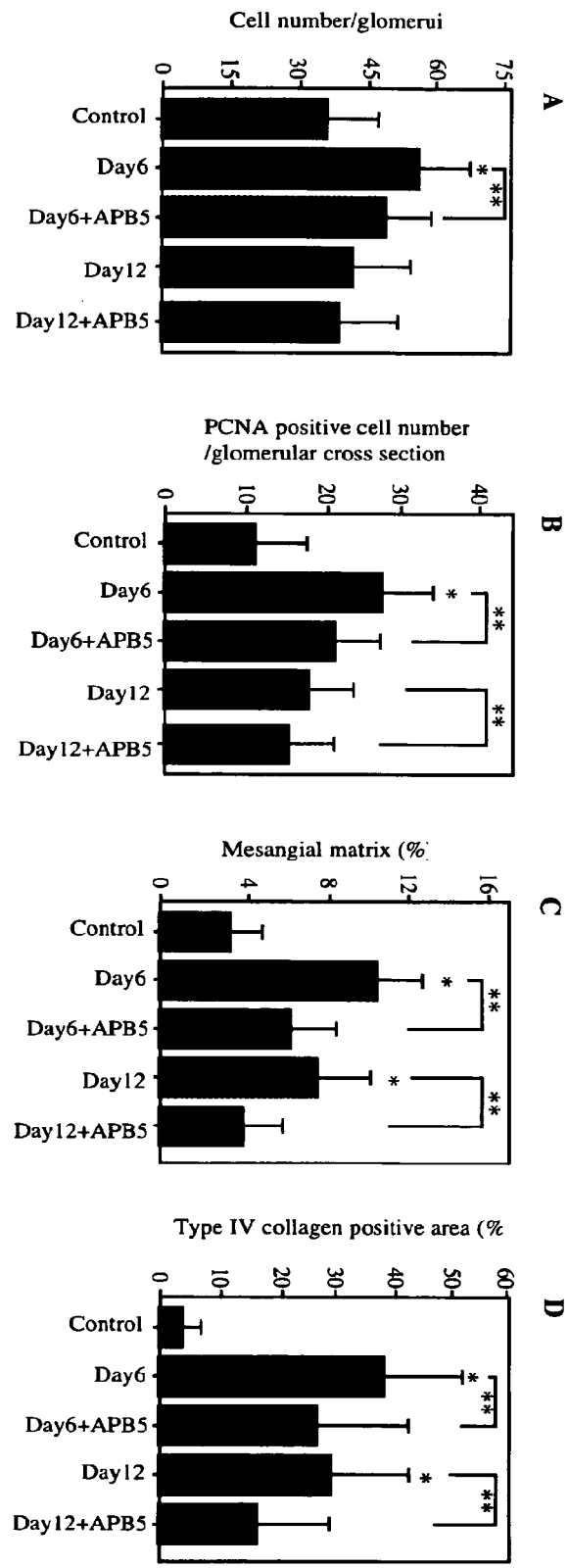
FIG. 10. Quantitation of histological changes and effects of APB5 administration in Thy1 GN. A: Glomerular cell number. Increase in glomerular cell number is observed in Thy1 GN groups. B: PCNA positive cell number in Thy1 GN. PCNA-positive cell number in the glomeruli of APB5-treated rats was significantly reduced at each point examined. C: Mesangial matrix expansion. Mesangial matrix increase was observed at Day 6 in Thy1 GN rats. APB5 significantly reduced mesangial matrix increase at each point examined. D: Expression of type IV collagen. In the control group, Col4 was strongly positive in the expanded mesangial area. APB5 significantly reduced Col4 expression. *P<0.001 vs. control group; **P<0.001 vs. APB5 non-treated disease control group.

In Thy1 GN, both PDGF-B and PDGF β-receptor were significantly positive in the glomeruli (FIG. 10). These findings indicate that excessive proliferation of mesangial cells, glomerular hypertrophy and glomerulosclerosis lesions occur coincidently in glomerulonephritis induced by anti-Thy1 antibody.

Figure 11:
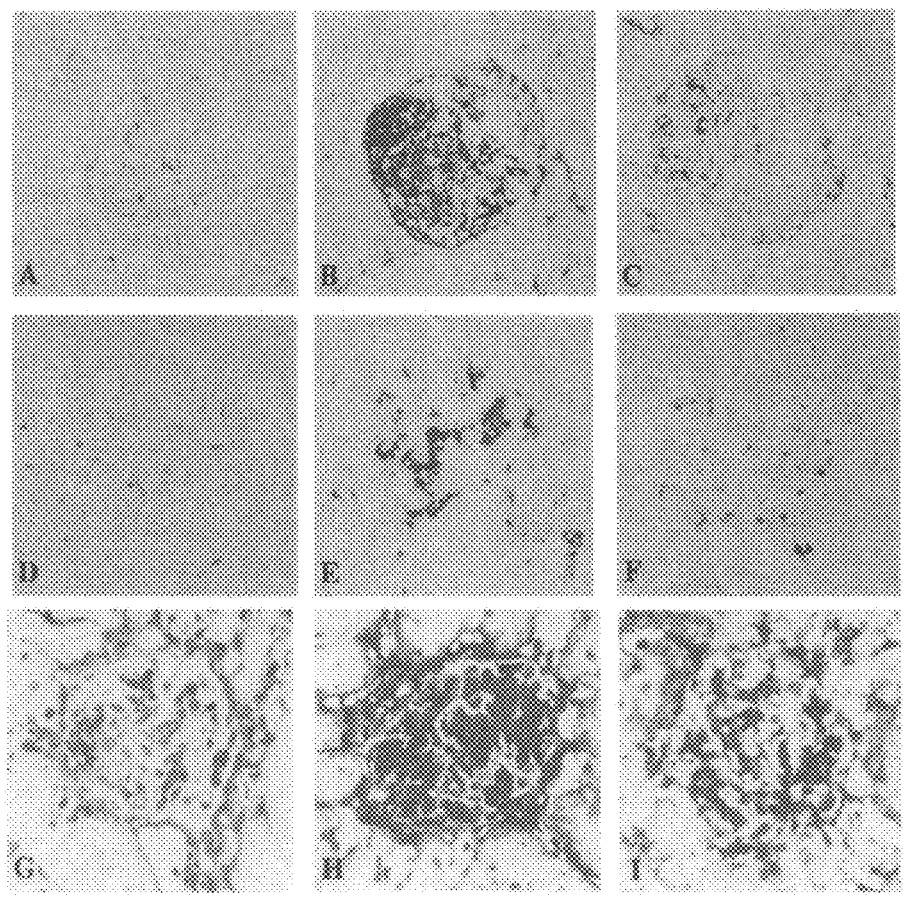
FIG. 11. Immunohistochemical staining of Smad1, phosphorylated Smad1 and phosphorylated STAT3 in Thy1 GN. Smad1, phosphorylated Smad1 and phosphorylated STAT3 expressions showed a surprising increase in immunohistochemical staining of the glomeruli of Thy1 GN rats. Phosphorylated Smad1 was observed remarkably at the same site as nuclei were observed in Thy1 GN rats. APB5 treatment brought significant reduction in each of these substances. A-C: Smad1; D-F: phosphorylated Smad1; G-I: phosphorylated STAT3; A, D and G: normal control rats; B, E and H: untreated Thy1 rats at day 6; C, F and I: APB5-treated rats at day 6.

Anti-PDGF β-Receptor Antibody Inhibits Both Glomerular Cell Proliferation and Glomerulosciterosis in Vivo APB5 inhibits PDGF β-R-mediated signaling pathways as described previously. Treatment with APB5 showed significant reduction in both glomerular cell number and glomerular PCNA positive cells in Thy1 GN at each point examined (FIG. 9C, 9F, 11A, 11B). Overexpression of PDGF-B chain and PDGF P-R were significantly reduced after administration of APB5 (FIG. 10C, 10F). APB5 treatment also reduced mesangial matrix increase in Thy1 GN, which was assessed with the ratio of PAM-positive area to glomerular area (FIG. 11C). Col4 expression in mesangial cells in Thy1 GN was reduced by APB5 treatment (FIG. 11D). These data indicate that APB5 treatment can reduce both the mesangial cell proliferation and the mesangial matrix expansion in Thy1 GN.

Figure 12:
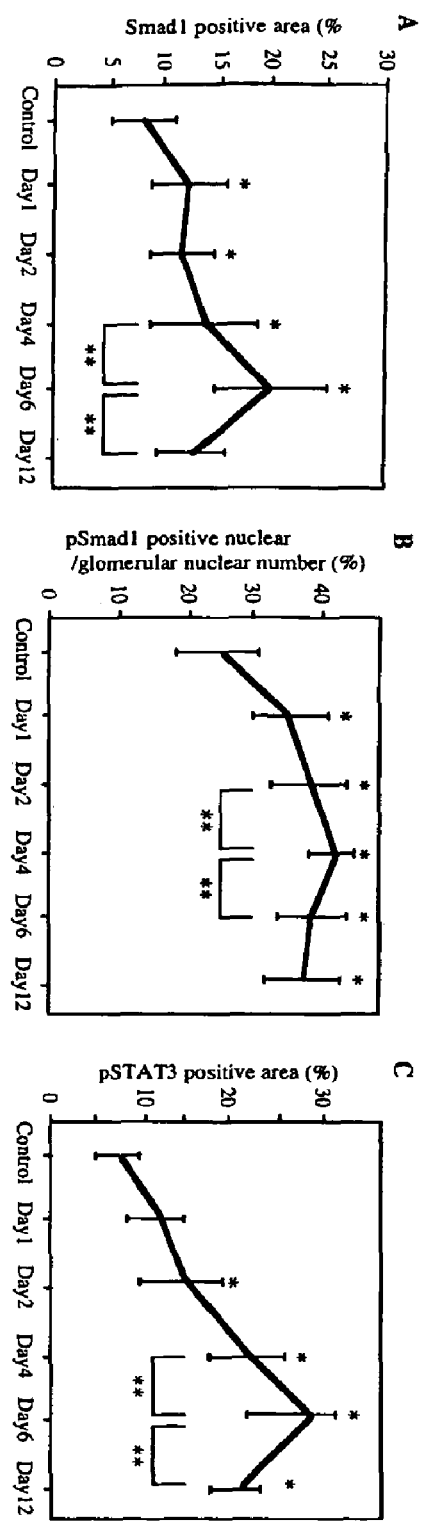
FIG. 12. Time course of Smad1, pSmad1 and pSTAT3 expressions. Day 0, day 1, day 2, day 4, day 6 and day 12 renal sections from Thy1 GN rats were immunohistologically stained with anti-Smad1, anti-pSmad1 and anti-pSTAT3 antibodies. A: Smad1 expression in Thy1 GN. Smad1 expression peaked at Day 6 and was calmed down at day 12. B: Time course of the ratio of pSmad1 positive cells to the total glomerular cell number. pSmad1 expression peaked at Day 4. C: Time course of pSTAT3 expression. The ratio of pSTAT3 positive portion to the mesangial area increased up to Day 6, and was calmed down at day 12. *P<0.001 vs. control group; **P<0.001 vs. each examination point.

Time Course of Expression of Smad1, Phosphor-Smad1 (pSmad1) and Phophor-STAT3 (pSTAT3) in Thy1 GN The inventors examined the expression of Smad1 in the Thy1 GN rat kidney by immunostaining. Although Smad1 was hardly detected in healthy control glomeruli (FIG. 12A), a typically expanded mesangial pattern was observed in the glomeruli of Thy1 GN group at day 6 with high expression of Smad1 there (FIG. 12B). IPAP image analysis system was used to quantitate the expression of Smad1. The peak of glomerular Smad1 expression occurred at day 6 (FIG. 13A), which was consistent with the peak of mesangial cell proliferation. As shown in FIG. 12C, glomerular Smad1 expression declined rapidly after day 6.

Figure 13:
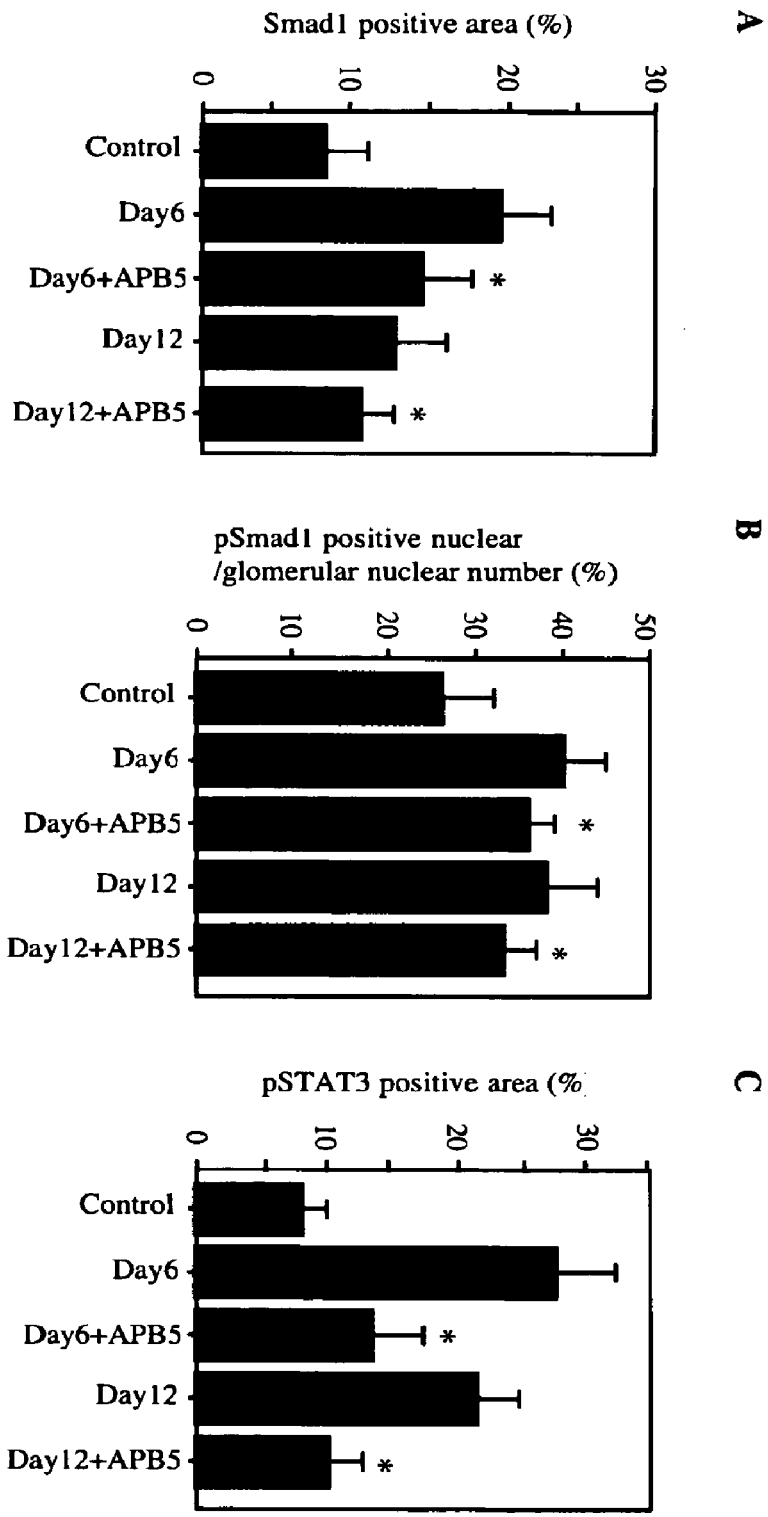
FIG. 13. Effects of APB5 treatment on Smad1, pSmad1 and pSTAT3 expressions. The results of immunohistological staining and quantitation of Smad1, pSmad1 and pSTAT3 expressions revealed that these proteins were reduced by APB5 treatment as Col4 expression in mesangial matrix and glomeruli was reduced. A: Smad1 expression. B: pSmad1 expression. C: pSTAT3 expression. *P<0.01 vs. APB5 non-treated disease control.
Figure 14:
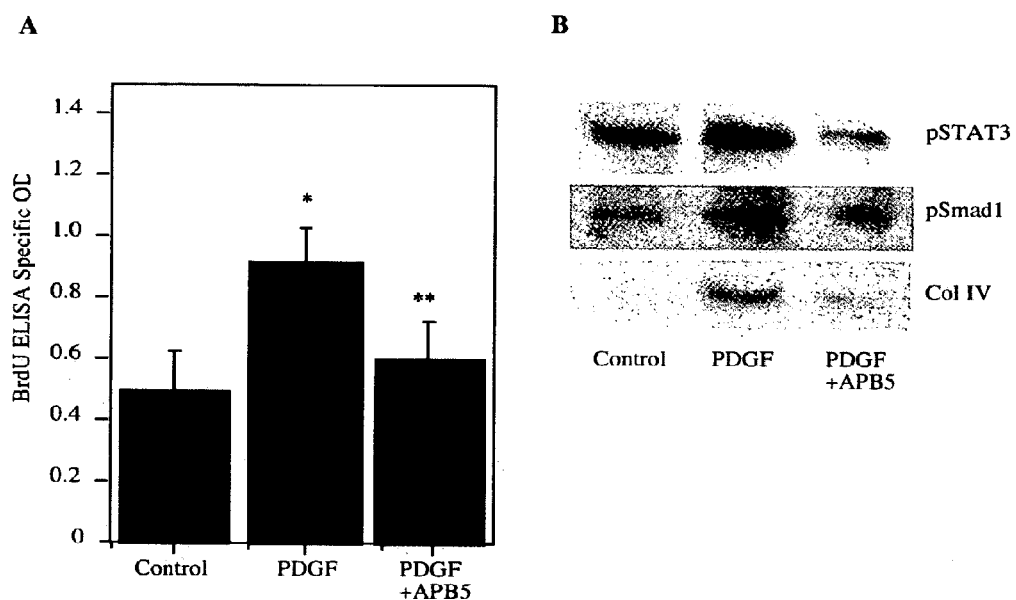
FIG. 14. Effects of APB5 in vivo. A: Inhibitory effect of APB5 on mesangial cell proliferation. Addition of PDGF-B increased the proliferation of mesangial cell, and APB5 significantly inhibited this proliferation. *P<0.05 vs. control; **P<0.05 vs. PDGF-B stimulated control. B: Western blot analysis revealed that pSTAT3, pSmad1 and Col4 protein expressions were reduced by addition of APB5. The results of one experiment out of three independent experiments are shown.

Subsequently, the inventors examined whether or not the transcription and phosphorylation of Smad1 are occurring in Thy1 GN. As a result of immunohistochemistry, pSmad1 was hardly observed in healthy control group (FIG. 14A). However, in Thy1 GN group, pSmad1 was strongly positive in the nuclei (FIG. 14B). To quantitate the expression of pSmad1, pSmad1 positive cells per glomerulus were counted (FIG. 13B). Glomerular expression of pSmad1 was upregulated at day 1 of Thy1 GN and reached the peak at day 4, which was the early phase of mesangial cell proliferation.

Since PDGF-B and PDGF β-R were upregulated in Thy1 GN and APB5 inhibited the overexpressions thereof, the inventors performed immunostaining of phosphorylated STAT3 which is a transcription factor of PDGF signaling pathway (A24). The expression of pSTAT3 was extensively increased in Thy1 GN (FIG. 15A, 15B, 15C), and peaked at day 6 (FIG. 13C).

Figure 15:
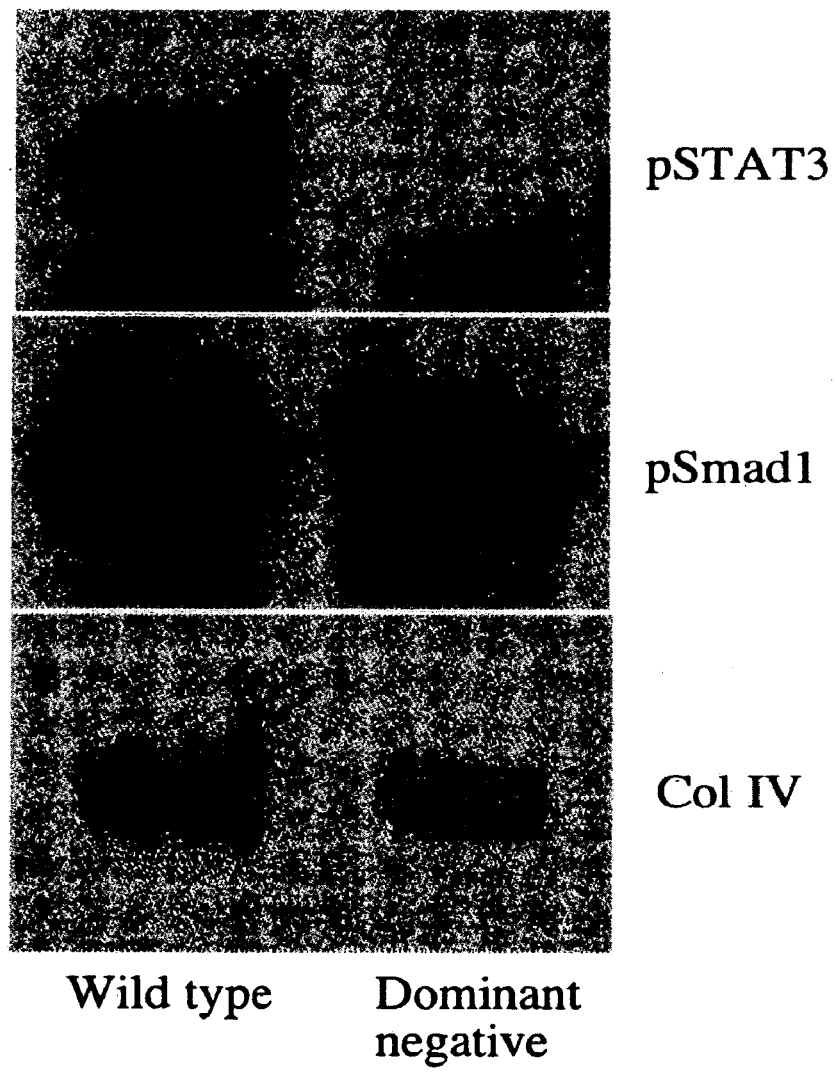
FIG. 15. Western blot analysis of gene-transfected mesangial cells. pSmad1 and Col4 protein expressions were reduced by dominant negative STAT3. The results of one experiment out of three independent experiments are shown.
Figure 16:
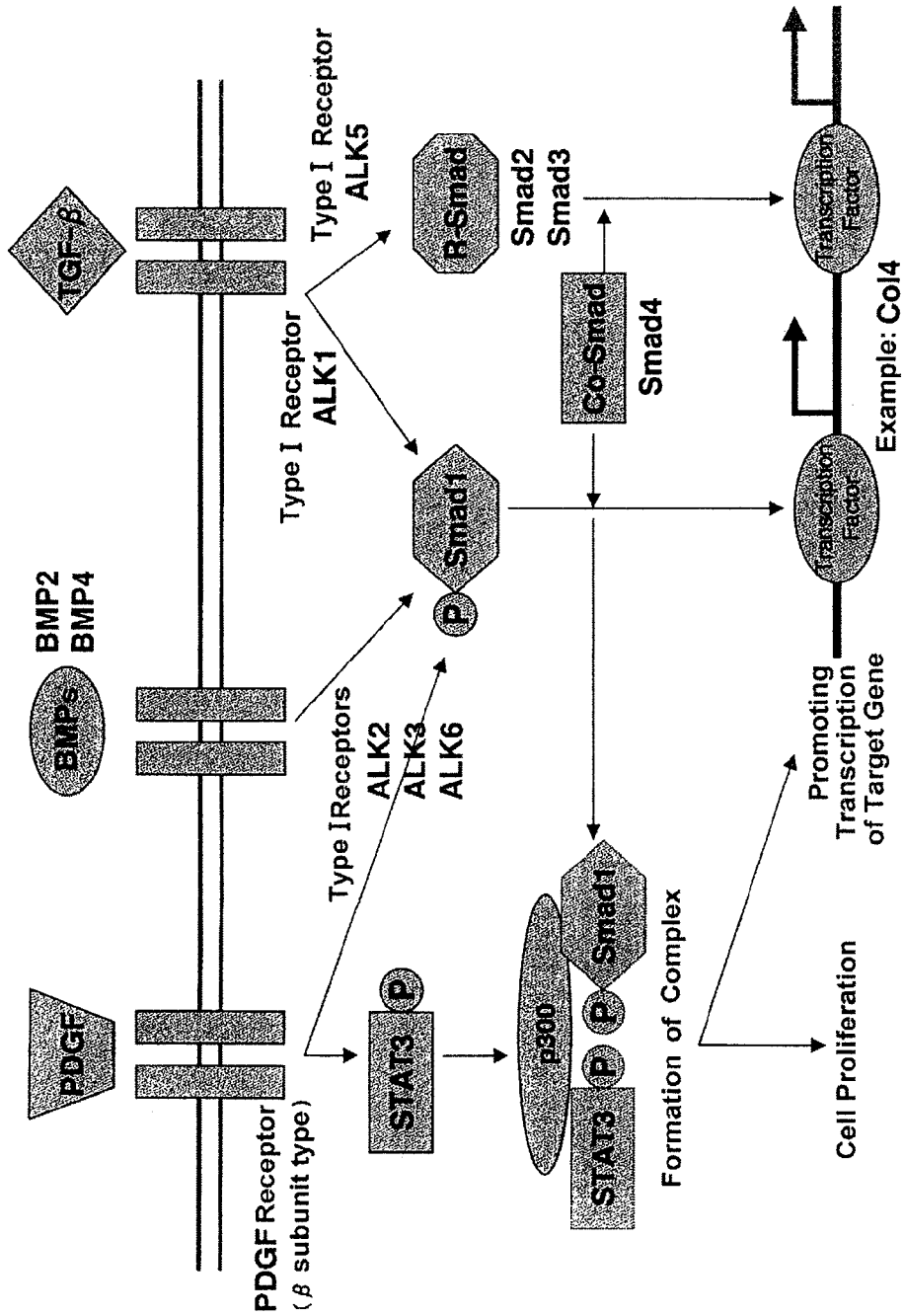
FIG. 16 is a schematic drawing of the signal transduction pathway based on the results of Examples 1 and 2.

APB5-treated groups had a significantly reduced expression of Smad1 and pSmad1 proteins in the glomeruli in Thy1 GN (FIG. 12D, 12E, 14D, 14E, 16A, 16B). Overexpression of pSTAT3 was also significantly reduced after administration of ABP5 at every point examined (FIG. 15D, 15E, 16C).

Effect of anti-PDGF β-R Antibody in Vitro

To determine whether or not APB5 inhibits the proliferation of mesangial cells, the inventors examined the proliferation of mesangial cells with or without APB5 by using BrdU ELISA system. As shown in FIG. 17A, addition of APB5 suppressed the PDGF-induced DNA synthesis in mesangial cells.

The inventors studied whether APB5 inhibits the expression of pSTAT3, pSmad1 and Col4 in mesangial cells stimulated by PDGF-B using Western blot analysis. APB5 reduced phosphorylation of STAT3 and Smad1 and the expression of Col4 (FIG. 17B).

Interaction Between STAT3 and Smad1

To elucidate the interaction between STAT3 and Smad1 that increases Col4 expression, a vector encoding dominant negative STAT3 was introduced into cultured mesangial cells.

Figure 18:
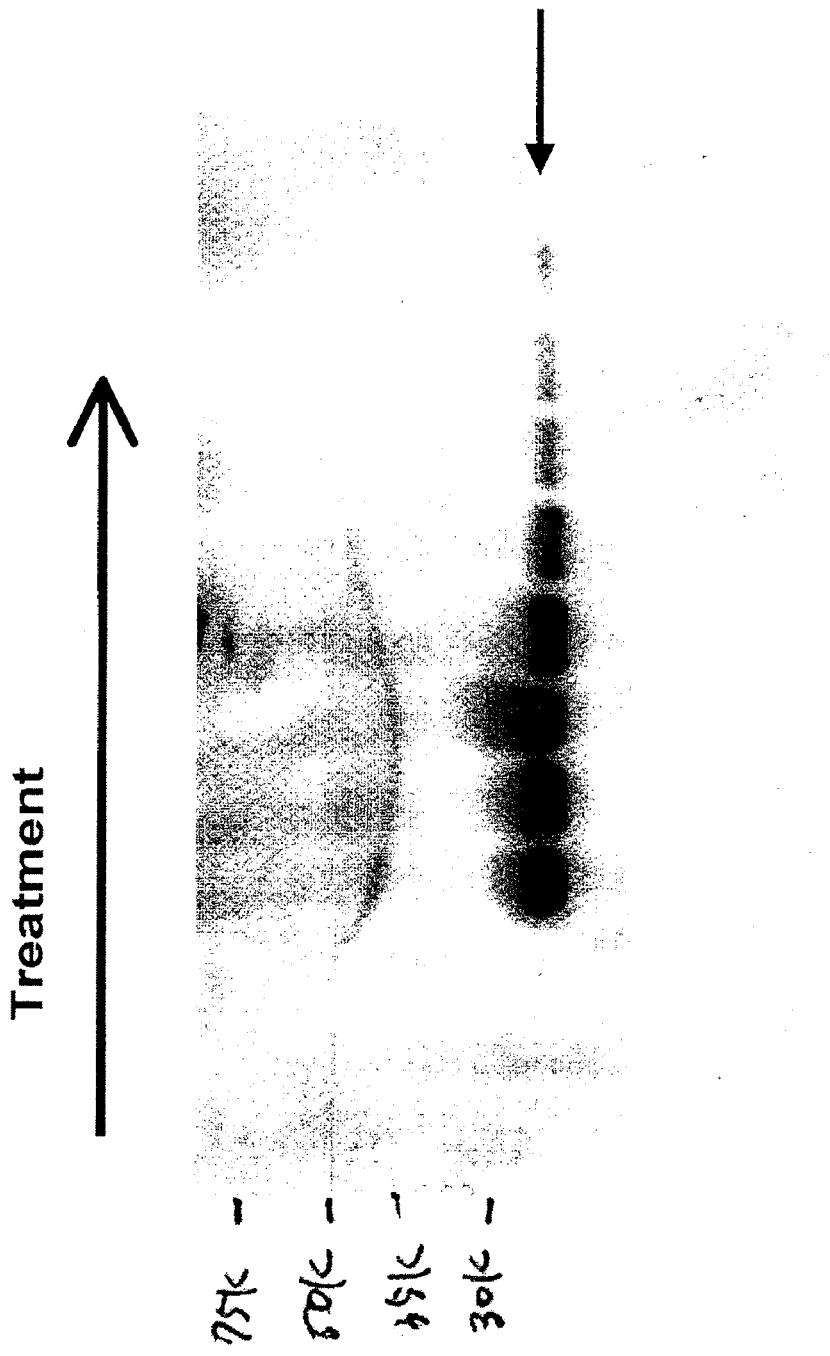
FIG. 18 shows the results of Western blotting on urine samples from a diabetic nephropathy patient under treatment, using anti-ALK-1 antibody as the primary antibody. Electropherograms taken at one week intervals are shown starting from the utmost left lane.

The introduction of dominant negative STAT3 definitely reduced the expression of pSmad1 and Col4 compared with the introduction of wild type STAT3 (FIG. 18).

Discussion

Many glomerular disorders are characterized by both mesangial cell proliferation and progressive glomerulosclerosis. However, mechanisms common for both of these important pathological findings have not been elucidated to date. This study demonstrated for the first time that activation of STAT3 and Smad1 is in a key pathway for regulating the interaction between the two critical events of progressive glomerular disorders. These results support a new direction of research about the pathogenesis and its therapeutical approach for chronic glomerulonephritis and diabetic nephropathy which are major problems in the 21st century in the world.

Glomerulosclerosis is a pathological feature seen in progressive glomerular disorders including chronic glomerulonephritis, IgA nephropathy and diabetic nephropathy. Glomerular cell proliferation occurs at an early stage in a number of glomerular diseases and subsequently glomerulosclerosis develops, which eventually progresses end stage glomerular disorders (A1, A2). Examples of this process are seen in IgA nephropathy, membranoproliferative glomerulonephritis, diabetic nephropathy, and light chain systemic diseases in human as well as in animal models such as Thy1 GN rat renal ablation model and so on (A25, A26). Inhibiting glomerular cell proliferation with anti-PDGF antibody (A7), anti-coagulant heparin (A27) or vitamin D analogue (A19) demonstrated to abolish the subsequent development of progressive glomerulosclerosis, but the mechanism has been unclear. In this study, the inventors have demonstrated the possible mechanism regulating the interaction between mesangial cell proliferation and glomerulosclerosis for these pathological processes.

A receptor for PDGF has been identified in murine and human mesangial cells (A28). PDGF is a potent, key mitogen for mesangial cells, and is constitutively synthesized as an autocrine cell growth factor in these cells in vitro (A28, A29). PDGF plays an important role for the progress of pathological conditions including glomerulonephritis, diabetic nephropathy and progressive glomerulosclerosis in vitro and in vivo (A3, A4). It has been previously reported that activation of PDGF receptor tyrosine kinase induces tyrosine phosphorylation of STAT3 proteins (A30, A31). The activation is associated with growth regulation and differentiation (A32, A33). The inventors have demonstrated that the overexpression of phosphorylated STAT3 has been identified associated with increased expressions of both PDGF and its β-receptor in vivo and in vitro, and that APB5 has ameliorated glomerulonephritis by reducing the expression of PDGF, its β-receptor and STAT3 in vivo and in vitro.

Glomerulosclerosis is characterized mainly by increase in the amount of ECM in the mesangium. One of the major components of glomerulosclerosis is Col4 (A34). The inventors have recently reported that Smad1 is a key transcriptional factor for regulating Col4 expression in diabetic nephropathy in vitro and in vivo (A8). The inventors have demonstrated that phosphorylated Smad1 is strongly expressed in parallel with the upregulation of Col4 expression and the increase in the amount of glomerular ECM. These findings elucidate that Smad1 plays a critical role not only in glomerulosclerosis in diabetic nephropathy but also in glomerulonephritis. This study has also shown that PDGF induces expression of phosphorylated Smad1 in the glomeruli in vitro and in vivo.

The inventors confirmed that the interaction between STAT3 and Smad1 regulates a gene critical for glomerulosclerosis. Introduction of dominant negative STAT3 decreased the expression of Col4 significantly in cultured mesangial cells. Activation of STAT3 and activation of Smad1 seem to be independent but both factors were activated by PDGF. Furthermore, since introduction of dominant negative STAT3 partially reduced phosphorylation of Smad1, activation of Smad1 seems to be a part of the mechanism of activating SMAT3. These findings suggest that, in experimental glomerulonephritis, PDGF-induced STAT3 activation interacts with overexpression of Smad1, which is followed by activation of Col4. To understand both signaling pathways is essential for elucidating the pathological process of progressive glomerular disorders.

Therapeutical approach for sclerosis in diverse organs is currently limited to supportive therapy to slow the loss of function of these organs. The findings of the present inventors offer insights into the nature of even other proliferative diseases that lead to sclerosis. Since both Smad1 and STAT3 are nearly absent in normal glomeruli, blocking Smad1 and/or STAT3 signals may be beneficial to inhibit the progress of various renal diseases leading to sclerosis, by inhibiting the pathologically activated cell proliferation and production of ECM.

EXAMPLE 3

Urine samples from five patients with diabetic nephropathy, one patient with diabetes complicated with sclerosing nephritis, two patients with diabetes complicated with non-sclerosing nephritis, and two healthy persons were subjected to SDS-polyacrylamide gel electrophoresis, followed by blotting on nitrocellulose membrane. Western blotting was performed using anti-Smad1 antibody (Santa Cruz Biotechnology) and anti-ALK1 antibody as primary antibodies and Western Breeze kit (Invitrogen, Tokyo, Japan).

Urine samples taken from one inpatient with diabetic nephropathy prior to treatment and one week after start of the treatment were subjected to Western blotting in the same manner, using anti-ALK1 antibody as a primary antibody.

Figure 17:
FIG. 17 shows the results of Western blotting on urine samples from patients and healthy persons using anti-ALK-1 antibody as a primary antibody. Lanes 1-5: diabetic nephropathy patients; lane 6: patient with mitochondrial disease in which diabetes is complicated with a sclerosing, renal proliferative disease; lanes 7 and 8: patients with diabetes complicated with a non-sclerosing renal disease; lanes 9 and 10: healthy persons.
Figure 19:
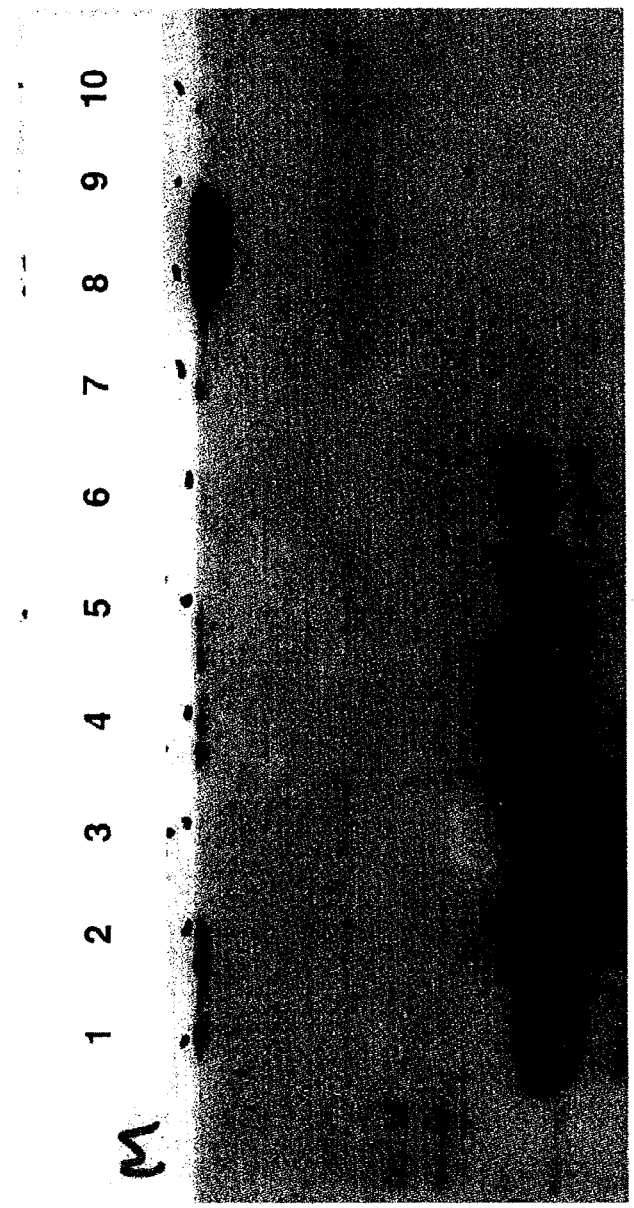
FIG. 19 shows the results of Western blotting on urine samples from patients and healthy persons using anti-Smad1 antibody as a primary antibody. Lanes 1-5: diabetic nephropathy patients; lane 6: patient with mitochondrial disease in which diabetes is complicated with a sclerosing, renal proliferative disease; lanes 7 and 8: patients with diabetes complicated with a non-sclerosing renal disease; lanes 9 and 10: healthy persons.

While Smad1 and ALK1 were detected in urine samples from patients with diabetic nephropathy and patient with glomerulosclerosis in the kidney, they were not detected in urine samples from normal persons and nephritis patients without glomerulosclerosis (FIGS. 17 and 19). The amount of ALK1 excreted into urine decreased in a time-dependent manner as treatment of diabetic nephropathy progressed (FIG. 18).

REFERENCES

1. The Diabetes Control and Complications Trial Research Group. *N. Engl. J Med* 329, 977-986 (1993).

2. UK Prospective Diabetes Study (UKPDS) Group. *Lancet* 352, 837-853 (1998)
3. H. Vlassara, et al., *Proc. Natl. Acad. Sci. USA* 91, 11704-11708 (1994).
4. M. Brownlee, A. Cerami, H. Vlassara, *N. Engl. J. Med.* 318, 1315-1321 (1988).
5. T. Doi, et al., *Proc. Natl. Acad. Sci. USA* 89, 2873-2877 (1992).
6. H. Vlassara, et al., *Proc. Natl. Acad. Sci. USA* 89,12043-12047 (1992).
7. M. S. Huijberts, et al., *J Clin. Invest.* 92, 1407-1411 (1993).
8. S. L. Park, et al., *Nature Med* 9, 1025-1031 (1998)
9. L. A. Bruggeman, P. D. Burbelo, Y Yamada, P. E. Klotman, *Oncogene* 7, 1497-1502 (1992).
10. N. Iehara, H. Takeoka, Y. Yamada, T. Kita, T. Doi, *Kidney Int.* 50, 1166-1172 (1996).
11. C. H. Heldin, K. Miyazono, P. ten Dijke, *Nature* 390, 465-471 (1997).
12. J. Massague, D Wotton, *EMBO J.* 19, 1745-1754 (2000).
13. B. A. Roelen, M. A. van Rooijen, C. L. Mummery, *Dev. Dyn.* 209, 418-430 (1997).
14. L. Attisano, et al., *Cell* 75, 671-680 (1993)
15. L. D. Urness, L. K. Sorensen, D. Y Li, *Nature Genet.* 26, 328-331 (2000).
16. J. Larsson, et al., *EMBO J.* 20, 1663-1673 (2001).
17. D. W. Johnson, et al. *Nature Genet.* 13, 189-195 (1996)
18. S. P. Oh, et al., *Proc. Natl. Acad. Sci. USA* 97, 2626-2631 (2000).
19. Y. G Chen, J. Massague, *J. Biol Chem.* 274, 3672-3677 (1999).
20. K. D. Tremblay, N. R. Dunn, E. J. Robertson, *Development* 128, 3609-3621 (2001)
21. A. Dick, W. Risau, H. Drexler, *Dev. Dyn.* 211,293-305 (1998)
22. S. Huang, K. C. Flanders, A. B. Roberts, *Gene*, 258, 43-53 (2000)
23. H. Vlassara, et al., *Proc. Natl. Acad. Sci. USA.* 91, 11704-11708 (1994).
24. Z. Makita, et al., *N. Engl. J. Med.* 325, 836-842 (1991).
25. O. Chappey, C. Dosquet, M. P. Wautier, J. L. Wautier, *Eur J Clin. Invest.* 27, 97-108 (1997)
26. Vasan, et al., *Nature* 382,275-278 (1996)
27. M. Brownlee, H. Vlassara, A. Kooney, P. Ulrich, A. Cerami, *Science* 27, 1629-1632 (1986).
28. We thank K. Miyazono for providing a plasmid encoding Smad1, and Y Takishita for his assistance with histological analysis. We also thank the members of our laboratory for discussion.
Supproted by Grant-in Aid from the Ministry of Education, Science, Sports and Culture of Japan.
S1. C. W. Yang, et al., *Proc. Natl. Acad. Sci. USA* 91, 9436-9440 (1994).
S2. M. Davies, The mesangial cell: a tissue culture view. *Kidney Int.* 45, 320-327 (1994).
S3. N. Iehara, H. Takeoka, Y. Yamada, T. Kita, T. Doi, *Kidney Int.* 50, 1166-1172 (1996).
S4. P. D. Burbelo, A. Utani, Z. Q. Pan, Y Yamada, *Proc. Natl. Acad. Sci. USA* 90, 11543-11547 (1993).
S5. R. X. Luo, A. A. Postigo, D. C. Dean, *Cell* 92, 463-473 (1998).
S6. H. Abe, N. Iehara, K. Utsunomiya, T. Kita, T. Doi, *J. Biol. Chem.* 274, 20874-20878 (1999).
S7. D. G Ahn, M. J. Kourakis, L. A. Rohde, L. M. Silver, R. K. Ho, *Nature* 417, 754-758 (2002).
A1. Fogo A, Ichikawa I. Evidence for the central role of glomerular growth promoters in the development of sclerosis. Semin Nephrol. 1989 Dec;9(4):329-42.
A2. Striker L J, Doi T, Elliot S, Striker G E. The contribution of glomerular mesangial cells to progressive glomerulosclerosis. Semin Nephrol. 1989 Dec;9(4):318-28. Review.
A3. Floege J, Johnson R J: Multiple roles for platelet-derived growth factor in renal disease. Miner Electrolyte Metab 21: 271-282, 1995
A4. Doi T, Vlassara H, Kirstein M, Yamada Y, Striker G E, Striker L J: Receptor-specific increase in extracellular matrix production by mesangial cells by advanced glycosylation end products is mediated via platelet-derived growth factor. Proc Natl Acad Sci USA 89: 2873-2877, 1992
A5. Barnes J L, Hevey K A. Glomerular mesangial cell migration in response to platelet-derived growth factor. Lab Invest. 1990 Mar;62(3):379-82.
A6. Floege, J., Burns, M. W., Alpers, C. E., Yoshimura, A., Pritzl, P., Gordon, K., Seifert, R. A., Bowen-Pope, D. F., Couser, W. G, and Johnson, R. J.: Glomerular cell proliferation and PDGF expression precede glomerulosclerosis in the remnant kidney model. Kidney Int. 41: 297-309, 1992
A7. Johnson, R. J., Raines, E. W., Floege, J, et al: Inhibition of mesangial cell proliferation and matrix expansion in glomerulonephritis in the rat by antibody to platelet-derived growth factor. J Exp Med 175: 1413-1416, 1992
A8. Abe, H., Matsubara, T., Iehara, N., Nagai, K., Takahashi, T., Arai, H., Kita, T., and Doi, T. Type IV collagen is transcriptionally regulated by Smad1 under advanced glycation end-products (AGEs) stimulation. (2004) J. Biol. Chem. 2004
A9. Yang X, Ji X, Shi X, Cao X. Smad1 domains interacting with Hoxc-8 induce osteoblast differentiation. J Biol Chem. 2000 Jan 14; 275(2): 1065-72.
A10. Katagiri T, Imada M, Yanai T, Suda T, Takahashi N, Kamijo R. Identification of a BMP-responsive element in Id1, the gene for inhibition of myogenesis. Genes Cells. 2002 Sep;7(9):949-60.
A11. Liu Z, Shi W, Ji X, Sun C, Jee W S, Wu Y, Mao Z, Nagy T R, Li Q, Cao X. Molecules mimicking Smad1 interacting with Hox stimulate bone formation. J Biol Chem. 2004 Mar 19;279(12):11313-9.
A12. Dick A, Risau W, Drexler H. Expression of Smad1 and Smad2 during embryogenesis suggests a role in organ development. Dev Dyn. 1998 Apr;211 (4):293-305.
A13. Vignais M L, Sadowski H B, Watling D, Rogers N C, Gilman M. Platelet-derived growth factor induces phosphorylation of multiple JAK family kinases and STAT proteins. Mol Cell Biol. 1996 Apr; 16(4): 1759-69.
A14. Nakashima K, Yanagisawa M, Arakawa H, Kimura N, Hisatsune T. Kawabata M, Miyazono K, Taga T. Synergistic signaling in fetal brain by STAT3-Smad1 complex bridged by p300. Science. 1999 Apr 16;284(5413):479-82.
A15. Bokemeyer D, Ostendorf T, Kunter U, Lindemann M, Kramer H J, Floege J: Differentioal activation of mitogen-activated protein kinases in experimental mesangioproliferative glomerulonephritis. J Am Soc Nephrol 11: 232-240, 2000
A16. Sano H, Sudo T, Yokode M, Murayama T, Kataoka H, Takakura N, Nishikawa S, Nishikawa S I, Kita T: Function blockade of platelet-derived growth factor receptor-beta but not of receptor-alpha prevent vascular smooth muscle cell accumulation in fibrous cap lesions inapolipoprotein E-deficient mice. Circulation 2001, 103: 2955-2960
A17. Sano H, Ueda Y, Takakura N, Takemura G. Doi T, Kataoka H, Murayama T, Xu Y, Sudo T, Nishikawa S, Nishikawa S, Fujiwara H, Kita T, Yokode M: Blockade of platelet-derived growth factor receptor-beta pathway induces apoptosis of vascular endothelial cells and disrupts glomerular capillary formation in neonatal mice. Am J Pathol 2002, 161:135-143.

A18. Yamamoto Y, Kato I, Doi T, Yonekura H, Ohashi S, Takeuchi M, Watanabe T, Yamagishi S, Sakurai S, Takasawa S, Okamoto H, Yamamoto H. Development and prevention of advanced diabetic nephropathy in RAGE-overexpressing mice. J Clin Invest. 2001 Jul;108(2):261-8.

A19. Makibayashi K, Tatematsu M, Hirata M, Fukushima N, Kusano K, Ohashi S, Abe H, Kuze K, Fukatsu A, Kita T, Doi T. A vitamin D analog ameliorates glomerular injury on rat glomerulonephritis. Am J Pathol. 2001 May;158(5): 1733-41.

Makibayashi, K., Tatematsu, M., Hirata, M., Fukushima, N., Kusano, K., Ohashi, S., Abe, H., Kuze, K., Fukatsu, A., Kita, T., and Doi, T. (2001) Am J Pathol. 158, 1733-1741

A20. Nagai K, Arai H, Yanagita M, Matsubara T, Kanamori H, Nakano T, Iehara N, Fukatsu A, Kita T, Doi T: Growth arrest-specific gene 6 is involved in glomerular hypertrophy in the early stage of diabetic nephropathy. J Biol Chem 278: 18229-18234: 2003

A21. Davies M. The mesangial cell: a tissue culture view. Kidney Int. 1994 Feb;45(2):320-7.

A22. Striker G E, Striker L. J: Glomerular cell culture. Lab Invest, 1985 53: 122-131

A23. Bromberg J F, Horvath C M, Besser D, Lathem W W, Darnell J E Jr. Stat3 activation is required for cellular transformation by v-src. Mol Cell Biol. 1998 May; 18(5): 2553-8.

A24. Schindler C, Darnell J E Jr. Transcriptional responses to polypeptide ligands: the JAK-STAT pathway. Annu Rev Biochem. 1995;64:621-51.

A25. Klahr S, Schreiner G. Ichikawa I. The progression of renal disease. N Engl J. Med. 1988 Jun 23;318(25): 1657-66.

A26. Striker L J, Doi T, Elliot S, Striker G E. The contribution of glomerular mesangial cells to progressive glomerulosclerosis.Semin Nephrol. 1989 Dec;9(4):318-28.

A27. Olson J L. Role of heparin as a protective agent following reduction of renal mass. *Kidney Int.* 1984 Feb;25(2): 376-82.

A28. Shultz P J, DiCorleto P E, Silver B J, Abboud H E. Mesangial cells express PDGF mRNAs and proliferate in response to PDGF. Am J Physiol. 1988 Oct;255(4 Pt 2):F674-84.

A29. Abboud H E, Poptic E, DiCorleto P. Production of platelet-derived growth factorlike protein by rat mesangial cells in culture. J Clin Invest. 1987 Sep;80(3):675-83.

A30. Choudhury G O, Marra F, Kiyomoto H, Abboud H E. PDGF stimulates tyrosine phosphorylation of JAK 1 protein tyrosine kinase in human mesangial cells. Kidney Int. 1996 Jan;49(1):19-25.

A31. Vignais M L, Sadowski H B, Watling D, Rogers N C, Gilman M. Platelet-derived growth factor induces phosphorylation of multiple JAK family kinases and STAT proteins. Mol Cell Biol. 1996 Apr;16(4):1759-69.

A32. Meloche S, Pelletier S, Servant M J. Functional crosstalk between the cyclic AMP and Jak/STAT signaling pathways in vascular smooth muscle cells. Mol Cell Biochem. 2000 Sep;212(1-2):99-109.

A33. Yanagita M, Arai H, Nakano T, Ohashi K, Mizuno K, Fukatsu A, Doi T, Kita T. Gas6 induces mesangial cell proliferation via latent transcription factor STAT3. J Biol Chem. 2001 Nov 9;276(45):42364-9.

A34. Floege J, Johnson R J, Gordon K, Iida H, Pritzl P, Yoshimura A, Campbell C, Alpers C E, Couser W G Increased synthesis of extracellular matrix in mesangial proliferative nephritis. Kidney Int. 1991 Sep;40(3):477-88.

All publications, patents and patent applications cited herein are incorporated herein by reference in their entirety.

INDUSTRIAL APPLICABILITY

According to the present invention, Smad1 has been identified as a substance directly involved in the overproduction of type IV collagen and shown to have a critical role as a causative of diabetic nephropathy. With this finding, it has become possible to detect diabetic nephropathy; and there have been provided a prophylactic and/or therapeutic agent for diabetic nephropathy, a drug inhibiting the increase of extracellular matrix, and a drug inhibiting the expression of α1 type IV collagen. Further, according to the present invention, there have been provided a method and a kit for identifying substances effective in preventing and/or treating diabetic nephropathy, a method and a kit for identifying substances effective in inhibiting the increase of extracellular matrix, and a method and a kit for identifying substances effective in inhibiting the expression of α1 type IV collagen.

According to the present invention, it has been demonstrated that activation of STAT3 and Smad1 is in a key pathway for regulating the interaction between the two critical events (i.e., cell proliferation and glomerulosclerosis) in progressive glomerular disorders. With this finding, it has become possible to detect proliferative diseases causing sclerosis; and there have been provided a prophylactic and/or therapeutic agent for proliferative diseases causing sclerosis, a drug inhibiting the increase of extracellular matrix, and a drug inhibiting the expression of α1 type IV collagen. Further, according to the present invention, there have been provided a method and a kit for identifying substances effective in preventing and/or treating proliferative diseases causing sclerosis, a method and a kit for identifying substances effective in inhibiting the increase of extracellular matrix, and a method and a kit for identifying substances effective in inhibiting the expression of α1 type IV collagen.

Sequence Listing Free Text

<SEQ ID NO: 1>

SEQ ID NO: 1 shows the nucleotide sequence of the mRNA of human-derived Smad1.

<SEQ ID NO: 2>

SEQ ID NO: 2 shows the nucleotide sequence of the mRNA of human-derived ALK1.

<SEQ ID NO: 3>

SEQ ID NO: 3 shows the nucleotide sequence of the mRNA of human-derived BMP2.

<SEQ ID NO: 4>

SEQ ID NO: 4 shows the nucleotide sequence of the mRNA of human-derived BMP4.

<SEQ ID NO: 5>

SEQ ID NO: 5 shows the nucleotide sequence of the forward primer used in RT-PCR for specifically amplifying the mRNA of Smad1.

<SEQ ID NO: 6>

SEQ ID NO: 6 shows the nucleotide sequence of the reverse primer used in RT-PCR for specifically amplifying the mRNA of Smad1.

<SEQ ID NO: 7>

SEQ ID NO: 7 shows the nucleotide sequence of the forward primer used in RT-PCR for specifically amplifying the mRNA of ALK1.

<SEQ ID NO: 8>
SEQ ID NO: 8 shows the nucleotide sequence of the reverse primer used in RT-PCR for specifically amplifing the mRNA of ALK1.
<SEQ ID NO: 9>
SEQ ID NO: 9 shows the nucleotide sequence of the forward primer used in RT-PCR for specifically amplifying the mRNA of BMP2.
<SEQ ID NO: 10>
SEQ ID NO: 10 shows the nucleotide sequence of the reverse primer used in RT-PCR for specifically amplifying the mRNA of BMP2.
<SEQ ID NO: 11>
SEQ ID NO: 11 shows the nucleotide sequence of the forward primer used in RT-PCR for specifically amplifying the mRNA of BMP4.
<SEQ ID NO: 12>
SEQ ID NO: 12 shows the nucleotide sequence of the reverse primer used in RT-PCR for specifically amplifying the mRNA of BMP4.
<SEQ ID NO: 13>
SEQ ID NO: 13 shows the nucleotide sequence of an antisense oligonucleotide to Smad1.
<SEQ ID NO: 14>
SEQ ID NO: 14 shows the nucleotide sequence of the 27 bp tandem repeat sequence of mouse-derived Col4 gene.
<SEQ ID NO: 15>
SEQ ID NO: 15 shows the nucleotide sequence of the 5' primer used in ChIP assay.
<SEQ ID NO: 16>
SEQ ID NO: 16 shows the nucleotide sequence of the 3' primer used in ChIP assay.
<SEQ ID NO: 17>
SEQ ID NO: 17 shows the nucleotide sequence of the probe used in RNase protection assay.
<SEQ ID NO: 18>
SEQ ID NO: 18 shows the nucleotide sequence of a synthetic oligonucleotide.

<SEQ ID NO: 19>
SEQ ID NO: 19 shows the nucleotide sequence of the mRNA of human-derived STAT3.
<SEQ ID NO: 20>
SEQ ID NO: 20 shows the nucleotide sequence of the mRNA of human-derived ALK3.
<SEQ ID NO: 21>
SEQ ID NO: 21 shows the nucleotide sequence of the forward primer used in RT-PCR for specifically amplifying the mRNA of human-derived STAT3.
<SEQ ID NO: 22>
SEQ ID NO: 22 shows the nucleotide sequence of the reverse primer used in RT-PCR for specifically amplifying the mRNA of human-derived STAT3.
<SEQ ID NO: 23>
SEQ ID NO: 23 shows the nucleotide sequence of the forward primer used in RT-PCR for specifically amplifying the mRNA of human-derived ALK3.
<SEQ ID NO: 24>
SEQ ID NO: 24 shows the nucleotide sequence of the reverse primer used in RT-PCR for specifically amplifying the mRNA of human-derived ALK3.
<SEQ ID NO: 25>
SEQ ID NO: 25 shows the encoded amino acid sequence of SEQ ID NO: 1.
<SEQ ID NO: 26>
SEQ ID NO: 26 shows the encoded amino acid sequence of SEQ ID NO: 2.
<SEQ ID NO: 27>
SEQ ID NO: 27 shows the encoded amino acid sequence of SEQ ID NO: 3.
<SEQ ID NO: 28>
SEQ ID NO: 28 shows the encoded amino acid sequence of SEQ ID NO: 4.
<SEQ ID NO: 29>
SEQ ID NO: 29 shows the encoded amino acid sequence of SEQ ID NO: 19.
<SEQ ID NO: 30>
SEQ ID NO: 30 shows the encoded amino acid sequence of SEQ ID NO: 20.

The invention claimed is:

1. A method of identifying an agent effective in preventing and/or treating a proliferative disease causing sclerosis, comprising
   contacting a test agent with a biological sample;
   determining the level of expression of at least one substance selected from the group consisting of Smad1 and phosphorylated Smad1 in the biological sample in comparison to the level of expression of the substance in a control sample;
   wherein a decrease in expression of Smad1 or phosphorylated Smad1 in comparison to the expression level of the substance in the control sample indicates the agent is effective in the prevention and/or treatment of proliferative diseases causing sclerosis.

2. A method of identifying an agent effective in inhibiting the increase of extracellular matrix, comprising
   contacting a test agent with a biological sample;
   determining the level of expression of at least one substance selected from the group consisting of Smad1 and phosphorylated Smad1 in the biological sample in comparison to the level of expression of the substance in a control sample;
   wherein a decrease in expression of Smad1 or phosphorylated Smad1 in comparison to the expression level of the substance in the control sample indicates the agent is effective in inhibiting the increase of extracellular matrix.

3. A method of identifying substances effective in inhibiting the expression of α1 type IV collagen, comprising
   contacting a test agent with a biological sample;
   determining the level of expression of at least one substance selected from the group consisting of Smad1 and phosphorylated Smad1 in the biological sample in comparison to the level of expression of the substance in a control sample,
   wherein a decrease in expression of Smad1 or phosphorylated Smad1 in comparison to the expression level of the substance in the control sample indicates the agent is effective in inhibiting the expression of α1 type IV collagen.

4. The method of any one of claims 1, 2, or 3, wherein the biological sample is selected from the group consisting of renal tissue sections, blood, sera and urine.

5. The method of any one of claims 1, 2, or 3, wherein the biological sample is selected from mesangial cells.

6. The method of any one of claims 1, 2, or 3, wherein the level of expression is measured at the nucleic acid level or the protein level.

7. The method of claim 1, wherein the proliferative disease causing sclerosis is a renal disease which damages glomeruli.

8. The method of claim 1, wherein the proliferative disease causing sclerosis is selected from the group consisting of diabetic nephropathy, chronic glomerulonephritis, membranous proliferative glomerulonephritis, focal glomerulosesclerosis, light chain disease, cryoglobulinemic nephritis, HIV-associated nephritis, purpuric nepbritis, hepatic fibrosis, and arteriosclerosis.

9. A method of identifying an agent effective in preventing and/or treating a proliferative disease causing sclerosis, or effective in inhibiting the increase of extracellular matrix, or effective in inhibiting the expression of α1 type IV collagen comprising
   contacting a test agent with a biological sample;
   determining the level of expression of at least one substance selected from the group consisting of STAT3, phosphorylated STAT3, Smad1 and phosphorylated Smad1 in the biological sample in comparison to the level of expression of the substance in a control sample,
   wherein a decrease in expression of STAT3. phosphorylated STAT3, Smad1 or phosphorylated Smad1 in comparison to the expression level of the substance in the control sample indicates the agent is effective in the prevention and/or treatment of proliferative diseases causing sclerosis, or effective in inhibiting the increase of extracellular matrix or effective in inhibiting the expression of α1 type IV collagen,
   and wherein the level of expression of STAT3, phosphorylated STAT3, Smad1 or phosphorylated Smad1 at the nucleic acid level is measured using primer pairs selected from SEQ ID NOS: 21 and 22, or SEQ ID NOS: 5 and 6.

10. The method of any one of claims 1, 2, or 3, wherein the level of expression of, Smad1 or phosphorylated Smad1 at the protein level is measured by Western Blotting, ELISA or immunohistochemical analysis.

* * * * *